(12) United States Patent
Li et al.

(10) Patent No.: US 9,447,088 B2
(45) Date of Patent: *Sep. 20, 2016

(54) COMPOSITIONS AND METHODS FOR TREATMENT OF CANCER

(71) Applicant: ArQule, Inc., Woburn, MA (US)

(72) Inventors: Chiang J. Li, Cambridge, MA (US);
Mark A. Ashwell, Carlisle, MA (US);
Jason Hill, Auburndale, MA (US);
Magdi Moussa, Malden, MA (US);
Neru Munshi, Burlington, MA (US)

(73) Assignee: ArQule, Inc., Burlington, MA (US)

( * ) Notice: Subject to any disclaimer, the term of this patent is extended or adjusted under 35 U.S.C. 154(b) by 56 days.

This patent is subject to a terminal disclaimer.

(21) Appl. No.: 14/215,852

(22) Filed: Mar. 17, 2014

(65) Prior Publication Data

US 2014/0200199 A1    Jul. 17, 2014

Related U.S. Application Data

(62) Division of application No. 13/761,712, filed on Feb. 7, 2013, now Pat. No. 8,754,078, which is a division of application No. 12/722,394, filed on Mar. 11, 2010, now Pat. No. 8,377,927, which is a division of application No. 11/350,335, filed on Feb. 9, 2006, now Pat. No. 7,713,969.

(60) Provisional application No. 60/650,951, filed on Feb. 9, 2005.

(51) Int. Cl.

| A61K 31/4745 | (2006.01) |
|---|---|
| C07D 471/06 | (2006.01) |
| C07D 455/00 | (2006.01) |
| C07D 487/06 | (2006.01) |
| C07F 9/6558 | (2006.01) |
| C07F 9/6561 | (2006.01) |
| A61K 31/138 | (2006.01) |
| A61K 31/337 | (2006.01) |
| A61K 31/4535 | (2006.01) |
| A61K 31/513 | (2006.01) |
| A61K 31/5377 | (2006.01) |
| A61K 31/5517 | (2006.01) |
| A61K 31/664 | (2006.01) |
| A61K 31/675 | (2006.01) |
| A61K 31/704 | (2006.01) |
| A61K 31/7048 | (2006.01) |
| A61K 31/7068 | (2006.01) |
| A61K 38/08 | (2006.01) |
| A61K 38/12 | (2006.01) |
| C07K 2/00 | (2006.01) |

(52) U.S. Cl.
CPC ........... *C07D 455/00* (2013.01); *A61K 31/138* (2013.01); *A61K 31/337* (2013.01); *A61K 31/4535* (2013.01); *A61K 31/4745* (2013.01); *A61K 31/513* (2013.01); *A61K 31/5377* (2013.01); *A61K 31/5517* (2013.01); *A61K 31/664* (2013.01); *A61K 31/675* (2013.01); *A61K 31/704* (2013.01); *A61K 31/7048* (2013.01); *A61K 31/7068* (2013.01); *A61K 38/08* (2013.01); *A61K 38/12* (2013.01); *C07D 471/06* (2013.01); *C07D 487/06* (2013.01); *C07F 9/6561* (2013.01); *C07F 9/65583* (2013.01); *C07K 2/00* (2013.01)

(58) Field of Classification Search
CPC .......................... A61K 31/4745; C07D 471/06
USPC .................. 514/233.2, 294; 544/126; 546/94
See application file for complete search history.

(56) References Cited

U.S. PATENT DOCUMENTS

| 4,522,811 A | 6/1985 | Eppstein et al. |
|---|---|---|
| 5,057,614 A | 10/1991 | Davis et al. |
| 5,292,747 A | 3/1994 | Davis et al. |
| 5,380,746 A | 1/1995 | Barth et al. |
| 5,516,915 A | 5/1996 | Barth et al. |
| 5,534,636 A | 7/1996 | Tegeler et al. |
| 5,545,636 A | 8/1996 | Heath, Jr. et al. |
| 5,559,228 A | 9/1996 | Gillig et al. |
| 5,591,842 A | 1/1997 | Kojiri et al. |
| 5,591,855 A | 1/1997 | Hudkins et al. |

(Continued)

FOREIGN PATENT DOCUMENTS

| EP | 0 384 349 A1 | 8/1990 |
|---|---|---|
| EP | 0 397 060 A2 | 11/1990 |

(Continued)

OTHER PUBLICATIONS

Al-Awar, et al. "1, 7-Annulated Indolocarbazoles as Cyclin-Dependent Kinase Inhibitors," Bioorganic & Medicinal Chemistry Letters, 14: 3217-3220 (2004).

(Continued)

*Primary Examiner* — Brenda Coleman
(74) *Attorney, Agent, or Firm* — Cooley LLP; Matthew Pavao; Chen Chen

(57) ABSTRACT

The present invention relates to pyrroloquinolinyl-pyrrolidine-2,5-dione compounds in combination with chemotherapeutic agents. The present invention provides methods of treating a cell proliferative disorder, such as a cancer, by administering to a subject in need thereof a therapeutically effective amount of a pyrroloquinolinyl-pyrrole-2,5-dione compound or pyrroloquinolinyl-pyrrolidine-2,5-dione compound of the present invention and also administering a effective amount of a chemotherapeutic agent.

17 Claims, 12 Drawing Sheets

(56) References Cited

U.S. PATENT DOCUMENTS

| | | | |
|---|---|---|---|
| 5,721,230 | A | 2/1998 | Harris et al. |
| 5,721,245 | A | 2/1998 | Davis et al. |
| 5,856,517 | A | 1/1999 | Huryn et al. |
| 5,859,261 | A | 1/1999 | Faul et al. |
| RE36,736 | E | 6/2000 | Davis et al. |
| 6,153,641 | A | 11/2000 | Bergstrand et al. |
| 6,524,832 | B1 | 2/2003 | Kufe et al. |
| 6,867,198 | B2 | 3/2005 | Al-Awar et al. |
| 7,070,968 | B2 | 7/2006 | Kufe et al. |
| 7,713,969 | B2 | 5/2010 | Li et al. |
| 8,552,192 | B2 * | 10/2013 | Reed ............... C07D 471/06 546/94 |
| 9,180,099 | B2 * | 11/2015 | Yamakose ............ A61K 9/2018 |
| 2006/0251734 | A1 | 11/2006 | Kufe et al. |
| 2010/0221251 | A1 | 9/2010 | Li et al. |

FOREIGN PATENT DOCUMENTS

| | | |
|---|---|---|
| EP | 0 825 190 A1 | 2/1998 |
| EP | 1 120 414 A1 | 8/2001 |
| WO | WO 91/13070 | 9/1991 |
| WO | WO 91/13071 | 9/1991 |
| WO | WO 93/18765 | 9/1993 |
| WO | WO 95/17182 | 6/1995 |
| WO | WO 95/30682 | 11/1995 |
| WO | WO 97/34890 | 9/1997 |
| WO | WO 98/04551 | 2/1998 |
| WO | WO 98/04552 | 2/1998 |
| WO | WO 98/16528 | 4/1998 |
| WO | WO 00/47575 A1 | 8/2000 |
| WO | WO 01/44235 A2 | 6/2001 |
| WO | WO 01/44247 A2 | 6/2001 |
| WO | WO 01/74807 A1 | 10/2001 |
| WO | WO 01/85685 A1 | 11/2001 |
| WO | WO 02/02593 A2 | 1/2002 |
| WO | WO 03/066802 | 8/2003 |
| WO | WO 03/066808 A2 | 8/2003 |
| WO | WO 03/076442 A1 | 9/2003 |
| WO | WO 2004/091548 A2 | 10/2004 |
| WO | WO 2004/096224 A2 | 11/2004 |
| WO | WO 2005/001486 A1 | 1/2005 |
| WO | WO 2005/007193 A2 | 1/2005 |
| WO | WO 2005/058965 A1 | 6/2005 |
| WO | WO 2006/086484 A1 | 8/2006 |
| WO | WO 2006/105511 A1 | 10/2006 |

OTHER PUBLICATIONS

Davis, et al. "Inhibitors of Protein Kinase C.1 2, 3-Bisarylmaleimides," Journal of Medicinal Chemistry, 35:177-184 (1992).

Li, et al. "An Improved Protocol for the Preparation of 3- Pyridyl- and Some Arylboronic Acids," J. Org. Chem. 67:5394-5397(2002).

Marson, et al. "Highly Efficient Syntheses of 3-Aryl-2-cycloalken-1-ones and an Evaluation of Their Liquid Crystalline Properties," Tetrahedron 59: 4377-4381 (2003).

Slater, et al. "Indolocarbazoles: Potent, Selective Inhibitors of Human Cytomegalovirus Replication," Bioorganic & Medicinal Chemistry 7: 1067-1074 (1999).

Walker "Staurosporine: Discovery of a Potential Anti-Cancer Drug?" http://freespace.virgin.net!clive.walkerl/staurosporine/staurosporine2.h1ml, 2001.

Zhu, et al. "Synthesis of 1,7-Annulated Indoles and Their Applications in the Studies of Cyclin Dependent Kinase Inhibitors, " Bioorganic & Medicinal Chemistry Letters 14:3057-3061 (2004).

Sharma, S., et al. "Cell Line-Based Platforms to Evaluate the Therapeutic Efficacy of Candidate Anticancer Agents," Nature Reviews/Cancer, vol. 10, pp. 241-253, Apr. 2010.

Barretina, J., et al., "The Cancer Cell Line Encyclopedia Enables Predictive Modeling of Anticancer Drug Sensitivity" Nature, vol. 483, pp. 603-607, Mar. 29, 2012.

* cited by examiner (±)-trans-3-(5,6-dihydro-4H-pyrrolo [3,2,1-ij] quinolin-1-yl)-4(1H-indol-3-yl) pyrrolidine-2, 5-dione (±)-cis-3-(5,6-dihydro-4H-pyrrolo [3,2,1-ij] quinolin-1yl)-4(1H-indol-3-yl) pyrrolidine-2, 5-dione (−)-trans-3-(5,6-dihydro-4H-pyrrolo [3,2,1-ij] quinolin-1-yl)-4(1H-indol-3-yl) pyrrolidine-2, 5-dione $LC_{50} = 0.62\ \mu M$ (+)-trans-3-(5,6-dihydro-4H-pyrrolo [3,2,1-ij] quinolin-1-yl)-4(1H-indol-3-yl) pyrrolidine-2, 5-dione $LC_{50} = 4.1\ \mu M$ A= (-)-trans-3-(5,6-dihydro-4*H*-pyrrolo [3,2,1-*ij*] quinolin-1-yl)-4(1*H*-indol-3-yl) pyrrolidine-2, 5-dione B= (+)-trans-3-(5,6-dihydro-4*H*-pyrrolo [3,2,1-*ij*] quinolin-1-yl)-4(1*H*-indol-3-yl) pyrrolidine-2, 5-dione A= (±)-trans-3-(5,6-dihydro-4$H$-pyrrolo [3,2,1-$ij$] quinolin-1-yl)-4(1$H$-indol-3-yl) pyrrolidine-2, 5-dione
B= (±)-cis-3-(5,6-dihydro-4$H$-pyrrolo [3,2,1-$ij$] quinolin-1yl)-4(1$H$-indol-3-yl) pyrrolidine-2, 5-dione A= (±)-cis-3-(5,6-dihydro-4H-pyrrolo [3,2,1-ij] quinolin-1yl)-4(1H-indol-3-yl) pyrrolidine-2, 5-dione B= (±)-trans-3-(5,6-dihydro-4H-pyrrolo [3,2,1-ij] quinolin-1-yl)-4(1H-indol-3-yl) pyrrolidine-2, 5-dione

COMPOSITIONS AND METHODS FOR TREATMENT OF CANCER

CROSS-REFERENCE TO RELATED APPLICATIONS

This application is a divisional of U.S. Ser. No. 13/761,712, filed Feb. 7, 2013, allowed, which is a divisional of U.S. Ser. No. 12/722,394, filed Mar. 11, 2010, now U.S. Pat. No. 8,377,927, which is a divisional of U.S. Ser. No. 11/350,335, filed Feb. 9, 2006, now U.S. Pat. No. 7,713,969, which claims priority to and the benefit of U.S. Ser. No. 60/650,951, filed Feb. 9, 2005, the entire contents of each of which are incorporated herein by reference.

BACKGROUND OF THE INVENTION

Cancer is the second leading cause of death in the United States, exceeded only by heart disease. (*Cancer Facts and Figures* 2004, American Cancer Society, Inc.) Despite recent advances in cancer diagnosis and treatment, surgery and radiotherapy may be curative if a cancer is found early, but current drug therapies for metastatic disease are mostly palliative and seldom offer a long-term cure. Even with new chemotherapies entering the market, the need continues for new drugs effective in monotherapy or in combination with existing agents as first line therapy, and as second and third line therapies in treatment of resistant tumors.

Cancer cells are by definition heterogeneous. For example, within a single tissue or cell type, multiple mutational 'mechanisms' may lead to the development of cancer. As such, heterogeneity frequently exists between cancer cells taken from tumors of the same tissue and same type that have originated in different individuals. Frequently observed mutational 'mechanisms' associated with some cancers may differ between one tissue type and another (e.g., frequently observed mutational 'mechanisms' leading to colon cancer may differ from frequently observed 'mechanisms' leading to leukemias). It is therefore often difficult to predict whether a particular cancer will respond to a particular chemotherapeutic agent. (*Cancer Medicine*, 5th Edition, Bast et al. eds., B.C. Decker Inc., Hamilton, Ontario) Breast cancer is the most frequently diagnosed non-skin cancer in women, and ranks second among cancer deaths in women, after lung cancer. (*Cancer Facts and Figures* 2004, American Cancer Society, Inc.) Current treatment options for breast cancer include surgery, radiotherapy, and chemotherapy/hormone therapy with agents such as tamoxifen, aromatase inhibitors, HERCEPTIN® (trastuzumab), TAXOL® (paclitaxel), cyclophosphamide, methotrexate, doxorubicin (adriamycin), and 5-fluoruracil. Despite improvements in cancer diagnostics and therapeutics, breast cancer incidence rates have continued to increase since 1980. In 2004, about 215,000 new cases of breast cancer are expected in women, and about 1,450 new cases of breast cancer are expected in men. Id. Accordingly, new compounds and methods for treating breast cancer are needed.

Components of cellular signal transduction pathways that regulate the growth and differentiation of normal cells can, when dysregulated, lead to the development of cellular proliferative disorders and cancer. Mutations in cellular signaling proteins may cause such proteins to become expressed or activated at inappropriate levels or at inappropriate times during the cell cycle, which in turn may lead to uncontrolled cellular growth or changes in cell-cell attachment properties. For example, dysregulation of receptor tyrosine kinases by mutation, gene rearrangement, gene amplification, and overexpression of both receptor and ligand has been implicated in the development and progression of human cancers.

The c-Met receptor tyrosine kinase is the only known high-affinity receptor for hepatocyte growth factor (HGF), also known as scatter factor. Binding of HGF to the c-Met extracellular ligand-binding domain results in receptor multimerization and phosphorylation of multiple tyrosine residues in the intracellular portion of c-Met. Activation of c-Met results in the binding and phosphorylation of adaptor proteins such as Gab-1, Grb-2, Shc, and c-Cbl, and subsequent activation of signal transducers such as PI3K, PLC-γ, STATs, ERK1 and 2 and FAK. c-Met and HGF are expressed in numerous tissues, and their expression is normally confined predominantly to cells of epithelial and mesenchymal origin, respectively. c-Met and HGF are dysregulated in human cancers, and may contribute to dysregulation of cell growth, tumor cell dissemination, and tumor invasion during disease progression and metastasis. (See, e.g., *Journal of Clinical Investigation* 109: 863-867 (2002) and Cancer Cell pp 5-6 Jul. 2004) c-Met and HGF are highly expressed relative to surrounding tissue in numerous cancers, and their expression correlates with poor patient prognosis. (See, e.g., *Journal of Cellular Biochemistry* 86: 665-677 (2002); *Int. J. Cancer (Pred. Oncol.)* 74: 301-309 (1997); *Clinical Cancer Research* 9: 1480-1488 (2003); and *Cancer Research* 62: 589-596 (2002)). Without intending to be bound by theory, c-Met and HGF may protect tumors against cell death induced by DNA damaging agents, and as such may contribute to chemoresistance and radioresistance of tumors. Without intending to be limited by any theory, inhibitors of c-Met may be useful as therapeutic agents in the treatment of proliferative disorders including breast cancer. (See, e.g., *Cancer and Metastasis Reviews* 22: 309-325 (2003)).

The references cited herein are not admitted to be prior art to the claimed invention.

SUMMARY OF THE INVENTION

The present invention provides for pyrroloquinolinyl-pyrrolidine-2,5-dione compounds of formula IVa, IVb, Va, or Vb, and methods of preparing the compounds of formula IVa, IVb, Va, and Vb,

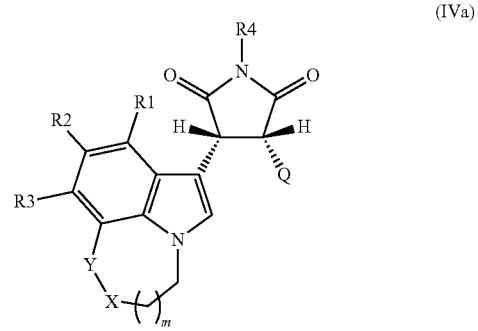

(IVa)

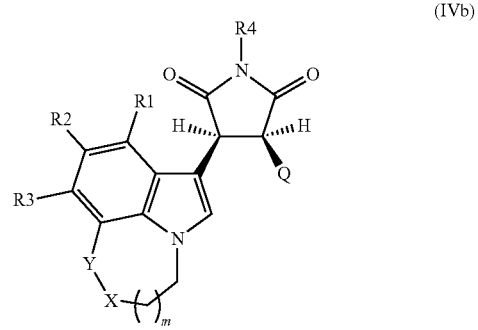

(IVb)

-continued

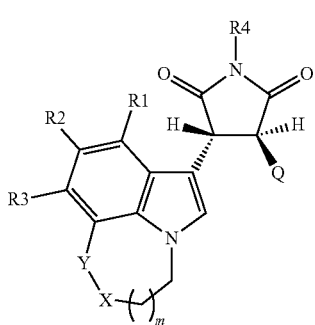
(Va)

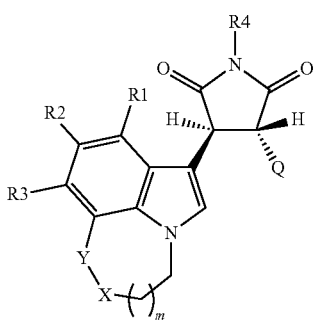
(Vb)

where:

R1, R2 and R3 are independently selected from the group consisting of hydrogen, F, Cl, Br, I, —NR5R6, —($C_1$-$C_6$) alkyl, —($C_1$-$C_6$) substituted alkyl, —($C_3$-$C_9$) cycloalkyl, —($C_3$-$C_9$) substituted cycloalkyl, —O—($C_1$-$C_6$) alkyl, —O—($C_1$-$C_6$) substituted alkyl, —O—($C_3$-$C_9$) cycloalkyl, and —O—($C_3$-$C_9$) substituted cycloalkyl, aryl, heteroaryl, heterocyclyl;

R4 is independently selected from the group consisting of hydrogen, —($C_1$-$C_6$) alkyl, —$CH_2$R7;

R5, R6 are independently selected from the group consisting of hydrogen, and —($C_1$-$C_6$) alkyl;

R7 is independently selected from the group consisting of —O—P(=O)(OH)$_2$, —O—P(=O)(—OH)(—O—($C_1$-$C_6$) alkyl), —O—P(=O)(—O—($C_1$-$C_6$) alkyl)$_2$, —O—P(=O)(—OH)(—O—($CH_2$)-phenyl), —O—P(=O)(—O—($CH_2$)-phenyl)$_2$, a carboxylic acid group, an amino carboxylic acid group and a peptide;

Q is selected from the group consisting of aryl, heteroaryl, —O-aryl, —S-aryl, —O-heteroaryl, and —S-heteroaryl;

X is selected from the group consisting of —($CH_2$)—, —(NR8)-, S, and O;

R8 is independently selected from the group consisting of hydrogen, —($C_1$-$C_6$) alkyl, —($C_1$-$C_6$) substituted alkyl, —($C_3$-$C_9$) cycloalkyl, —($C_3$-$C_9$) substituted cycloalkyl, and —O—($C_1$-$C_6$) alkyl, —C(=O)—O—($C_1$-$C_6$) alkyl and —C(=O)—O—($C_1$-$C_6$) substituted alkyl;

Y is selected from the group consisting of —($CH_2$)— or a bond;

wherein said aryl, heteroaryl, —O-aryl, —S-aryl, —O-heteroaryl, and —S-heteroaryl groups may be substituted with one or more substituents independently selected from the group consisting of F, Cl, Br, I, —NR5R6, —($C_1$-$C_6$) alkyl, —($C_1$-$C_6$) substituted alkyl, —($C_3$-$C_9$) cycloalkyl, —($C_3$-$C_9$) substituted cycloalkyl, —O—($C_1$-$C_6$) alkyl, —O—($C_1$-$C_6$) substituted alkyl, —O—($C_3$-$C_9$) cycloalkyl, —O—($C_3$-$C_9$) substituted cycloalkyl, -aryl, -aryl-($C_1$-$C_6$) alkyl, -aryl-O—($C_1$-$C_6$) alkyl, —O-aryl, —O—($C_1$-$C_4$) alkyl-aryl, heteroaryl, heterocyclyl, —O—($C_1$-$C_4$) alkyl-heterocycle, and —(S(=O)$_2$)—($C_1$-$C_6$) alkyl; and m is 1 or 2.

In an embodiment, R4 is —$CH_2$R7, and R7 is —O—P(=O)(OH)$_2$, —O—P(=O)(—OH)(—O—($C_1$-$C_6$) alkyl), —O—P(=O)(—O—($C_1$-$C_6$) alkyl)$_2$, a carboxylic acid group, an amino carboxylic acid group or a peptide.

In an embodiment, X is selected from the group consisting of —(NR8)-, S, and O.

In an embodiment, m is 2.

In a preferred embodiment, the pyrroloquinolinyl-pyrrolidine-2,5-dione compound is selected from the group consisting of (+)-cis-3-(5,6-dihydro-4H-pyrrolo[3,2,1-ij]quinolin-1yl)-4(1H-indol-3-yl)pyrrolidine-2,5-dione, (−)-cis-3-(5,6-dihydro-4H-pyrrolo[3,2,1-ij]quinolin-1 yl)-4(1H-indol-3-yl) pyrrolidine-2,5-dione, (+)-trans-3-(5,6-dihydro-4H-pyrrolo[3,2,1-ij]quinolin-1-yl)-4(1H-indol-3-yl) pyrrolidine-2,5-dione, and (−)-trans-3-(5,6-dihydro-4H-pyrrolo[3,2,1-ij]quinolin-1-yl)-4(1H-indol-3-yl)pyrrolidine-2, 5-dione. In a further preferred embodiment, the compound is (−)-trans-3-(5,6-dihydro-4H-pyrrolo[3,2,1-ij]quinolin-1-yl)-4(1H-indol-3-yl)pyrrolidine-2,5-dione.

The present invention also provides for pyrroloquinolinyl-pyrrole-2,5-dione compounds of formula IIIa and their synthesis.

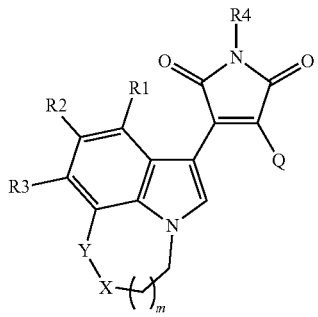
(IIIa)

where:

R1, R2 and R3 are independently selected from the group consisting of hydrogen, F, Cl, Br, I, —NR5R6, —($C_1$-$C_6$) alkyl, —($C_1$-$C_6$) substituted alkyl, —($C_3$-$C_9$) cycloalkyl, —($C_3$-$C_9$) substituted cycloalkyl, —O—($C_1$-$C_6$) alkyl, —O—($C_1$-$C_6$) substituted alkyl, —O—($C_3$-$C_9$) cycloalkyl, and —O—($C_3$-$C_9$) substituted cycloalkyl, aryl, heteroaryl, heterocyclyl;

R4 is independently selected from the group consisting of hydrogen, —($C_1$-$C_6$) alkyl, —$CH_2$R7;

R5, R6 are independently selected from the group consisting of hydrogen, and —($C_1$-$C_6$) alkyl;

R7 is independently selected from the group consisting of —O—P(=O)(OH)$_2$, —O—P(=O)(—OH)(—O—($C_1$-$C_6$) alkyl), —O—P(=O)(—O—($C_1$-$C_6$) alkyl)$_2$, —O—P(=O)(—OH)(—O—($CH_2$)-phenyl), —O—P(=O)(—O—($CH_2$)-phenyl)$_2$, a carboxylic acid group, an amino carboxylic acid group and a peptide;

Q is selected from the group consisting of aryl, heteroaryl, —O-aryl, —S-aryl, —O-heteroaryl, and —S-heteroaryl, provided that when R4 is hydrogen, ($C_3$-$C_4$) cycloalkyl, or ($C_1$-$C_4$) alkyl, Q is not 3-indolyl or substituted 3-indolyl;

X is selected from the group consisting of —($CH_2$)—, —(NR8)-, S, and O;

R8 is independently selected from the group consisting of hydrogen, —($C_1$-$C_6$) alkyl, —($C_1$-$C_6$) substituted alkyl, —($C_3$-$C_9$) cycloalkyl, —($C_3$-$C_9$) substituted cycloalkyl, —O—($C_1$-$C_6$) alkyl, —C(=O)—O—($C_1$-$C_6$) alkyl and —C(=O)—O—($C_1$-$C_6$) substituted alkyl;

Y is selected from the group consisting of —($CH_2$)— or a bond;

wherein said aryl, heteroaryl, —O-aryl, —S-aryl, —O-heteroaryl, and —S-heteroaryl groups may be substituted with one or more substituents independently selected from the group consisting of F, Cl, Br, I, —$NR_5R_6$, —($C_1$-$C_6$) alkyl, —($C_1$-$C_6$) substituted alkyl, —($C_3$-$C_9$) cycloalkyl, —($C_3$-$C_9$) substituted cycloalkyl, —O—($C_1$-$C_6$) alkyl, —O—($C_1$-$C_6$) substituted alkyl, —O—($C_3$-$C_9$) cycloalkyl, —O—($C_3$-$C_9$) substituted cycloalkyl, -aryl, -aryl-($C_1$-$C_6$) alkyl, -aryl-O—($C_1$-$C_6$) alkyl, —O-aryl, —O—($C_1$-$C_4$) alkyl-aryl, heteroaryl, heterocyclyl, —O—($C_1$-$C_4$) alkyl-heterocycle, and —(S(=O)$_2$)—($C_1$-$C_6$) alkyl; and m is 1 or 2.

The present invention also provides a pharmaceutical composition comprising one or more compounds of formula IIIa, IVa, IVb, Va, or Vb, and one or more pharmaceutically acceptable carriers or excipients. The present invention also provides a pharmaceutical composition comprising a compound of formula IIIa, IVa, IVb, Va, or Vb, and one or more pharmaceutically acceptable carriers or excipients.

The present invention provides a method of treating a cell proliferative disorder, said method comprising administering to a subject in need thereof a therapeutically effective amount of a compound of formula IIIa, IVa, IVb, Va, or Vb, or a pharmaceutically acceptable salt thereof, or a prodrug, metabolite, analog or derivative thereof, in combination with a pharmaceutically acceptable carrier, wherein said cell proliferative disorder is treated.

In an embodiment, the cell proliferative disorder is cancer.

In a preferred embodiment, the compound is selected from the group consisting of (+)-cis-3-(5,6-dihydro-4H-pyrrolo[3,2,1-ij]quinolin-1yl)-4(1H-indol-3-yl)pyrrolidine-2,5-dione, (−)-cis-3-(5,6-dihydro-4H-pyrrolo[3,2,1-ij]quinolin-1yl)-4(1H-indol-3-yl)pyrrolidine-2,5-dione, (+)-trans-3-(5,6-dihydro-4H-pyrrolo[3,2,1-ij]quinolin-1-yl)-4(1H-indol-3-yl)pyrrolidine-2,5-dione, and (−)-trans-3-(5,6-dihydro-4H-pyrrolo[3,2,1-ij]quinolin-1-yl)-4(1H-indol-3-yl)pyrrolidine-2,5-dione; or a pharmaceutically acceptable salt thereof or a prodrug, metabolite, analog or derivative thereof.

The present invention also provides a method of modulating an activity of c-Met comprising contacting a cell with an effective amount of a compound of formula IIa, IVa, IVb, Va, or Vb, or a pharmaceutically acceptable salt thereof, or a prodrug, metabolite, analog or derivative thereof, wherein said contacting results in said modulating an activity of c-Met.

In an embodiment, the modulating is inhibiting.

In an embodiment, the compound modulating the activity of c-Met, without significantly modulating said activity of Protein Kinase C.

The present invention also provides a method of selectively inhibiting an activity of c-Met, without inhibiting an activity of Protein Kinase C, comprising contacting a cell with an effective amount of a compound of formula IIIa, IVa, IVb, Va, or Vb, or a pharmaceutically acceptable salt thereof, or a prodrug, metabolite, analog or derivative thereof, wherein said contacting results in said selectively inhibiting said activity of c-Met, without inhibiting said activity of Protein Kinase C.

The present invention also provides a method of selectively inducing cell death in precancerous cells or cancer cells, comprising contacting a cell with an effective amount of a compound of formula IIIa, IVa, IVb, Va, or Vb, or a pharmaceutically acceptable salt thereof, or a prodrug, metabolite, analog or derivative thereof, wherein said contacting results in said selectively inducing cell death in said precancerous cells or said cancer cells.

The present invention further provides a method of treating cancer comprising selectively modulating an activity of c-Met, or both, without significantly modulating an activity of Protein Kinase C.

The present invention further provides a method of screening for a candidate compound for treating cancer, comprising contacting a cell with a candidate compound, measuring the activity of c-Met, measuring the activity of Protein Kinase C, and selecting a candidate compound that is capable of selectively inhibiting the activity of c-Met, without significantly inhibiting the activity of Protein Kinase C, wherein said candidate compound that is capable of selectively inhibiting the activity of c-Met, without significantly inhibiting the activity of Protein Kinase C, is a candidate compound for treating cancer. In an embodiment, the Protein Kinase C activity is measured in vitro.

Other features and advantages of the present invention are apparent from the additional descriptions provided herein including the different examples. The provided examples illustrate different components and methodology useful in practicing the present invention. The examples do not limit the claimed invention. Based on the present disclosure the skilled artisan can identify and employ other components and methodology useful for practicing the present invention.

quinolin-1-yl)-4(1H-indol-3-yl)pyrrolidine-2,5-dione, administered individually at 80 mg/kg, on the growth of xenografted MDA-MB-231 human breast cancer tumors in athymic female mice.

Figure 8:
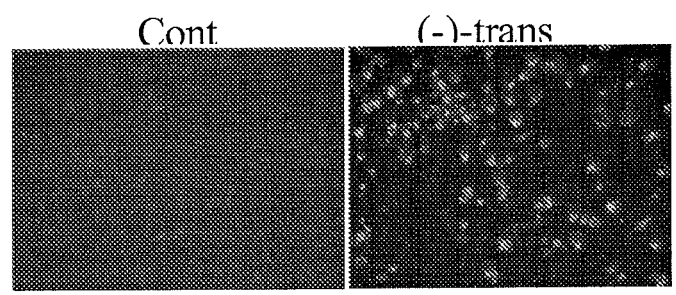

FIG. 8 sets forth an effect of (−)-trans-3-(5,6-dihydro-4H-pyrrolo[3,2,1-ij]quinolin-1-yl)-4(1H-indol-3-yl)pyrrolidine-2,5-dione to induce apoptosis in cancer cells.

Figure 9:
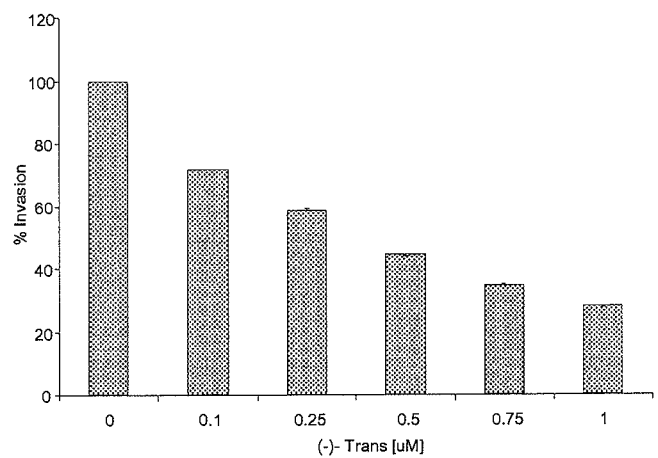

FIG. 9 sets forth an effect of (−)-trans-3-(5,6-dihydro-4H-pyrrolo[3,2,1-ij]quinolin-1-yl)-4(1H-indol-3-yl)pyrrolidine-2,5-dione to inhibit metastatic cancer cell invasion.

Figure 10:
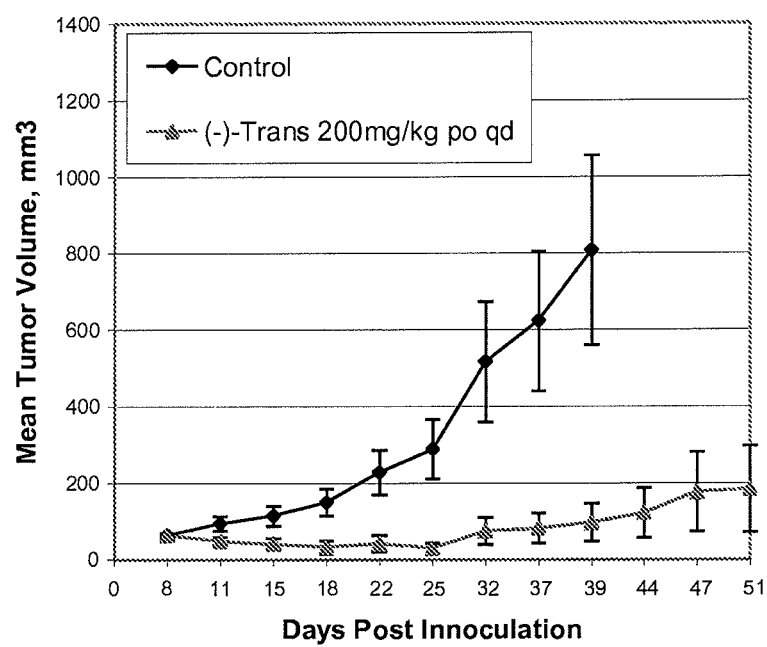

FIG. 10 sets forth an effect of (−)-trans-3-(5,6-dihydro-4H-pyrrolo[3,2,1-ij]quinolin-1-yl)-4(1H-indol-3-yl)pyrrolidine-2,5-dione on breast cancer xenograft model.

Figure 11:
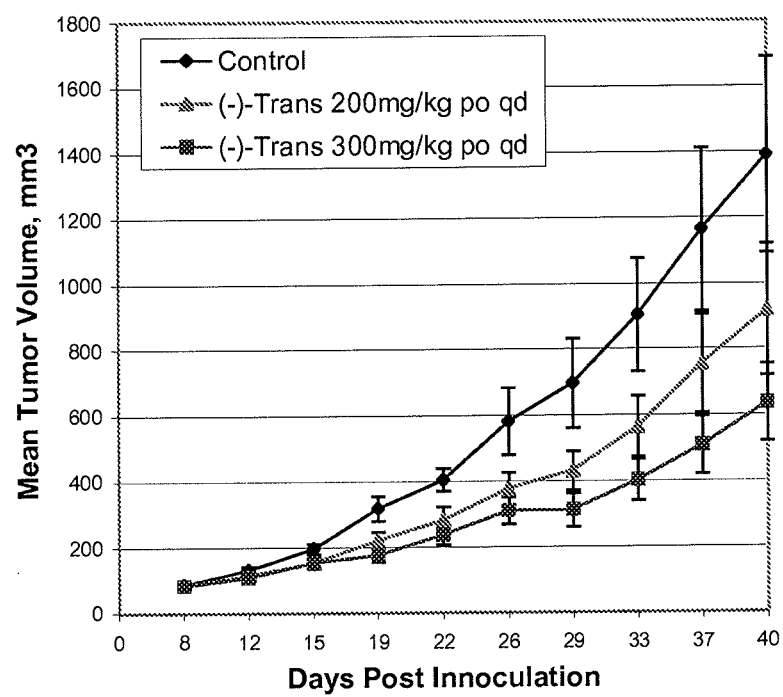

FIG. 11 sets forth an effect of (−)-trans-3-(5,6-dihydro-4H-pyrrolo[3,2,1-ij]quinolin-1-yl)-4(1H-indol-3-yl)pyrrolidine-2,5-dione on colon cancer xenograft model.

Figure 12:
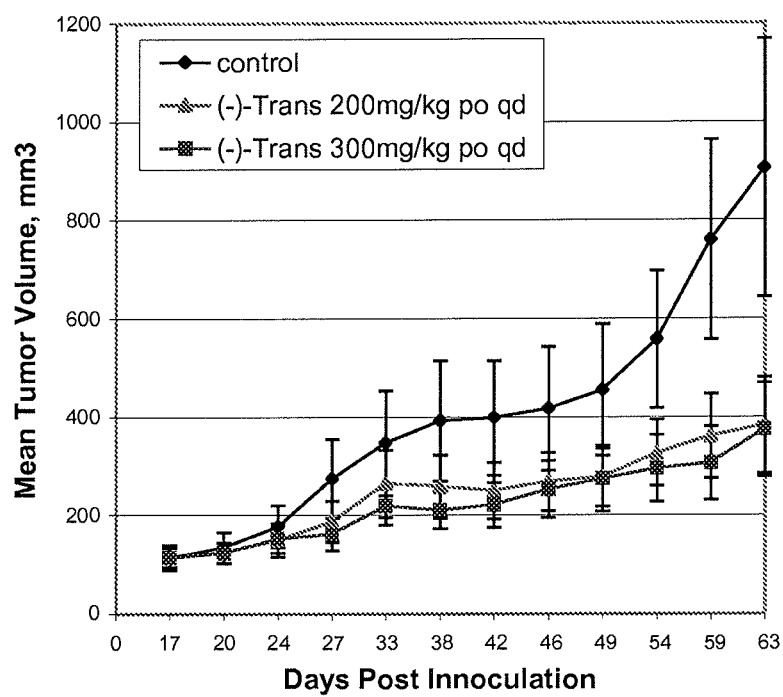

FIG. 12 sets forth an effect of (−)-trans-3-(5,6-dihydro-4H-pyrrolo[3,2,1-ij]quinolin-1-yl)-4(1H-indol-3-yl)pyrrolidine-2,5-dione on pancreatic cancer xenograft model.

DETAILED DESCRIPTION OF THE INVENTION

1. Pyrroloquinolinyl-pyrrole-2,5-diones and pyrroloquinolinyl-pyrrolidine-2,5-diones The present invention provides for pyrroloquinolinyl-pyrrole-2,5-dione compounds of formula III and IIIa and their synthesis

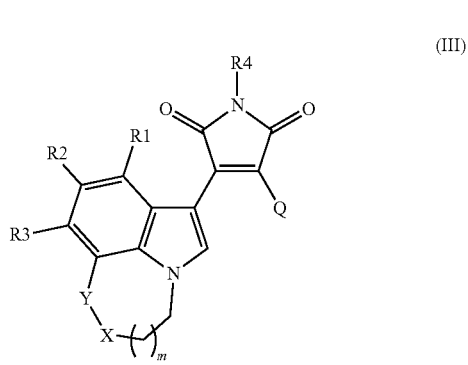

where:

R1, R2 and R3 are independently selected from the group consisting of hydrogen, F, Cl, Br, I, —NR5R6, —($C_1$-$C_6$) alkyl, —($C_1$-$C_6$) substituted alkyl, —($C_3$-$C_9$) cycloalkyl, —($C_3$-$C_9$) substituted cycloalkyl, —O—($C_1$-$C_6$) alkyl, —O—($C_1$-$C_6$) substituted alkyl, —O—($C_3$-$C_9$) cycloalkyl, and —O—($C_3$-$C_9$) substituted cycloalkyl, aryl, heteroaryl, heterocyclyl;

R4 is independently selected from the group consisting of hydrogen, —($C_1$-$C_6$) alkyl, —CH$_2$R7;

R5, R6 are independently selected from the group consisting of hydrogen, and —($C_1$-$C_6$) alkyl;

R7 is independently selected from the group consisting of —O—P(=O)(OH)$_2$, —O—P(=O)(—OH)(—O—($C_1$-$C_6$) alkyl), —O—P(=O)(—O—($C_1$-$C_6$) alkyl)$_2$, —O—P(=O)(—OH)(—O—(CH$_2$)-phenyl), —O—P(=O)(—O—(CH$_2$)-phenyl)$_2$, a carboxylic acid group, an amino carboxylic acid group and a peptide;

Q is selected from the group consisting of aryl, heteroaryl, —O-aryl, —S-aryl, —O-heteroaryl, and —S-heteroaryl;

X is selected from the group consisting of —(CH$_2$)—, —(NR8)-, S, and O;

R8 is independently selected from the group consisting of hydrogen, —($C_1$-$C_6$) alkyl, —($C_1$-$C_6$) substituted alkyl, —($C_3$-$C_9$) cycloalkyl, —($C_3$-$C_9$) substituted cycloalkyl, and —O—($C_1$-$C_6$) alkyl, —C(=O)—O—($C_1$-$C_6$) alkyl and —C(=O)—O—($C_1$-$C_6$) substituted alkyl;

Y is selected from the group consisting of —(CH$_2$)— or a bond;

wherein said aryl, heteroaryl, —O-aryl, —S-aryl, —O-heteroaryl, and —S-heteroaryl groups may be substituted with one or more substituents independently selected from the group consisting of F, Cl, Br, I, —NR5R6, —($C_1$-$C_6$) alkyl, —($C_1$-$C_6$) substituted alkyl, —($C_3$-$C_9$) cycloalkyl, —($C_3$-$C_9$) substituted cycloalkyl, —O—($C_1$-$C_6$) alkyl, —O—($C_1$-$C_6$) substituted alkyl, —O—($C_3$-$C_9$) cycloalkyl, —O—($C_3$-$C_9$) substituted cycloalkyl, -aryl, -aryl-($C_1$-$C_6$) alkyl, -aryl-O—($C_1$-$C_6$) alkyl, —O-aryl, —O—($C_1$-$C_4$) alkyl-aryl, heteroaryl, heterocyclyl, —O—($C_1$-$C_4$) alkyl-heterocycle, and —(S(=O)$_2$)—($C_1$-$C_6$) alkyl; and m is 1 or 2.

For the compound of formula IIIa, Q is selected from the group consisting of aryl, heteroaryl, —O-aryl, —S-aryl, —O-heteroaryl, and —S-heteroaryl, provided that when R4 is hydrogen, ($C_3$-$C_4$) cycloalkyl, or ($C_1$-$C_4$) alkyl, Q is not 3-indolyl or substituted 3-indolyl.

The present invention also provides for pyrroloquinolinyl-pyrrolidine-2,5-dione compounds of formula IVa, IVb, Va, or Vb, and methods of preparing the compounds of formulas IVa, IVb, Va, and Vb,

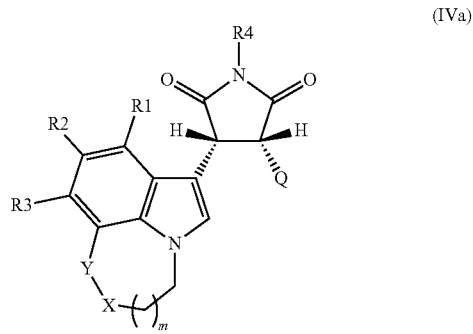

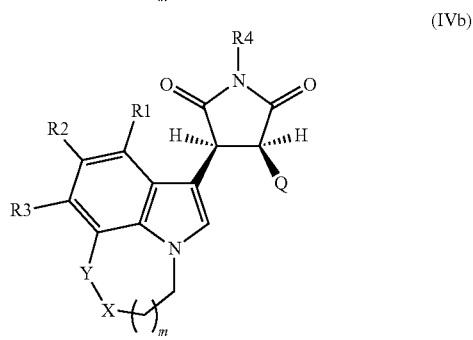

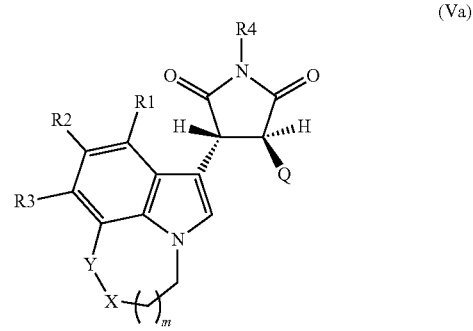

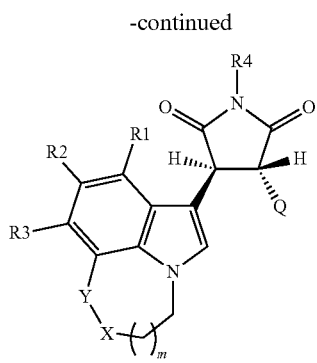

(Vb)

where:

R1, R2 and R3 are independently selected from the group consisting of hydrogen, F, Cl, Br, I, —NR5R6, —($C_1$-$C_6$) alkyl, —($C_1$-$C_6$) substituted alkyl, —($C_3$-$C_9$) cycloalkyl, —($C_3$-$C_9$) substituted cycloalkyl, —O—($C_1$-$C_6$) alkyl, —O—($C_1$-$C_6$) substituted alkyl, —O—($C_3$-$C_9$) cycloalkyl, and —O—($C_3$-$C_9$) substituted cycloalkyl, aryl, heteroaryl, heterocyclyl;

R4 is independently selected from the group consisting of hydrogen, —($C_1$-$C_6$) alkyl, —$CH_2$R7;

R5, R6 are independently selected from the group consisting of hydrogen, and —($C_1$-$C_6$) alkyl;

R7 is independently selected from the group consisting of —O—P(=O)(OH)$_2$, —O—P(=O)(—OH)(—O—($C_1$-$C_6$) alkyl), —O—P(=O)(—O—($C_1$-$C_6$) alkyl)$_2$, —O—P(=O)(—OH) (—O—(CH$_2$)-phenyl), —O—P(=O)(—O—(CH$_2$)-phenyl)$_2$, a carboxylic acid group, an amino carboxylic acid group and a peptide;

Q is selected from the group consisting of aryl, heteroaryl, —O-aryl, —S-aryl, —O-heteroaryl, and —S-heteroaryl;

X is selected from the group consisting of —(CH$_2$)—, —(NR8)-, S, and O;

R8 is independently selected from the group consisting of hydrogen, —($C_1$-$C_6$) alkyl, —($C_1$-$C_6$) substituted alkyl, —($C_3$-$C_9$) cycloalkyl, —($C_3$-$C_9$) substituted cycloalkyl, and —O—($C_1$-$C_6$) alkyl, —C(=O)—O—($C_1$-$C_6$) alkyl and —C(=O)—O—($C_1$-$C_6$) substituted alkyl;

Y is selected from the group consisting of —(CH$_2$)— or a bond;

wherein said aryl, heteroaryl, —O-aryl, —S-aryl, —O-heteroaryl, and —S-heteroaryl groups may be substituted with one or more substituents independently selected from the group consisting of F, Cl, Br, I, —NR5R6, —($C_1$-$C_6$) alkyl, —($C_1$-$C_6$) substituted alkyl, —($C_3$-$C_9$) cycloalkyl, —($C_3$-$C_9$) substituted cycloalkyl, —O—($C_1$-$C_6$) alkyl, —O—($C_1$-$C_6$) substituted alkyl, —O—($C_3$-$C_9$) cycloalkyl, —O—($C_3$-$C_9$) substituted cycloalkyl, -aryl, -aryl-($C_1$-$C_6$) alkyl, -aryl-O—($C_1$-$C_6$) alkyl, —O-aryl, —O—($C_1$-$C_4$) alkyl-aryl, heteroaryl, heterocyclyl, —O—($C_1$-$C_4$) alkyl-heterocycle, and —(S(=O)$_2$)—($C_1$-$C_6$) alkyl; and m is 1 or 2.

1.1. Definitions

The term "alkyl" refers to radicals containing carbon and hydrogen, without unsaturation. Alkyl radicals can be straight or branched. Exemplary alkyl radicals include, without limitation, methyl, ethyl, propyl, isopropyl, hexyl, t-butyl, sec-butyl and the like. Akyl groups may be denoted by a range, thus, for example, a ($C_1$-$C_6$) alkyl group is an alkyl group having from one to six carbon atoms in the straight or branched alkyl backbone. Substituted and unsubstituted alkyl groups may independently be ($C_1$-$C_5$) alkyl, ($C_1$-$C_6$) alkyl, ($C_1$-$C_{10}$) alkyl, ($C_3$-$C_{10}$) alkyl, or ($C_5$-$C_{10}$) alkyl. Unless expressly stated, the term "alkyl" does not include "cycloalkyl."

A "cycloalkyl" group refers to a cyclic alkyl group having the indicated number of carbon atoms in the "ring portion," where the "ring portion" may consist of one or more ring structures either as fused, spiro, or bridged ring structures. For example, a C3 to C6 cycloalkyl group (e.g., ($C_3$-$C_6$) cycloalkyl) is a ring structure having between 3 and 6 carbon atoms in the ring. When no range is given, then cycloalkyl has between three and nine carbon atoms (($C_3$-$C_9$) cycloalkyl) in the ring portion. Exemplary cycloalkyl groups include, but are not limited to cyclopropyl, cyclobutyl, cyclopentyl, cyclohexyl, cycloheptyl, and adamantyl. Preferred cycloalkyl groups have three, four, five, six, seven, eight, nine, or from three to nine carbon atoms in the ring structure.

The term substituted alkyl and substituted cycloalkyl, refer to alkyl and cycloalkyl groups, as defined above, substituted with one or more substituents independently selected from the group consisting of fluorine, aryl, heteroaryl, —O—($C_1$-$C_6$) alkyl, and —NR5R6, where R5 and R6 are independently selected from the group consisting of hydrogen and —($C_1$-$C_6$) alkyl.

The term "aryl" refers to an aromatic carbocyclic group, having one, two, or three aromatic rings. Exemplary aryl groups include, without limitation, phenyl, naphthyl, and the like. Aryl groups include one, two, or three aromatic rings structures fused with one or more additional nonaromatic carbocyclic or hetercyclic rings having from 4-9 members. Examples of fused aryl groups include benzocyclobutanyl, indanyl, tetrahydronapthylenyl, 1,2,3,4-tetrahydrophenanthrenyl, tetrahydroanthracenyl, 1,4-dihydro-1,4-methanonaphthalenyl, benzodioxolyl.

The term "heteroaryl" refers to a heteroaromatic (heteroaryl) group having one, two, or three aromatic rings containing from 1-4 heteroatoms (such as nitrogen, sulfur, or oxygen) in the aromatic ring. Heteroaryl groups include one, two, or three aromatic rings structures containing from 1-4 heteroatoms fused with one or more additional nonaromatic rings having from 4-9 members. Heteroaryl groups containing a single type of heteroatom in the aromatic ring are denoted by the type of hetero atom they contain, thus, nitrogen-containing heteroaryl, oxygen-containing heteroaryl and sulfur-containing heteroaryl denote heteroaromatic groups containing one or more nitrogen, oxygen or sulfur atoms respectively. Exemplary heteroaryl groups include, without limitation, pyridyl, pyrimidinyl, triazolyl, quinolyl, quinazolinyl, thiazolyl, benzo[b]thiophenyl, furanyl, imidazolyl, indolyl, and the like.

The terms "heterocyclyl" or "heterocycle" refers to either saturated or unsaturated, stable non-aromatic ring structures that may be fused, spiro or bridged to form additional rings. Each heterocycle consists of one or more carbon atoms and from one to four heteroatoms selected from the group consisting of nitrogen, oxygen and sulfur. "Heterocyclyl" or "heterocycle" include stable non-aromatic 3-7 membered monocyclic heterocyclic ring structures and 8-11 membered bicyclic heterocyclic ring structures. A heterocyclyl radical may be attached at any endocyclic carbon or nitrogen atom that results in the creation of a stable structure. Preferred heterocycles include 3-7 membered monocyclic heterocycles (more preferably 5-7-membered monocyclic heterocycles) and 8-10 membered bicyclic heterocycles. Examples of such groups include piperidinyl, piperazinyl, pyranyl, pyrrolidinyl, morpholinyl, thiomorpholinyl, oxopiperidinyl, oxopyrrolidinyl, oxoazepinyl, azepinyl, isoxozolyl, tetrahydropyranyl, tetrahydrofuranyl, dioxolyl, dioxinyl, oxathiolyl, dithiolyl, sulfolanyl, dioxanyl, dioxolanyl, tetrahydrofurodihydrofuranyl, tetrahydropyranodihydro-furanyl, dihydropyranyl, tetrahydrofurofuranyl, tetrahydropyranofuran, quinuclidinyl (1-azabicyclo[2.2.2]octanyl) and tropanyl (8-methyl-8-azabicyclo[3.2.1]octanyl).

For the purpose of the Q substituent, the term "substituted 3-indolyl" refers to a 3-indolyl group substituted with one or more substituents selected from the group consisting of: F, Cl, Br, I, —NR5R6, —($C_1$-$C_6$) alkyl, —($C_1$-$C_6$) substituted alkyl, —($C_3$-$C_9$) cycloalkyl, —($C_3$-$C_9$) substituted cycloalkyl, —O—($C_1$-$C_6$) alkyl, —O—($C_1$-$C_6$) substituted alkyl, —O—($C_3$-$C_9$) cycloalkyl, —O—($C_3$-$C_9$) substituted cycloalkyl, -aryl, -aryl-($C_1$-$C_6$) alkyl, -aryl-O—($C_1$-$C_6$) alkyl, —O-aryl, —O—($C_1$-$C_4$) alkyl-aryl, heteroaryl, heterocyclyl, —O—($C_1$-$C_4$) alkyl-heterocycle, and —(S(=O)$_2$)—($C_1$-$C_6$) alkyl; where R5, R6 are independently selected from the group consisting of hydrogen, and —($C_1$-$C_6$) alkyl.

For the purposes of the R7 substituent, the term "carboxylic acid group" refers to a group of the form —O—C(=O)—($C_1$-$C_6$) alkyl, —O—C(=O)—($C_3$-$C_9$) cycloalkyl, —O—C(=O)-aryl, —O—C(=O)-heteroaryl, —O—C(=O)-heterocycle, —O—C(=O)—($C_1$-$C_6$) alkyl-aryl, —O—C(=O)—($C_1$-$C_6$) alkyl-heteroaryl, or —O—C(=O)—($C_1$-$C_6$) alkyl-heterocycle. Included in "carboxylic acid group" are groups of the form —O—C(=O)—($C_1$-$C_6$) alkyl, —O—C(=O)—($C_3$-$C_9$) cycloalkyl, —O—C(=O)-aryl, —O—C(=O)-heteroaryl, —O—C(=O)-heterocycle, —O—C(=O)—($C_1$-$C_6$) alkyl-aryl, —O—C(=O)—($C_1$-$C_6$) alkyl-heteroaryl, or —O—C(=O)—($C_1$-$C_6$) alkyl-heterocycle substituted with one or more substituent independently selected from the group consisting of: F, Cl, Br, I, —OH, —SH, —NR5R6, —($C_1$-$C_6$) alkyl, —($C_1$-$C_6$) substituted alkyl, —($C_3$-$C_9$) cycloalkyl, —($C_3$-$C_9$) substituted cycloalkyl, —O—($C_1$-$C_6$) alkyl, —O—($C_1$-$C_6$) substituted alkyl, —S—($C_1$-$C_6$) alkyl, —O—($C_3$-$C_9$) cycloalkyl, —O—($C_3$-$C_9$) substituted cycloalkyl, -aryl, —O-aryl, —O—($C_1$-$C_4$) alkyl-aryl, heteroaryl, heterocyclyl, —O—($C_1$-$C_4$) alkyl-heterocycle, —(S(=O)$_2$)—($C_1$-$C_6$) alkyl, —NH—C(=NH)—NH$_2$ (i.e., guanido), —COOH, and —C(=O)—NR5R6, where R5 and R6 are independently selected from the group consisting of hydrogen, and —($C_1$-$C_6$) alkyl. In addition, for the purposes of the R7 substituent the term "amino carboxylic acid group" refers to a carboxylic acid group, including carboxylic acid groups substituted with one or more of the above-stated substituents, which bears one or more independently selected amino groups of the form —NR5R6 where R5 and R6 are independently selected from the group consisting of hydrogen and (C1-C6) alkyl.

In one embodiment of this invention, R7 is an alpha amino or imino acid, including but not limited to alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine or stereoisomers or racemic mixtures thereof. In another embodiment the of the invention R7 is alpha amino or imino acid selected from the group consisting of L-alanine, L-arginine, L-asparagine, L-aspartic acid, L-cysteine, L-glutamine, L-glutamic acid, L-glycine, L-histidine, L-isoleucine, L-leucine, L-lysine, L-methionine, L-phenylalanine, L-proline, L-serine, L-threonine, L-tryptophan, L-tyrosine, L-valine.

For the purposes of the R7 substituent, the term "peptide" refers to a dipeptide, tripeptide, tetrapeptide or pentapeptide, which release two, three, four, or five amino or imino acids (e.g., proline) respectively upon hydrolysis. For the purpose of R7, peptides are linked to the remainder of the molecule through an ester linkage. In one embodiment, peptides of R7 are comprised of alpha amino or imino acid, including but not limited to alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine or stereoisomers or racemic mixtures thereof; and in a more preferred version of this embodiment, the carboxyl group involved in the ester linkage is the carboxyl terminal COOH group of the peptide, as opposed to a side chain carboxyl. In another embodiment the of the invention R7 is alpha amino or imino acid selected from the group consisting of L-alanine, L-arginine, L-asparagine, L-aspartic acid, L-cysteine, L-glutamine, L-glutamic acid, L-glycine, L-histidine, L-isoleucine, L-leucine, L-lysine, L-methionine, L-phenylalanine, L-proline, L-serine, L-threonine, L-tryptophan, L-tyrosine, and L-valine; and in a more preferred version of this preferred embodiment, the carboxyl group involved in the ester linkage is the carboxyl terminal COOH group of the peptide, as opposed to a side chain carboxyl.

1.2. Preferred Compounds

Included in the preferred embodiments are compounds of formula III, IVa, IVb, Va, or Vb, wherein Q is selected from the group consisting of aryl, heteroaryl, —O-aryl, —S-aryl, —O-heteroaryl, and —S-heteroaryl, provided that Q is not 3-indolyl or a substituted 3-indolyl. In other preferred embodiments Q is selected from the group consisting of aryl, heteroaryl, —O-aryl, —S-aryl, —O-heteroaryl, and —S-heteroaryl, provided that when R4 is hydrogen, cycloalkyl, or alkyl, Q is not 3-indolyl or a substituted 3-indolyl. In still other preferred embodiments Q is selected from the group consisting of aryl, heteroaryl, —O-aryl, —S-aryl, —O-heteroaryl, and —S-heteroaryl, provided that when R4 is hydrogen, ($C_3$-$C_4$) cycloalkyl, or ($C_1$-$C_4$) alkyl, Q is not 3-indolyl or substituted 3-indolyl. In another preferred embodiment Q is 3-indolyl or a substituted 3-indolyl provided that R4 is not hydrogen, cycloalkyl, or alkyl. In still another preferred embodiment Q is 3-indolyl or a substituted 3-indolyl provided that R4 is not hydrogen, ($C_3$-$C_4$) cycloalkyl, or ($C_1$-$C_4$) alkyl.

Other preferred embodiments include compounds of formulas IIIa, IVa, IVb, Va, or Vb where R4 is —CH$_2$R7. These compounds may serve as prodrug forms of the corresponding compounds of formulas IIIa, IVa, IVb, Va, or Vb where R4 is H. The prodrug form is cleaved by hydrolysis to release the corresponding compound where R4 is H. The hydrolysis may occur by enzymatic or nonenzymatic routes that produce the corresponding hydroxymethylene derivative, which upon subsequent hydrolysis, result in the release of compounds where R4 is H. In one such preferred embodiment R4 is —CH$_2$R7, where R7 is —O—P(=O)(OH)$_2$, —O—P(=O)(—OH)(—O—($C_1$-$C_6$)alkyl), or —O—P(=O)(—O—($C_1$-$C_6$)alkyl)$_2$. In one embodiment where R7 is —O—P(=O)(—O—($C_1$-$C_6$)alkyl)$_2$, the alkyl groups are independently selected. In another preferred embodiment, R4 is —CH$_2$R7, where R7 is a carboxylic acid group or an amino carboxylic acid group. In still another preferred embodiment R7 is a peptide; where in a more preferred embodiment the peptide is linked through an ester bond formed with the carboxyl terminal COOH group of the peptide chain to the remainder of the compound. In other preferred separate and independent embodiments of compounds of formulas IIIa, IVa, IVb, Va, or Vb where R4 is —CH$_2$R7 and R7 is a peptide, the peptide may be a dipeptide, a tripeptide, a tetrapeptide or a pentapeptide. Preferred amino acid compositions for peptides of the R7 functionality are described above.

Embodiments of compounds of formulas III, IIIa, IVa, IVb, Va, or Vb include those where X is selected from the group consisting of —(NR8)-, S, and O, where R8 is independently selected from the group consisting of hydrogen, —(C$_1$-C$_6$) alkyl, —(C$_1$-C$_6$) substituted allyl, —(C$_3$-C$_9$) cycloalkyl, —(C$_3$-C$_9$) substituted cycloalkyl, and —O—(C$_1$-C$_6$) alkyl. Other embodiments of compounds of formulas III, IIIa, IVa, IVb, Va, or Vb include those where X is —CH$_2$—. In other embodiments of compounds of formulas III, IIIa, IVa, IVb, Va, or Vb, X is oxygen (O). In other embodiments of compounds of formulas III, IIIa, IVa, IVb, Va, or Vb, X is sulfur (S). In still other embodiments of compounds of formulas III, IIIa, IVa, IVb, Va, or Vb, X is —(NR8)-, where R8 is independently selected from the group consisting of hydrogen, —(C$_1$-C$_6$) alkyl, —(C$_1$-C$_6$) substituted alkyl, —(C$_3$-C$_9$) cycloalkyl, —(C$_3$-C$_9$) substituted cycloalkyl, and —O—(C$_1$-C$_6$) alkyl.

Other preferred embodiments of the invention include compounds of formula IIIa, where Q is a heteroaryl or an optionally substituted heteroaryl group. In four separate alternative preferred embodiments of compounds of formula IIIa, Q is an optionally substituted monocyclic heteroaryl group, an optionally substituted bicyclic heteroaryl group, an optionally substituted bicyclic heteroaryl group with the proviso that the bicyclic heteroaryl group is not an indolyl group or a substituted indolyl, or an optionally substituted tricyclic heteroaryl group. Optional substituents, when present, are independently selected from those recited for aryl, heteroaryl, —O-aryl, —S-aryl, —O-heteroaryl, and —S-heteroaryl.

Included in the preferred embodiments of the invention are compounds of formulas IVa, IVb, Va, or Vb, where Q is a heteroaryl or an optionally substituted heteroaryl group. In four separate alternative preferred embodiments of compounds of formulas IVa, IVb, Va, or Vb, Q is an optionally substituted monocyclic heteroaryl group, an optionally substituted bicyclic heteroaryl group, an optionally substituted bicyclic heteroaryl group with the proviso that the bicyclic heteroaryl group is not indolyl, or an optionally substituted tricyclic heteroaryl group. In a more preferred embodiment, Q is an optionally substituted nitrogen-containing heteroaryl group. In a related embodiment, Q is an optionally substituted indolyl. Optional substituents, when present are independently selected from those recited for aryl, heteroaryl, —O-aryl, —S-aryl, —O-heteroaryl, and —S-heteroaryl.

Preferred embodiments of the invention include mixtures of compounds of formulas IVa and IVb, including racemic mixtures. In another preferred embodiment, the compounds of formula IVa and IVb are the separate enantiomers of (±)-cis-3-(5,6-dihydro-4H-pyrrolo[3,2,1-ij]quinolin-1yl)-4(1H-indol-3-yl)pyrrolidine-2,5-dione. In this embodiment the preparation of (±)-cis-3-(5,6-dihydro-4H-pyrrolo[3,2,1-ij]quinolin-1yl)-4(1H-indol-3-yl)pyrrolidine-2,5-dione is prepared as a mixture beginning with the starting materials 1,2,3,4-tetrahydroquinoline and indole-3-acetamide. The 1,2,3,4-tetrahydroquinoline is converted into 5,6-dihydro-4H-pyrrolo[3,2,1-ij]quinolin-1-yl)oxoacetic acid methyl ester as described in Example 1, steps 1-5. The 5,6-dihydro-4H-pyrrolo[3,2,1-ij]quinolin-1-yl)oxoacetic acid methyl ester is reacted with indole-3-acetamide as described in Example 1, step 6, to yield 3-(5,6-dihydro-4H-pyrrolo[3,2,1-ij]quinolin-1yl)-4(1H-indol-3-yl)pyrrole-2,5-dione. The mixture of (±)-cis-3-(5,6-dihydro-4H-pyrrolo[3,2,1-ij]quinolin-1yl)-4(1H-indol-3-yl)pyrrolidine-2,5-dione is then prepared by catalytic hydrogenation as described in Example 2 using Procedure B.

Preferred embodiments of the invention also include mixtures of compounds of formulas Va and Vb, including racemic mixtures. In another preferred embodiment, the compounds of Va and Vb are the separate enantiomers of (±)-trans-3-(5,6-dihydro-4H-pyrrolo[3,2,1-ij]quinolin-1-yl)-4(1H-indol-3-yl)pyrrolidine-2,5-dione. In this embodiment, the compounds are prepared as a mixture by first preparing (±)-cis-3-(5,6-dihydro-4H-pyrrolo[3,2,1-ij]quinolin-1yl)-4(1H-indol-3-yl)pyrrolidine-2,5-dione, as described above. The mixture of cis compounds is then treated with a mixture of potassium tert-butoxide in tert-butanol to obtain a mixture of (±)-trans-3-(5,6-dihydro-4H-pyrrolo[3,2,1-ij]quinolin-1-yl)-4(1H-indol-3-yl)pyrrolidine-2,5-dione as described in Example 3.

All stereoisomers of the compounds of the instant invention are contemplated, either in admixture or in pure or substantially pure form, including crystalline forms of racemic mixtures and crystalline forms of individual isomers. The definition of the compounds according to the invention embraces all possible stereoisomers (e.g., the R and S configurations for each asymmetric center) and their mixtures. It very particularly embraces the racemic forms and the isolated optical isomers having a specified activity. The racemic forms can be resolved by physical methods, such as, for example, fractional crystallization, separation or crystallization of diastereomeric derivatives, separation by chiral column chromatography or supercritical fluid chromatography. The individual optical isomers can be obtained from the racemates by conventional methods, such as, for example, salt formation with an optically active acid followed by crystallization. Furthermore, all geometric isomers, such as E- and Z-configurations at a double bond, are within the scope of the invention unless otherwise stated. Certain compounds of this invention may exist in tautomeric forms. All such tautomeric forms of the compounds are considered to be within the scope of this invention unless otherwise stated. The present invention also includes one or more regioisomeric mixtures of an analog or derivative.

As used herein, the term "salt" is a pharmaceutically acceptable salt and can include acid addition salts including hydrochlorides, hydrobromides, phosphates, sulphates, hydrogen sulphates, alkylsulphonates, arylsulphonates, acetates, benzoates, citrates, maleates, fumarates, succinates, lactates, and tartrates; alkali metal cations such as Na$^+$, K$^+$, Li$^+$, alkali earth metal salts such as Mg or Ca, or organic amine salts.

As used herein, the term "metabolite" means a product of metabolism of a compound of the present invention, or a pharmaceutically acceptable salt, analog or derivative thereof, that exhibits a similar activity in vivo to said compound of the present invention.

As used herein, the term "prodrug" means a compound of the present invention covalently linked to one or more pro-moieties, such as an amino acid moiety or other water solubilizing moiety. A compound of the present invention may be released from the pro-moiety via hydrolytic, oxidative, and/or enzymatic release mechanisms. In an embodiment, a prodrug composition of the present invention exhibits the added benefit of increased aqueous solubility, improved stability, and improved pharmacokinetic profiles. The pro-moiety may be selected to obtain desired prodrug characteristics.

For example, the pro-moiety, e.g., an amino acid moiety or other water solubilizing moiety such as phosphate within R4, may be selected based on solubility, stability, bioavailability, and/or in vivo delivery or uptake.

2. The Synthesis of Pyrroloquinolinyl-pyrrole-2,5-diones and pyrroloquinolinyl-pyrrolidine-2,5-diones Standard synthetic methods and procedures for the preparation of organic molecules and functional group transformations and manipulations including the use of protective groups can be obtained from the relevant scientific literature or from standard reference textbooks in the field. Although not limited to any one or several sources, recognized reference textbooks of organic synthesis include: Smith, M. B.; March, J. March's Advanced Organic Chemistry: Reactions, Mechanisms, and Structure, $5^{th}$ ed.; John Wiley & Sons: New York, 2001; and Greene, T. W.; Wuts, P. G. M. Protective Groups in Organic Synthesis, $3^{rd}$; John Wiley & Sons: New York, 1999. The following descriptions of synthetic methods are designed to illustrate, but not limit, general procedures for the preparation of compounds of the invention.

2.1 General Procedures for the Synthesis of pyrroloquinolinyl-pyrrole-2,5-dione and pyrroloquinolinyl-pyrrolidine-2,5-diones where R4 is hydrogen The present invention provides for pyrroloquinolinyl-pyrrole-2,5-dione compounds of formula IIa, IVa, IVb, Va, or Vb. The preparation of compounds of formulas III, IIIa, IVa, IVb, Va, and Vb may be achieved by a series of reactions commencing with the reaction of a 5,6-dihydro-4H-pyrrolo[3,2,1-ij]quinolin-1-yl)oxoacetic acid ester of formula I with an amide of formula II, to form a 3-(5,6-dihydro-4H-pyrrolo[3,2,1-ij]quinolin-1 yl)-4(1H-indol-3-yl)pyrrole-2,5-dione of formula III, including compounds of formula IIa, where R4 is hydrogen, as shown in Scheme 1.

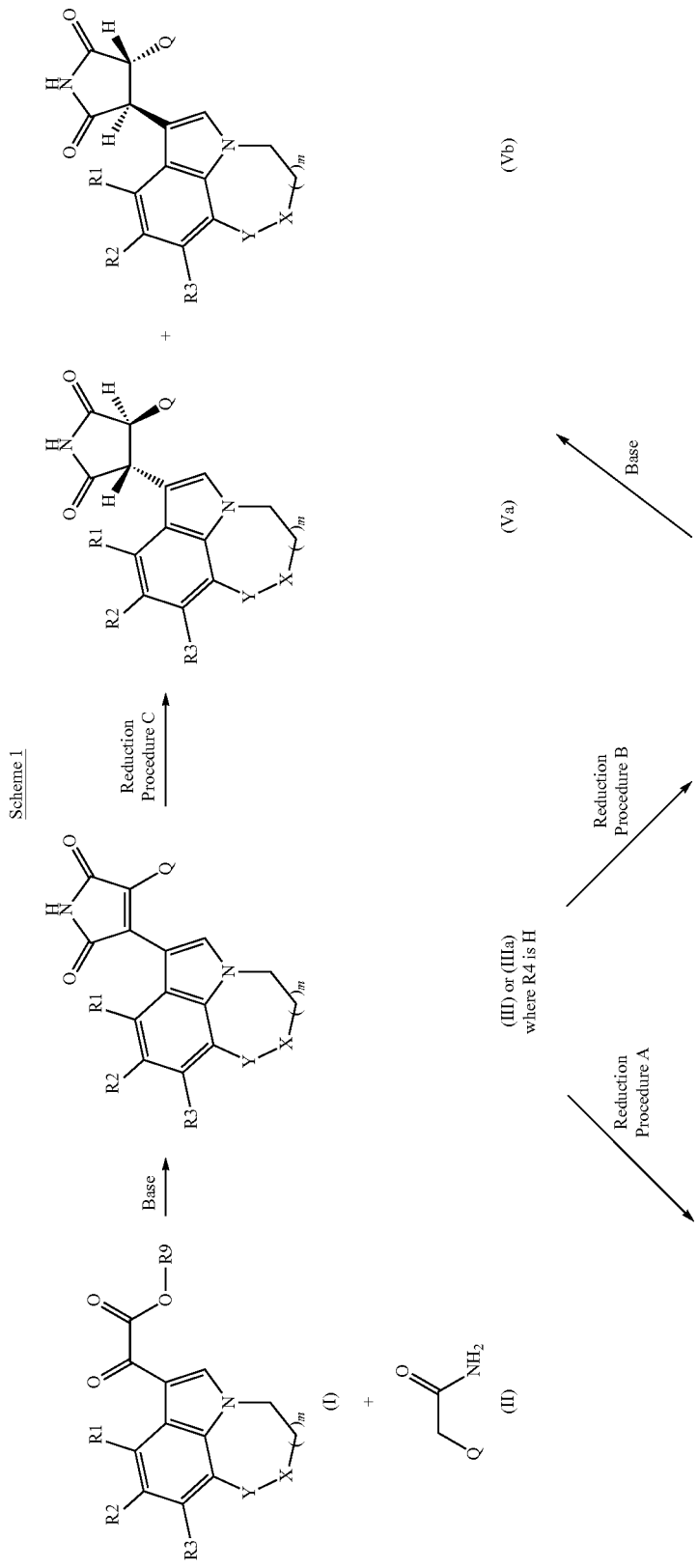

-continued
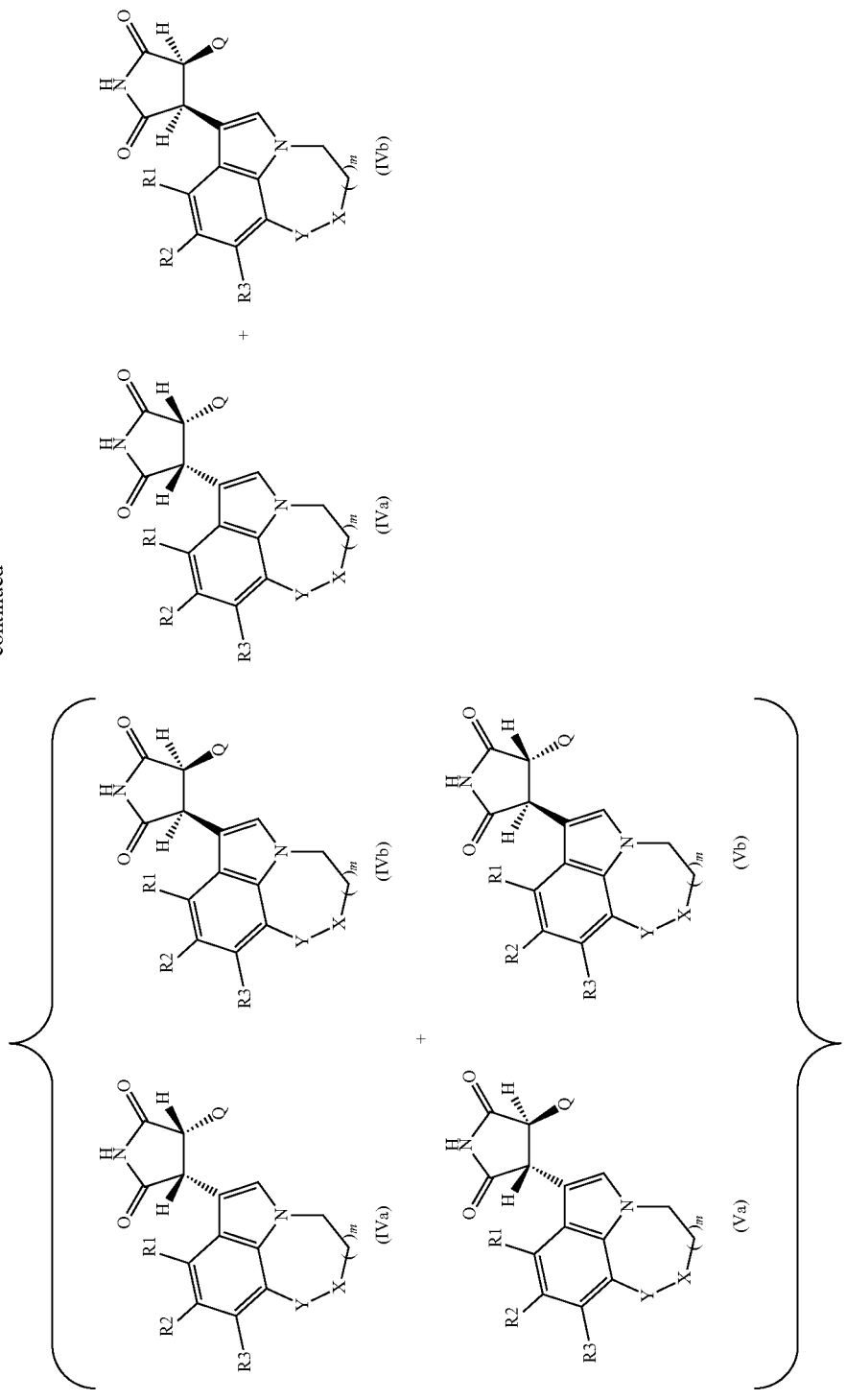

2.1.1. Synthesis of 3-(5,6-dihydro-4H-pyrrolo[3,2,1-ij]quinolin-1yl)-4(1H-indol-3-yl)pyrrole-2,5-diones of formula III where R4 is hydrogen The condensation of an ester of formula I and a compound of formula II to produce compounds of formula III, including compounds of formula IIIa, where R4 is hydrogen is conducted in any suitable anhydrous polar aprotic solvent including, but not limited to, tetrahydrofuran (THF), tetrahydropyran, diethyl ether and the like in the presence of base. For the purposes of the reaction, suitable esters of formula I include, but are not limited to, alkyl esters where R9 is a (C1-C4) alkyl group, and preferred esters include the methyl and ethyl esters. Suitable bases for the reaction include alkaline metal salts of low molecular weight alkyl alcohols, including, but not limited to, alkaline metal salts of methanol, ethanol, propanol, isopropanol, n-butanol, isobutanol, and tert-butanol. Preferred alkaline metal salts of low molecular weight alkyl alcohols include sodium and potassium salts, with potassium tert-butoxide (tBuOK) being the preferred base. Typically the reactions are conducted at 0° C. for 2 hours, however, both the time and temperature may be altered depending upon the specific substituents present on compounds of formula I and II, and the solvent employed. The reaction temperature may be varied from −78° C. to 37° C., and is preferably from −35° C. to 25° C., or more preferably from −15° C. to 10° C. Reaction times will generally vary inversely with the temperature employed, suitable times from about 15 minutes to 24 hours may be employed, more preferably, 30 minutes to 12 hours, and more preferably 1 to 6 hours.

2.1.2. Preparation of Compounds of Formulas IVa, IVb, Va and Vb where R4 is Hydrogen Reduction of compounds of formulas III and IIIa, where R4 is hydrogen to yield the corresponding 3-(5,6-dihydro-4H-pyrrolo[3,2,1-ij]quinolin-1yl)-4(1H-indol-3-yl)pyrrolidine-2,5-diones having formula IVa, IVb, Va, or Vb may be conducted employing a variety of procedures including, but not limited to, reduction with zinc-mercury (Procedure A), catalytic hydrogenation (Procedure B), and reduction with magnesium in methanol (Procedure C). As indicated in Scheme 1, depending on the reduction reaction and conditions chosen, the reaction will yield principally compounds of formulas IVa and IVb, or principally compounds of formulas Va and Vb, or alternatively a mixture of compounds of formulas IVa, IVb, Va, and Vb.

Mixtures of compounds of formulas IVa, IVb, Va, and Vb may be prepared by the direct reduction of compounds of formulas III or IIIa with a zinc-mercury reducing agent. The reaction is generally carried out with fresh reducing agent prepared by mixing Zn powder with $HgCl_2$ deionized water followed by acidification with HCl. After drying, the solid reducing agent (zinc-mercury) is suitable for reduction of compounds of formulas III or IIIa in refluxing dry ethanol under a dry HCl gas atmosphere as described in Example 2, Procedure A, for the reduction of 3-(5,6-dihydro-4H-pyrrolo[3,2,1-ij]quinolin-1-yl)-4(1H-indol-3-yl)pyrrole-2,5-dione.

An alternative method of preparing pyrrolidine-2,5-diones is catalytic hydrogenation, which yields a mixture consisting principally of the (±)-cis pyrrolidine-2,5-diones of formulas IVa and IVb. Catalytic hydrogenation of compounds of formulas III or IIIa may be conducted in an anhydrous alcohol over a noble metal catalyst under 1 atmosphere of hydrogen for 48 hours. A variety of low molecular weight alkyl alcohols may be employed to conduct the reduction, including n-propyl alcohol, isopropyl alcohol, ethanol or methanol. Preferably the alcohol is ethanol or methanol, and most preferably methanol. A noble metal catalyst (e.g., platinum, palladium, rhodium, ruthenium etc.) on charcoal is preferred for the reduction of compounds of formulas III or IIIa. In more preferred embodiments, the noble metal catalyst is palladium on activated charcoal. While reduction compounds of formulas IIIa or III under 1 atmosphere of hydrogen at room temperature (25° C.) for 12-48 hours is generally suitable for preparation of pyrrolidine-2,5-diones, the pressure of hydrogen, reaction time, and the reaction temperature may be varied. Catalytic hydrogenation of 3-(5,6-dihydro-4H-pyrrolo[3,2,1-ij]quinolin-1-yl)-4(1H-indol-3-yl)pyrrole-2,5-dione is described in Example 2, Procedure B.

Pyrrole-2,5-diones of formula IIIa or III may be reduced to yield a mixture of compounds of formulas Va and Vb by the reduction in anhydrous alcohol with a metal reducing agent. Preferred metals include sodium, calcium and magnesium, with magnesium as a more preferred metal reducing agent. The reaction is typically carried out under an inert atmosphere of nitrogen for 30 minutes to 2 hours by refluxing a compound of formula III or formula IIIa in an alcohol selected from the group consisting of methanol, ethanol, n-propanol, and isopropanol with magnesium turnings. In preferred embodiments the reaction is conducted for about 40 minutes in methanol as described in Example 2, Procedure C, for the preparation of (±)-trans-3-(5,6-dihydro-4H-pyrrolo[3,2,1-ij]quinolin-1-yl)-4(1H-indol-3-yl)pyrrolidine-2,5-dione.

Compounds of IVa and/or IVb, which have the pyrrolidine ring substituents in the cis configuration, may be converted into a mixture of compounds of Va and Vb, where the substituents are in the trans configuration, or into a mixture of all four isomers of formulas IVa, IVb, Va, and Vb by treatment with base in a polar protic solvent. Typically the reaction employs an alkaline metal salt of a (C1-C4) alkyl alcohol in an alcohol solvent (e.g., sodium or potassium methoxide in methanol, sodium or potassium ethoxide in ethanol, sodium or potassium tert-butoxide in tert-butanol), with potassium tert-butoxide in tert-butanol as the preferred alkaline metal salt and solvent mixture. Reactions are generally conducted from 0° C. to the reflux temperature of the reaction mixture for 4 to 48 hours. In more preferred embodiments, the reaction are conducted from room temperature (25° C.) to the reflux temperature of the mixture for 8 to 24 hours, and in an even more preferred embodiment, the reaction is conducted at about 50° C. in a mixture of potassium tert-butoxide in tert-butanol for about 16 hours. Short reaction times and low temperatures favor formation of mixtures still containing compounds IVa and/or IVb.

2.1.3. Introduction of Aryl or Heteroaryl Substituents into Compounds of III, IIIa, IVa, IVb, Va, and Vb The introduction of additional substituted and unsubstituted aryl or heteroaryl substituents on to aromatic rings of compounds of formulas III, IIIa, IVa, IVb, Va, or Vb may be accomplished by the reaction of a substituted or unsubstituted aryl or heteroaryl boronic acid with an aromatic halogen substituent on a compound of formula III, IIIa, IVa, IVb, Va, or Vb. The reaction is typically carried out by heating a mixture of a compound of formula III, IIIa, IVa, IVb, Va, or Vb bearing an aryl or heteroaryl bromide or iodide, more preferably an arylbromide or hetroarylbromide, with an aryl or heteroaryl boronic acid in the presence of tetrakistriphenylphosphine palladium in a solvent mixture consisting of 5 parts toluene, 5 parts ethanol, 1 part saturated NaHCO$_3$, and 2 parts water to 100° C. under nitrogen for 5 hours. After cooling to room temperature, the mixture is extracted with ethyl acetate and concentrated. The residue is purified by silica gel chromatography. In a preferred embodiment, the halogenated compound of formula III, IIIa, IVa, IVb, Va, or Vb bears the halogen on an aryl or heteroaryl group Q functionality resulting in the introduction of substituted aryl or heteroaryl group donated by the boronic acid on to the Q substituent. In a more preferred embodiment, the Q functionality is a brominated aromatic or heteroaromatic Q functionality. In another more preferred embodiment the halogenated Q functionality reacted with the boronic acid is a halogenated 3-indolyl. Examples 31-34 describe the introduction of substituted and unsubstituted aromatic groups into compounds of formula Va and Vb employing a brominated Q functionality where Q is a brominated 3-indolyl.

Aromatic and heteroaromatic boronic acids including 2-thienylboronic acid, 3-thienylboronic acid, and 2-naphthylboronic acid are available from a variety of commercial sources including Sigma-Aldrich (St. Louis, Mo.). Alternatively aromatic and heteroaromatic boronic acids may be prepared from the corresponding aryl or heteroaryl bromides by reaction with triisopropyl borate in the presence of n-butyllithium followed by quenching with aqueous HCl. (See, e.g., W. Li, et. al., *J. Organic Chem.* 67: 5394-97 (2002) and C. M. Marson, et. al., Tetrahedron 59: 4377-81 (2003).

2.1.4. Preparation of Compounds of Formulas III, IIIa, IVa, IVb, Va, and Vb where R4 is —CH$_2$R7

Compounds of formula III, IIIa, IVa, IVb, Va, or Vb, where R4 is hydrogen, can be converted into compounds of formula III, IIIa, IVa, IVb, Va, or Vb where R4 is —CH$_2$R7. The conversion begins with the preparation of the hydroxymethylene derivative of the compounds as indicated in the partial structures shown in Scheme 2.

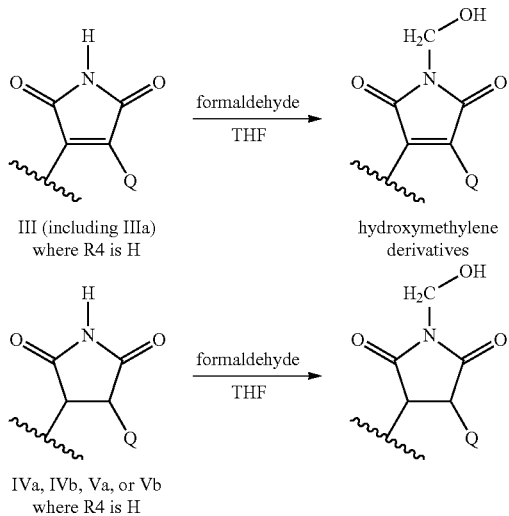

Scheme 2

Preparation of the hydroxymethylene derivatives is accomplished by reaction of a compound of formula III, IIIa, IVa, IVb, Va, or Vb where R4 is H with aqueous formaldehyde in tetrahydrofuran (THF). Typical reaction conditions employ equal volumes of THF and 37% formaldehyde in water with the reaction stirred for 14-16 hours at room temperature. Reaction times and temperatures may vary from 1 hour to 48 hours and the temperature may be from 0° C. to 50° C. or more preferably from 10° C. to 37° C. Upon completion the reaction is partitioned between water and an organic solvent, typically ethyl acetate. The organic layer is dried over sodium sulfate, concentrated, and subject to chromatography on silica gel as necessary to yield the hydroxymethylene product. The preparation of the hydroxymethylene derivative of 3-(5,6-dihydro-4H-pyrrolo[3,2,1-ij]quinolin-1-yl)-4(1H-indol-3-yl)pyrrolidine-2,5-dione, 3-(5,6-dihydro-4H-pyrrolo[3,2,1-ij]quinolin-1-yl)-1-hydroxymethyl-4-(1H-indol-3-yl)-pyrrolidine-2,5-dione, is described in Example 56, step 1.

Compounds of formulas III, IIIa, IVa, IVb, Va, or Vb where R4 is —CH$_2$R7 and R7 is phosphate (—O—P(=O)(OH)$_2$), monoalkyl phosphate (e.g., —O—P(=O)(—OH)(—O—(C$_1$-C$_6$) alkyl)), dialkyl phosphate (e.g., —O—P(=O)(—O—(C$_1$-C$_6$) alkyl)$_2$) a monobenzylphosphate ester (—O—P(=O)(—OH) (—O—(CH$_2$)-phenyl)), or a dibenzylphosphate ester (—O—P(=O)(—O—(CH$_2$)-phenyl)$_2$) may be prepared from the desired hydroxymethylene derivative and a suitably substituted phosphoric acid by any reaction suitable for the formation of a phosphate ester bond between the phosphoric acid compound and the hydroxymethylene derivative. In a preferred method, the formation of phosphate esters is conducted by reaction of a hydroxymethylene derivative of a compound of formula III, IIIa, IVa, IVb, Va, or Vb with a suitably protected phosphoramidate followed by deprotection. Reactions with the desired phosphoramidate are typically conducted at room temperature in anhydrous THF. Following the addition of the phosphoramidate, the reaction is treated with tetrazole (3% in acetonitrile) and stirred 5 minutes to 1 hour, after which the reaction is cooled to −78° C. The cooled reaction is treated with m-chloroperbenzoic acid, and after stirring at −78° C. for 5 minutes, the reaction is warmed to room temperature and stirred for 5 minutes further. Following the removal of solvent, the product is purified by flash chromatography on silica gel using ethyl acetate hexane. The protecting groups are removed by suitable deprotection reactions. Where the phosphoramidate employed is dibenzylphosphoramidate, the benzyl protecting groups may be removed by hydrogenation of the compound over Pd/C under 1 atmosphere of hydrogen at room temperature. The preparation of phosphoric acid mono-[3-(5,6-dihydro-4H-pyrrolo[3,2,1-ij]quinolin-1-yl)-4-(1H-indol-3-yl)-2,5-dioxo-pyrrolidin-1-ylmethyl]ester from 3-(5,6-dihydro-41H-pyrrolo[3,2,1-ij]quinolin-1-yl)-1-hydroxymethyl-4-(1H-indol-3-yl)-pyrrolidine-2,5-dione is described in Example 56, steps 2-3.

Compounds of formulas III, IIIa, IVa, IVb, Va, or Vb where R7 is a carboxylic acid group, or an amino carboxylic acid group, may be prepared by coupling the desired hydroxymethylene derivative with a carboxylic acid or amino carboxylic acid (amino acid) under conditions suitable for the formation of an ester linkage. A variety of dehydrating agents, including DCC (dicyclohexylcarbodiimide), HBTU (O-(benzotriazol-1-yl)-N,N,N',N'-tetramethyluronium hexafluorophosphate), or BOP ((benzotriazol-1-yloxy)tris(dimethylamino)phosphonium hexafluorophosphate) may be employed to drive the formation of the ester bond. In a preferred embodiment, the reactions are conducted in anhydrous THF in the presence of HBTU and DIEPA (N,N-diisopropylethylamine) at room temperature for 10 hours to 24 hours. Following completion of the dehydration reaction, solvent is removed under reduced pressure and the compounds are taken up in an organic solvent (e.g., ethyl acetate) and washed with water. The organic layer is dried and the residue purified by silica gel chromatography as necessary.

Where R7 is an amino carboxylic acid group, the starting materials for introducing the amino carboxylic acid group must contain a suitably protected amine. A variety of suitable amine-protecting groups may be advantageously employed including carbobenzyloxy-protected amines (e.g., the reactions may employ N-carbobenzyloxy glycine or N-carbobenzyloxy alanine etc.). Subsequent deprotection will yield the free product. Where the protecting group employed is carbobenzyloxy, deprotection may be accomplished by treating the amine protected product suspended in methanol with HCl (4M) in ethyl acetate in the presence of palladium on charcoal (Pd/C) under 1 atmosphere of hydrogen for 1-3 hours at room temperature. Examples 58-60 describe the preparation of compounds where R7 is a carboxylic acid group, or an amino carboxylic acid group.

Compounds of formulas III, IIIa, IVa, IVb, Va, or Vb where R7 is a peptide, may be prepared by coupling the desired hydroxymethylene derivative with a peptide bearing a free carboxylic acid group to form an ester linkage. Linking of a carboxyl functionality of a peptide and the hydroxymethylene group in an ester linkage may be conducted employing a suitably protected peptide, bearing for example, protected free amine groups protected with conventional N-protecting groups. Conditions suitable for the formation of an ester linkage, include those employing dehydrating agents, such as those described for the preparation of compounds of formulas III, IIIa, IVa, IVb, Va, or Vb where R4 is —CH$_2$R7 and R7 is a carboxylic acid group, or an amino carboxylic acid group.

2.1.5. Preparation of Compounds of Formula III, IIIa, IVa, IVb, Va, and Vb where R4 is —(C$_1$-C$_6$) alkyl Compounds of formulas III, IIIa, IVa, IVb, Va, or Vb where R4 is a —(C$_1$-C$_6$) alkyl may be prepared by reacting by reacting the desired compound of formula III, IIIa, IVa, IVb, Va, or Vb where R4 is H with a (C$_1$-C$_6$) alkyl halide, where the halide is preferably Cl, Br or I, in the presence of a suitable base at room temperature. Suitable bases include organic bases such as potassium tert-butoxide, sodium methoxide, and inorganic bases such as KOH, NaOH and K$_2$CO$_3$. Suitable solvents include polar aprotic solvents such as DMSO, THF, dioxane or other ethers, or DMF. In an alternative embodiment, the compound of formula III, IIIa, IVa, IVb, Va, or Vb where R4 is H is reacted with an organic or inorganic base to yield the conjugate base of the compound of formula III, IIIa, IVa, IVb, Va, or Vb, and the conjugate base is then reacted with the alkylhalide. Where the alkyl group is introduced into a compound of formula III or IIIa, the resulting alkylated compounds can be reduced to yield compounds of formulas IVa and IVb, Va and Vb, or a mixture of compounds of formulas IVa, IVb, Va, and Vb employing the reduction procedures described in Section I(b)(1). Example 61 describes the preparation of 3-(5,6-dihydro-4H-pyrrolo[3,2,1-ij]quinolin-1-yl)-4(1-methylindol-3-yl)-1-methyl pyrrole-2,5-dione using iodomethane as an alkylating agent, and its reduction by catalytic hydrogenation to yield (±)-cis-3-(5,6-dihydro-4H-pyrrolo[3,2,1-ij]quinolin-1-yl)-4(1-methylindol-3-yl)-1-methyl pyrrolidine-2,5-dione.

Compounds of formulas III, IIIa, IVa, IVb, Va, or Vb where R4 is a —(C$_1$-C$_6$) alkyl group may also be prepared by reacting the desired compound of formula III, IIIa, IVa, IVb, Va, or Vb where R4 is H with a (C$_1$-C$_6$) alkyl alcohol in the presence of diethylzodicarboxylate (DEAD) and triphenylphosphine. (See, e.g., Mitsunobu, O.; Wade, M.; Sano, T. J. Am Chem. Soc. 94: 694 (1972); Hughes, D. L., Organic Reactions, 42; 335-656(1992)). The reactions may be conducted in a variety of solvents including tetrahydrofuran (THF), dichloromethane, chloroform, acetonitrile, and benzene, preferably the solvent is THF.

2.1.6. Separation of Compounds of Formula III, IIIa, IVa, IVb, Va, and Vb

Where the isolation of an individual product having the structure of formulas III, IIIa, IVa, IVb, Va, or Vb is desired, the products may be separated by chromatography on one or more chromatography media. Chromatography may be carried out on a preparative scale or on an analytical scale to determine the identity and purity of the products present in a sample. Although any suitable chromatography media including, but not limited to, silica, reverse phase, ion exchange, chiral chromatographic media, or any combination thereof, may be advantageously employed for separations, the suitability of specific chromatographic media and conditions for the separation of products having formulas III, IIIa, IVa, IVb, Va, and Vb will depend upon the substituents present on the compounds. In preferred embodiments, chromatographic separations are conducted employing HPLC. In other preferred embodiments the separation is carried out using supercritical fluid chromatography. Where supercritical fluid chromatography is employed, CO$_2$, or mixtures of CO$_2$ with other solvents including acetonitrile (ACN), methanol, ethanol, isopropanol, or hexane, are the preferred mobile phase, with mixtures of CO$_2$ and methanol most preferred. A variety of chromatographic media (stationary phases) may be employed in supercritical fluid chromatography including, but not limited to: ChiralCel OA, OB, OD, or OJ; ChiralPak AD or AS; Cyclobond I, II, or III; and Chirobiotic T, V, and R media.

In more preferred embodiments, where the products are individual isomers of formulas IVa, IVb, Va, or Vb, mixtures containing two or more of the isomeric forms may be separated by using supercritical fluid chromatography on chiral media. In one more preferred embodiment, separations are conducted on CHIRALPAK® AD columns (Daicel (U.S.A.) Inc. Fort Lee, N.J.). In that embodiment, products are applied to the AD column in a mixture of methanol and acetonitrile, or in acetonitrile, and the column is subsequently eluted with 35% methanol in CO2 (65%). The separation of 3(R),4(S)-3-(5,6-dihydro-4H-pyrrolo[3,2,1-ij]quinolin-1-yl)-4(1H-indol-3-yl)pyrrolidine-2,5-dione and 3(S),4(R)-3-(5,6-dihydro-4H-pyrrolo[3,2,1-ij]quinolin-1-yl)-4(1H-indol-3-yl)pyrrolidine-2,5-dione on a CHIRALPAK® AD column is set forth in Example 4. The separation of (+) trans-3-(5,6-dihydro-4H-pyrrolo[3,2,1-ij]quinolin-1-yl)-4(1H-indol-3-yl)pyrrolidine-2,5-dione and (−)trans-3-(5,6-dihydro-4H-pyrrolo[3,2,1-ij]quinolin-1-yl)-4(1H-indol-3-yl)pyrrolidine-2,5-dione is set forth in Example 5.

The individual racemic forms of compounds of formulas III, IIIa, IVa, IVb, Va, or Va may also be resolved by physical methods, such as, for example, fractional crystallization or crystallization of diastereomeric derivatives. In addition, individual optical isomers can be obtained from racemic mixtures by conventional methods, such as, for example, salt formation with an optically active acid, where applicable, followed by crystallization.

2.2. Preparation of Compounds of Formula I and II where Y is a Bond

Compounds of formulas I and II, which are employed in the synthesis of pyrroloquinolinyl-pyrrole-2,5-dione of formulas III and IIIa, may be purchased or obtained via a variety of synthetic routes such as those set forth below.

2.2.1. Preparation of Compounds of Formula I where Y is a Bond

Compounds of formula I may be prepared from the corresponding compound of formula A, where X is selected from the group consisting of —(CH$_2$)—, —(NR8)-, S and O, R8 is selected from the group consisting of hydrogen, —(C$_1$-C$_6$) alkyl, —(C$_1$-C$_6$) substituted alkyl, —(C$_3$-C$_9$) cycloalkyl, —(C$_3$-C$_9$) substituted cycloalkyl, and —O—(C$_1$-C$_6$) alkyl, and m is 1 or 2. Exemplary compounds of formula A include 1,2,3,4-tetra hydroquinoline, 1,2,3,4-tetrahydro-quinoxaline, 3,4-dihydro-2H-benzo[1,4]oxazine, 3,4-dihydro-2H-benzo[1,4]thiazine, 2,3,4,5-tetrahydro-1H-benzo[b]azepine, 2,3,4,5-tetrahydro-1H-benzo[b][1,4]diazepine, 6,7,8,9-tetrahydro-5-oxa-9-aza-benzocycloheptene, or 2,3,4,5-tetrahydro-benzo[b][1,4]thiazepine). The preparation begins with the conversion of a compound of formula A to the corresponding 3-substituted-2-oxopropionic acid ethyl ester of formula B. The ethyl ester of formula B is cyclized to form a compound of formula C, which is converted to the free acid D, which is decarboxylated to yield the desired tricyclic product E. Subsequent reaction of the tricyclic product E with oxalyl chloride and work-up in alcoholic base yields the corresponding compound of formula I. Scheme 3 illustrates the reaction sequence beginning with compounds of formula A, which is further illustrated in Example 1, steps 1-5 for the preparation of 5,6-dihydro-4H-pyrrolo[3,2,1-ij]quinolin-1-yl)oxoacetic methyl ester of formula I from 1,2,3,4-tetrahydroquinoline and bromoethylpyruvate (3-bromo-pyruvic acid ethyl ester).

Some suitable conditions for the conversion of compounds of formula A into compounds of formula I through the reaction sequence of Scheme 3 are described herein. Compounds of formula A may be converted to the corresponding 3-substituted-2-oxopropionic acid ethyl ester of formula B by treatment with bromoethyl pyruvate in an anhydrous ether, such as THF, at room temperature for about 24 hours. Treatment of the 3-substituted-2-oxopropionic acid ethyl ester of formula B with anhydrous MgCl$_2$ in 2-methoxyethanol at about 125° C. for 30 minutes to 2 hours, preferably for 1 hour, results in the formation of the corresponding tricyclic carboxylic acid ester of formula C. Subsequent conversion of this compound to the free acid of formula D may be accomplished by hydrolysis in aqueous base. In preferred embodiments the reaction is carried out in an aqueous base, including but not limited to NaOH or KOH, in the presence of alcohol as a co-solvent. Preferred alcohol co-solvents include methanol, ethanol, n-propanol, and isopropanol, with ethanol as a more preferred co-solvent. Reactions are typically conducted by heating the mixture to reflux for 2 hours, although the time and temperature of the reaction may be varied as needed. Oxidative decarboxylation of compounds of formula D may be conducted by a variety of procedures suitable for the decarboxylation of aromatic acids. In preferred embodiments the decarboxylation of compounds of formula D is conducted by heating the free acid with copper-chromite (CuO—Cr$_2$O$_3$) in quinolone for about 2 hours to yield the decarboxylated product of formula E. Conversion of compounds of formula E to compounds of formula I may be accomplished by reaction with oxalyl chloride, followed by treatment with a mixture of an anhydrous alcohol and the alkaline metal salt of the alcohol, preferably sodium methoxide, or sodium ethoxide. The reaction of oxalyl chloride with compounds of formula E is typically conducted in anhydrous polar aprotic solvents including ethers at a temperature from about −78° C. to about 10° C. In preferred embodiments, the reaction is conducted at a temperature from about −25° C. to about 5° C. employing an ether as a solvent. In more preferred embodiments the reaction is conducted at 0° C. Preferred solvents for conducting the reaction include, but are not limited to tetrahydrofuran (THF), tetrahydropyran, diethyl ether and the like.

Scheme 3. Preparation of Compounds of Formula (I) where Y is a bond

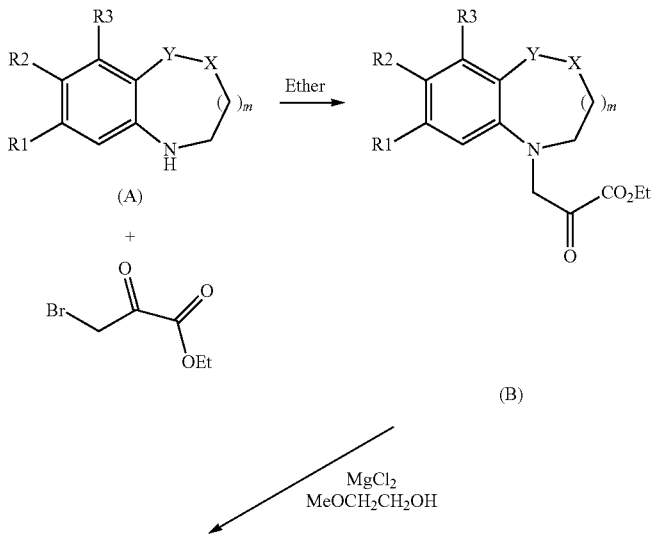

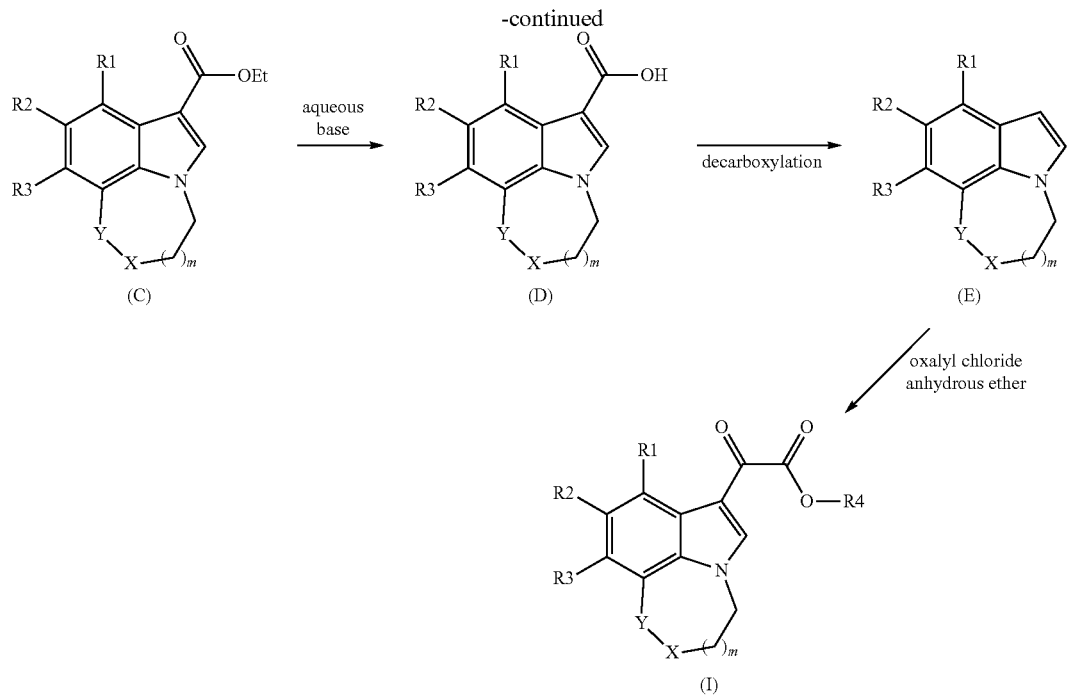

2.2.2. Preparation of Compounds of Formula II

Compounds of formula II, which are substituted acetamides, may be purchased or prepared from commercially available starting materials. Commercially available acetamides including: indole-3-acetamide, 2-(5-methyl-1H-indol-3-yl)acetamide, 2-(5-methoxy-1H-indol-3-yl)acetamide, 2-(4-hydroxy-1H-indol-3-yl)acetamide, 2-phenylacetamide, 2-(4-methylphenyl)acetamide, 4-hydroxyphenylacetamide, 4-hydroxyphenylacetamide, N-cyclopentyl-2-(4-hydroxy-2-oxo-1,2-dihydro-3-quinolinyl)acetamide, 2-phenoxyacetamide, 2-(2-methylphenoxy)acetamide, 2-(4-fluorophenoxy)acetamide, 2-(4-pyridinyl)acetamide, and 2-[(4-chlorophenyl)sulfanyl]acetamide are available from a variety of sources including Sigma Aldrich Chemical Co., St. Louis Mo. A compound of formula II may also be prepared from its corresponding free acid by conversion of the free acid to its acid chloride followed by reaction with ammonia.

2.3. Additional Routes for the Preparation of Pyrroloquinolinyl-pyrrolidine-2,5-diones In addition to those routes for the preparation of pyrroloquinolinyl-pyrrolidine-2,5-diones described above, additional routes of preparing the compounds exemplified for (±)-trans-3-(5,6-dihydro-4H-pyrrolo[3,2,1-ij]quinolin-1-yl)-4(1H-indol-3-yl)pyrrolidine-2,5-dione are described in Examples 62-64.

3. Methods of Treatment

As used herein, a "subject" can be any mammal, e.g., a human, a primate, mouse, rat, dog, cat, cow, horse, pig, sheep, goat, camel. In a preferred aspect, the subject is a human.

As used herein, a "subject in need thereof" is a subject having a cell proliferative disorder, or a subject having an increased risk of developing a cell proliferative disorder relative to the population at large. In one aspect, a subject in need thereof has a precancerous condition. In a preferred aspect, a subject in need thereof has cancer.

As used herein, the term "cell proliferative disorder" refers to conditions in which unregulated or abnormal growth, or both, of cells can lead to the development of an unwanted condition or disease, which may or may not be cancerous. In one aspect, a cell proliferative disorder includes a non-cancerous condition, e.g., rheumatoid arthritis; inflammation; autoimmune disease; lymphoproliferative conditions; acromegaly; rheumatoid spondylitis; osteoarthritis; gout, other arthritic conditions; sepsis; septic shock; endotoxic shock; gram-negative sepsis; toxic shock syndrome; asthma; adult respiratory distress syndrome; chronic obstructive pulmonary disease; chronic pulmonary inflammation; inflammatory bowel disease; Crohn's disease; psoriasis; eczema; ulcerative colitis; pancreatic fibrosis; hepatic fibrosis; acute and chronic renal disease; irritable bowel syndrome; pyresis; restenosis; cerebral malaria; stroke and ischemic injury; neural trauma; Alzheimer's disease; Huntington's disease; Parkinson's disease; acute and chronic pain; allergic rhinitis; allergic conjunctivitis; chronic heart failure; acute coronary syndrome; cachexia; malaria; leprosy; leishmaniasis; Lyme disease; Reiter's syndrome; acute synovitis; muscle degeneration, bursitis; tendonitis; tenosynovitis; herniated, ruptures, or prolapsed intervertebral disk syndrome; osteopetrosis; thrombosis; restenosis; silicosis; pulmonary sarcosis; bone resorption diseases, such as osteoporosis; graft-versus-host reaction; Multiple Sclerosis; lupus; fibromyalgia; AIDS and other viral diseases such as Herpes Zoster, Herpes Simplex I or II, influenza virus and cytomegalovirus; and diabetes mellitus. In another aspect, a cell proliferative disorder includes a precancer or a precancerous condition. In another aspect, a cell proliferative disorder includes cancer. Various cancers to be treated include but are not limited to breast cancer, lung cancer, colorectal cancer, pancreatic cancer, ovarian cancer, prostate cancer, renal carcinoma, hepatoma, brain cancer, melanoma, multiple myeloma, chronic myelogenous leukemia, hematologic tumor, and lymphoid tumor, including metastatic lesions in other tissues or organs distant from the primary tumor site. Cancers to be treated include but are not limited to sarcoma, carcinoma, and adenocarcinoma. In one aspect, a "precancer cell" or "precancerous cell" is a cell manifesting a cell proliferative disorder that is a precancer or a precancerous condition. In another aspect, a "cancer cell" or "cancerous cell" is a cell manifesting a cell proliferative disorder that is a cancer. Any reproducible means of measurement may be used to identify cancer cells or precancerous cells. In a preferred aspect, cancer cells or precancerous cells are identified by histological typing or grading of a tissue sample (e.g., a biopsy sample). In another aspect, cancer cells or precancerous cells are identified through the use of appropriate molecular markers.

A "cell proliferative disorder of the hematologic system" is a cell proliferative disorder involving cells of the hematologic system. In one aspect, a cell proliferative disorder of the hematologic system includes lymphoma, leukemia, myeloid neoplasms, mast cell neoplasms, myelodysplasia, benign monoclonal gammopathy, lymphomatoid granulomatosis, lymphomatoid papulosis, polycythemia vera, chronic myelocytic leukemia, agnogenic myeloid metaplasia, and essential thrombocythemia. In another aspect, a cell proliferative disorder of the hematologic system includes hyperplasia, dysplasia, and metaplasia of cells of the hematologic system. In a preferred aspect, compositions of the present invention may be used to treat a cancer selected from the group consisting of a hematologic cancer of the present invention or a hematologic cell proliferative disorder of the present invention. In one aspect, a hematologic cancer of the present invention includes multiple myeloma, lymphoma (including Hodgkin's lymphoma, non-Hodgkin's lymphoma, childhood lymphomas, and lymphomas of lymphocytic and cutaneous origin), leukemia (including childhood leukemia, hairy-cell leukemia, acute lymphocytic leukemia, acute myelocytic leukemia, chronic lymphocytic leukemia, chronic myelocytic leukemia, chronic myelogenous leukemia, and mast cell leukemia), myeloid neoplasms and mast cell neoplasms.

A "cell proliferative disorder of the lung" is a cell proliferative disorder involving cells of the lung. In one aspect, cell proliferative disorders of the lung include all forms of cell proliferative disorders affecting lung cells. In one aspect, cell proliferative disorders of the lung include lung cancer, a precancer or precancerous condition of the lung, benign growths or lesions of the lung, and malignant growths or lesions of the lung, and metastatic lesions in tissue and organs in the body other than the lung. In a preferred aspect, compositions of the present invention may be used to treat lung cancer or cell proliferative disorders of the lung. In one aspect, lung cancer includes all forms of cancer of the lung. In another aspect, lung cancer includes malignant lung neoplasms, carcinoma in situ, typical carcinoid tumors, and atypical carcinoid tumors. In another aspect, lung cancer includes small cell lung cancer ("SCLC"), non-small cell lung cancer ("NSCLC"), squamous cell carcinoma, adenocarcinoma, small cell carcinoma, large cell carcinoma, adenosquamous cell carcinoma, and mesothelioma. In another aspect, lung cancer includes "scar carcinoma," bronchoalveolar carcinoma, giant cell carcinoma, spindle cell carcinoma, and large cell neuroendocrine carcinoma. In another aspect, lung cancer includes lung neoplasms having histologic and ultrastructual heterogeneity (e.g., mixed cell types).

In one aspect, cell proliferative disorders of the lung include all forms of cell proliferative disorders affecting lung cells. In one aspect, cell proliferative disorders of the lung include lung cancer, precancerous conditions of the lung. In one aspect, cell proliferative disorders of the lung include hyperplasia, metaplasia, and dysplasia of the lung. In another aspect, cell proliferative disorders of the lung include asbestos-induced hyperplasia, squamous metaplasia, and benign reactive mesothelial metaplasia. In another aspect, cell proliferative disorders of the lung include replacement of columnar epithelium with stratified squamous epithelium, and mucosal dysplasia. In another aspect, individuals exposed to inhaled injurious environmental agents such as cigarette smoke and asbestos may be at increased risk for developing cell proliferative disorders of the lung. In another aspect, prior lung diseases that may predispose individuals to development of cell proliferative disorders of the lung include chronic interstitial lung disease, necrotizing pulmonary disease, scleroderma, rheumatoid disease, sarcoidosis, interstitial pneumonitis, tuberculosis, repeated pneumonias, idiopathic pulmonary fibrosis, granulomata, asbestosis, fibrosing alveolitis, and Hodgkin's disease.

A "cell proliferative disorder of the colon" is a cell proliferative disorder involving cells of the colon. In a preferred aspect, the cell proliferative disorder of the colon is colon cancer. In a preferred aspect, compositions of the present invention may be used to treat colon cancer or cell proliferative disorders of the colon. In one aspect, colon cancer includes all forms of cancer of the colon. In another aspect, colon cancer includes sporadic and hereditary colon cancers. In another aspect, colon cancer includes malignant colon neoplasms, carcinoma in situ, typical carcinoid tumors, and atypical carcinoid tumors. In another aspect, colon cancer includes adenocarcinoma, squamous cell carcinoma, and adenosquamous cell carcinoma. In another aspect, colon cancer is associated with a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis. In another aspect, colon cancer is caused by a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis.

In one aspect, cell proliferative disorders of the colon include all forms of cell proliferative disorders affecting colon cells. In one aspect, cell proliferative disorders of the colon include colon cancer, precancerous conditions of the colon, adenomatous polyps of the colon and metachronous lesions of the colon. In one aspect, a cell proliferative disorder of the colon includes adenoma. In one aspect, cell proliferative disorders of the colon are characterized by hyperplasia, metaplasia, and dysplasia of the colon. In another aspect, prior colon diseases that may predispose individuals to development of cell proliferative disorders of the colon include prior colon cancer. In another aspect, current disease that may predispose individuals to development of cell proliferative disorders of the colon include Crohn's disease and ulcerative colitis. In one aspect, a cell proliferative disorder of the colon is associated with a mutation in a gene selected from the group consisting of p53, ras, FAP and DCC. In another aspect, an individual has an elevated risk of developing a cell proliferative disorder of the colon due to the presence of a mutation in a gene selected from the group consisting of p53, ras, FAP and DCC.

A "cell proliferative disorder of the prostate" is a cell proliferative disorder involving cells of the prostate. In one aspect, cell proliferative disorders of the prostate include all forms of cell proliferative disorders affecting prostate cells. In one aspect, cell proliferative disorders of the prostate include prostate cancer, a precancer or precancerous condition of the prostate, benign growths or lesions of the prostate, and malignant growths or lesions of the prostate, and metastatic lesions in tissue and organs in the body other than the prostate. In another aspect, cell proliferative disorders of the prostate include hyperplasia, metaplasia, and dysplasia of the prostate.

A "cell proliferative disorder of the skin" is a cell proliferative disorder involving cells of the skin. In one aspect, cell proliferative disorders of the skin include all forms of cell proliferative disorders affecting skin cells. In one aspect, cell proliferative disorders of the skin include a precancer or precancerous condition of the skin, benign growths or lesions of the skin, melanoma, malignant melanoma and other malignant growths or lesions of the skin, and metastatic lesions in tissue and organs in the body other than the skin. In another aspect, cell proliferative disorders of the skin include hyperplasia, metaplasia, and dysplasia of the skin.

A "cell proliferative disorder of the ovary" is a cell proliferative disorder involving cells of the ovary. In one aspect, cell proliferative disorders of the ovary include all forms of cell proliferative disorders affecting cells of the ovary. In one aspect, cell proliferative disorders of the ovary include a precancer or precancerous condition of the ovary, benign growths or lesions of the ovary, ovarian cancer, malignant growths or lesions of the ovary, and metastatic lesions in tissue and organs in the body other than the ovary. In another aspect, cell proliferative disorders of the skin include hyperplasia, metaplasia, and dysplasia of cells of the ovary.

A "cell proliferative disorder of the breast" is a cell proliferative disorder involving cells of the breast. In one aspect, cell proliferative disorders of the breast include all forms of cell proliferative disorders affecting breast cells. In one aspect, cell proliferative disorders of the breast include breast cancer, a precancer or precancerous condition of the breast, benign growths or lesions of the breast, and malignant growths or lesions of the breast, and metastatic lesions in tissue and organs in the body other than the breast. In another aspect, cell proliferative disorders of the breast include hyperplasia, metaplasia, and dysplasia of the breast.

In one aspect, a cell proliferative disorder of the breast is a precancerous condition of the breast. In one aspect, compositions of the present invention may be used to treat a precancerous condition of the breast. In one aspect, a precancerous condition of the breast includes atypical hyperplasia of the breast, ductal carcinoma in situ (DCIS), intraductal carcinoma, lobular carcinoma in situ (LCIS), lobular neoplasia, and stage 0 or grade 0 growth or lesion of the breast (e.g., stage 0 or grade 0 breast cancer, or carcinoma in situ). In another aspect, a precancerous condition of the breast has been staged according to the TNM classification scheme as accepted by the American Joint Committee on Cancer (AJCC), where the primary tumor (T) has been assigned a stage of T0 or Tis; and where the regional lymph nodes (N) have been assigned a stage of N0; and where distant metastasis (M) has been assigned a stage of M0.

In a preferred aspect, the cell proliferative disorder of the breast is breast cancer. In a preferred aspect, compositions of the present invention may be used to treat breast cancer. In one aspect, breast cancer includes all forms of cancer of the breast. In one aspect, breast cancer includes primary epithelial breast cancers. In another aspect, breast cancer includes cancers in which the breast is involved by other tumors such as lymphoma, sarcoma or melanoma. In another aspect, breast cancer includes carcinoma of the breast, ductal carcinoma of the breast, lobular carcinoma of the breast, undifferentiated carcinoma of the breast, cystosarcoma phyllodes of the breast, angiosarcoma of the breast, and primary lymphoma of the breast. In one aspect, breast cancer includes Stage I, II, IIIA, IIIB, IIIC and IV breast cancer. In one aspect, ductal carcinoma of the breast includes invasive carcinoma, invasive carcinoma in situ with predominant intraductal component, inflammatory breast cancer, and a ductal carcinoma of the breast with a histologic type selected from the group consisting of comedo, mucinous (colloid), medullary, medullary with lymphcytic infiltrate, papillary, scirrhous, and tubular. In one aspect, lobular carcinoma of the breast includes invasive lobular carcinoma with predominant in situ component, invasive lobular carcinoma, and infiltrating lobular carcinoma. In one aspect, breast cancer includes Paget's disease, Paget's disease with intraductal carcinoma, and Paget's disease with invasive ductal carcinoma. In another aspect, breast cancer includes breast neoplasms having histologic and ultrastructual heterogeneity (e.g., mixed cell types).

In a preferred aspect, a compound of the present invention may be used to treat breast cancer. In one aspect, a breast cancer that is to be treated includes familial breast cancer. In another aspect, a breast cancer that is to be treated includes sporadic breast cancer. In one aspect, a breast cancer that is to be treated has arisen in a male subject. In one aspect, a breast cancer that is to be treated has arisen in a female subject. In one aspect, a breast cancer that is to be treated has arisen in a premenopausal female subject or a postmenopausal female subject. In one aspect, a breast cancer that is to be treated has arisen in a subject equal to or older than 30 years old, or a subject younger than 30 years old. In one aspect, a breast cancer that is to be treated has arisen in a subject equal to or older than 50 years old, or a subject younger than 50 years old. In one aspect, a breast cancer that is to be treated has arisen in a subject equal to or older than 70 years old, or a subject younger than 70 years old.

In one aspect, a breast cancer that is to be treated has been typed to identify a familial or spontaneous mutation in BRCA1, BRCA2, or p53. In one aspect, a breast cancer that is to be treated has been typed as having a HER2/neu gene amplification, as overexpressing HER2/neu, or as having a low, intermediate or high level of HER2/neu expression. In another aspect, a breast cancer that is to be treated has been typed for a marker selected from the group consisting of estrogen receptor (ER), progesterone receptor (PR), human epidermal growth factor receptor-2, Ki-67, CA15-3, CA 27-29, and c-Met. In one aspect, a breast cancer that is to be treated has been typed as ER-unknown, ER-rich or ER-poor. In another aspect, a breast cancer that is to be treated has been typed as ER-negative or ER-positive. ER-typing of a breast cancer may be performed by any reproducible means. In a preferred aspect, ER-typing of a breast cancer may be performed as set forth in Onkologie 27: 175-179 (2004). In one aspect, a breast cancer that is to be treated has been typed as PR-unknown, PR-rich or PR-poor. In another aspect, a breast cancer that is to be treated has been typed as PR-negative or PR-positive. In another aspect, a breast cancer that is to be treated has been typed as receptor positive or receptor negative. In one aspect, a breast cancer that is to be treated has been typed as being associated with elevated blood levels of CA 15-3, or CA 27-29, or both.

In one aspect, a breast cancer that is to be treated includes a localized tumor of the breast. In one aspect, a breast cancer that is to be treated includes a tumor of the breast that is associated with a negative sentinel lymph node (SLN) biopsy. In one aspect, a breast cancer that is to be treated includes a tumor of the breast that is associated with a positive sentinel lymph node (SLN) biopsy. In another aspect, a breast cancer that is to be treated includes a tumor of the breast that is associated with one or more positive axillary lymph nodes, where the axillary lymph nodes have been staged by any applicable method. In another aspect, a breast cancer that is to be treated includes a tumor of the breast that has been typed as having nodal negative status (e.g., node-negative) or nodal positive status (e.g., node-positive). In another aspect, a breast cancer that is to be treated includes a tumor of the breast that has metastasized to other locations in the body. In one aspect, a breast cancer that is to be treated is classified as having metastasized to a location selected from the group consisting of bone, lung, liver, or brain. In another aspect a breast cancer that is to be treated is classified according to a characteristic selected from the group consisting of metastatic, localized, regional, local-regional, locally advanced, distant, multicentric, bilateral, ipsilateral, contralateral, newly diagnosed, recurrent, and inoperable.

In one aspect, a compound of the present invention may be used to treat or prevent a cell proliferative disorder of the breast, or to treat or prevent breast cancer, in a subject having an increased risk of developing breast cancer relative to the population at large. In one aspect, a subject with an increased risk of developing breast cancer relative to the population at large is a female subject with a family history or personal history of breast cancer. In another aspect, a subject with an increased risk of developing breast cancer relative to the population at large is a female subject having a germ-line or spontaneous mutation in BRCA1 or BRCA2, or both. In one aspect, a subject with an increased risk of developing breast cancer relative to the population at large is a female subject with a family history of breast cancer and a germ-line or spontaneous mutation in BRCA1 or BRCA2, or both. In another aspect, a subject with an increased risk of developing breast cancer relative to the population at large is a female who is greater than 30 years old, greater than 40 years old, greater than 50 years old, greater than 60 years old, greater than 70 years old, greater than 80 years old, or greater than 90 years old. In one aspect, a subject with an increased risk of developing breast cancer relative to the population at large is a subject with atypical hyperplasia of the breast, ductal carcinoma in situ (DCIS), intraductal carcinoma, lobular carcinoma in situ (LCIS), lobular neoplasia, or a stage 0 growth or lesion of the breast (e.g., stage 0 or grade 0 breast cancer, or carcinoma in situ).

In another aspect, a breast cancer that is to be treated has been histologically graded according to the Scarff-Bloom-Richardson system, wherein a breast tumor has been assigned a mitosis count score of 1, 2, or 3; a nuclear pleiomorphism score of 1, 2, or 3; a tubule formation score of 1, 2, or 3; and a total Scarff-Bloom-Richardson score of between 3 and 9. In another aspect, a breast cancer that is to be treated has been assigned a tumor grade according to the International Consensus Panel on the Treatment of Breast Cancer selected from the group consisting of grade 1, grade 1-2, grade 2, grade 2-3, or grade 3.

In one aspect, a cancer that is to be treated has been staged according to the American Joint Committee on Cancer (AJCC) TNM classification system, where the tumor (T) has been assigned a stage of TX, T1, T1mic, T1a, T1b, T1c, T2, T3, T4, T4a, T4b, T4c, or T4d; and where the regional lymph nodes (N) have been assigned a stage of NX, N0, N1, N2, N2a, N2b, N3, N3a, N3b, or N3c; and where distant metastasis (M) has been assigned a stage of MX, M0, or M1. In another aspect, a cancer that is to be treated has been staged according to an American Joint Committee on Cancer (AJCC) classification as Stage I, Stage IIA, Stage IIB, Stage IIIA, Stage IIIB, Stage IIIC, or Stage IV. In another aspect, a cancer that is to be treated has been assigned a grade according to an AJCC classification as Grade GX (e.g., grade cannot be assessed), Grade 1, Grade 2, Grade 3 or Grade 4. In another aspect, a cancer that is to be treated has been staged according to an AJCC pathologic classification (pN) of pNX, pN0, PN0 (I−), PN0 (I+), PN0 (mol−), PN0 (mol+), PN1, PN1(mi), PN1a, PN1b, PN1c, pN2, pN2a, pN2b, pN3, pN3a, pN3b, or pN3c.

In one aspect, a cancer that is to be treated includes a tumor that has been determined to be less than or equal to about 2 centimeters in diameter. In another aspect, a cancer that is to be treated includes a tumor that has been determined to be from about 2 to about 5 centimeters in diameter. In another aspect, a cancer that is to be treated includes a tumor that has been determined to be greater than or equal to about 3 centimeters in diameter. In another aspect, a cancer that is to be treated includes a tumor that has been determined to be greater than 5 centimeters in diameter. In another aspect, a cancer that is to be treated is classified by microscopic appearance as well differentiated, moderately differentiated, poorly differentiated, or undifferentiated. In another aspect, a cancer that is to be treated is classified by microscopic appearance with respect to mitosis count (e.g., amount of cell division) or nuclear pleiomorphism (e.g., change in cells). In another aspect, a cancer that is to be treated is classified by microscopic appearance as being associated with areas of necrosis (e.g., areas of dying or degenerating cells). In one aspect, a cancer that is to be treated is classified as having an abnormal karyotype, having an abnormal number of chromosomes, or having one or more chromosomes that are abnormal in appearance. In one aspect, a cancer that is to be treated is classified as being aneuploid, triploid, tetraploid, or as having an altered ploidy. In one aspect, a cancer that is to be treated is classified as having a chromosomal translocation, or a deletion or duplication of an entire chromosome, or a region of deletion, duplication or amplification of a portion of a chromosome.

In one aspect, a cancer that is to be treated is evaluated by DNA cytometry, flow cytometry, or image cytometry. In one aspect, a cancer that is to be treated has been typed as having 10%, 20%, 30%, 40%, 50%, 60%, 70%, 80%, or 90% of cells in the synthesis stage of cell division (e.g., in S phase of cell division). In one aspect, a cancer that is to be treated has been typed as having a low S-phase fraction or a high S-phase fraction.

As used herein, a "normal cell" is a cell that cannot be classified as part of a "cell proliferative disorder." In one aspect, a normal cell lacks unregulated or abnormal growth, or both, that can lead to the development of an unwanted condition or disease. Preferably, a normal cell possesses normally functioning cell cycle checkpoint control mechanisms.

As used herein, "contacting a cell" refers to a condition in which a compound or other composition of matter is in direct contact with a cell, or is close enough to induce a desired biological effect in a cell.

As used herein, "candidate compound" refers to a compound of the present invention that has been or will be tested in one or more in vitro or in vivo biological assays, in order to determine if that compound is likely to elicit a desired biological or medical response in a cell, tissue, system, animal or human that is being sought by a researcher or clinician. In one aspect, a candidate compound is a compound of formula IIIa; in another aspect, a candidate compound is a compound of formula IVa, IVb, Va, or Vb. In a preferred aspect, the biological or medical response is treatment of cancer. In another aspect, the biological or medical response is treatment or prevention of a cell proliferative disorder. In one aspect, in vitro or in vivo biological assays include, but are not limited to, enzymatic activity assays, electrophoretic mobility shift assays, reporter gene assays, in vitro cell viability assays, and the assays set forth in Examples 65-73 herein.

As used herein, "monotherapy" refers to administration of a single active or therapeutic compound to a subject in need thereof. Preferably, monotherapy will involve administration of a therapeutically effective amount of an active compound. For example, cancer monotherapy with (±)-cis-3-(5,6-dihydro-4H-pyrrolo[3,2,1-ij]quinolin-1yl)-4(1H-indol-3-yl)pyrrolidine-2,5-dione comprises administration of a therapeutically effective amount of (±)-cis-3-(5,6-dihydro-4H-pyrrolo[3,2,1-ij]quinolin-1yl)-4(1H-indol-3-yl)pyrrolidine-2,5-dione, or a pharmaceutically acceptable salt, prodrug, metabolite, analog or derivative thereof, to a subject in need of treatment of cancer. Monotherapy may be contrasted with combination therapy, in which a combination of multiple active compounds is administered, preferably with each component of the combination present in a therapeutically effective amount. In one aspect, montherapy with a compound of the present invention is more effective than combination therapy in inducing a desired biological effect.

As used herein, "treating" describes the management and care of a patient for the purpose of combating a disease, condition, or disorder and includes the administration of a compound of the present invention to prevent the onset of the symptoms or complications, alleviating the symptoms or complications, or eliminating the disease, condition or disorder.

In one aspect, treating cancer results in a reduction in size of a tumor. A reduction in size of a tumor may also be referred to as "tumor regression." Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. In a preferred aspect, size of a tumor may be measured as a diameter of the tumor.

In another aspect, treating cancer results in a reduction in tumor volume. Preferably, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

In another aspect, treating cancer results in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. In a preferred aspect, number of tumors may be measured by counting tumors visible to the naked eye or at a specified magnification. In a preferred aspect, the specified magnification is 2×, 3×, 4×, 5×, 10×, or 50×.

In another aspect, treating cancer results in a decrease in number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. In a preferred aspect, the number of metastatic lesions may be measured by counting metastatic lesions visible to the naked eye or at a specified magnification. In a preferred aspect, the specified magnification is 2×, 3×, 4×, 5×, 10×, or 50×.

In another aspect, treating cancer results in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. In a preferred aspect, an increase in average survival time of a population may be measured, for example, by calculating for a population the average length of survival following initiation of treatment with an active compound. In another preferred aspect, an increase in average survival time of a population may also be measured, for example, by calculating for a population the average length of survival following completion of a first round of treatment with an active compound.

In another aspect, treating cancer results in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. In a preferred aspect, an increase in average survival time of a population may be measured, for example, by calculating for a population the average length of survival following initiation of treatment with an active compound. In another preferred aspect, an increase in average survival time of a population may also be measured, for example, by calculating for a population the average length of survival following completion of a first round of treatment with an active compound.

In another aspect, treating cancer results in increase in average survival time of a population of treated subjects in comparison to a population receiving monotherapy with a drug that is not a compound of the present invention, or a pharmaceutically acceptable salt, prodrug, metabolite, analog or derivative thereof. Preferably, the average survival time is increased by more than 30 days; more preferably, by more than 60 days; more preferably, by more than 90 days; and most preferably, by more than 120 days. An increase in average survival time of a population may be measured by any reproducible means. In a preferred aspect, an increase in average survival time of a population may be measured, for example, by calculating for a population the average length of survival following initiation of treatment with an active compound. In another preferred aspect, an increase in average survival time of a population may also be measured, for example, by calculating for a population the average length of survival following completion of a first round of treatment with an active compound.

In another aspect, treating cancer results in a decrease in the mortality rate of a population of treated subjects in comparison to a population receiving carrier alone. In another aspect, treating cancer results in a decrease in the mortality rate of a population of treated subjects in comparison to an untreated population. In a further aspect, treating cancer results a decrease in the mortality rate of a population of treated subjects in comparison to a population receiving monotherapy with a drug that is not a compound of the present invention, or a pharmaceutically acceptable salt, prodrug, metabolite, analog or derivative thereof. Preferably, the mortality rate is decreased by more than 2%; more preferably, by more than 5%; more preferably, by more than 10%; and most preferably, by more than 25%. In a preferred aspect, a decrease in the mortality rate of a population of treated subjects may be measured by any reproducible means. In another preferred aspect, a decrease in the mortality rate of a population may be measured, for example, by calculating for a population the average number of disease-related deaths per unit time following initiation of treatment with an active compound. In another preferred aspect, a decrease in the mortality rate of a population may also be measured, for example, by calculating for a population the average number of disease-related deaths per unit time following completion of a first round of treatment with an active compound.

In another aspect, treating cancer results in a decrease in tumor growth rate. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. In a preferred aspect, tumor growth rate is measured according to a change in tumor diameter per unit time.

In another aspect, treating cancer results in a decrease in tumor regrowth. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. In a preferred aspect, tumor regrowth is measured, for example, by measuring an increase in the diameter of a tumor after a prior tumor shrinkage that followed treatment. In another preferred aspect, a decrease in tumor regrowth is indicated by failure of tumors to reoccur after treatment has stopped.

In another aspect, treating or preventing a cell proliferative disorder results in a reduction in the rate of cellular proliferation. Preferably, after treatment, the rate of cellular proliferation is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The rate of cellular proliferation may be measured by any reproducible means of measurement. In a preferred aspect, the rate of cellular proliferation is measured, for example, by measuring the number of dividing cells in a tissue sample per unit time.

In another aspect, treating or preventing a cell proliferative disorder results in a reduction in the proportion of proliferating cells. Preferably, after treatment, the proportion of proliferating cells is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The proportion of proliferating cells may be measured by any reproducible means of measurement. In a preferred aspect, the proportion of proliferating cells is measured, for example, by quantifying the number of dividing cells relative to the number of nondividing cells in a tissue sample. In another preferred aspect, the proportion of proliferating cells is equivalent to the mitotic index.

In another aspect, treating or preventing a cell proliferative disorder results in a decrease in size of an area or zone of cellular proliferation. Preferably, after treatment, size of an area or zone of cellular proliferation is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Size of an area or zone of cellular proliferation may be measured by any reproducible means of measurement. In a preferred aspect, size of an area or zone of cellular proliferation may be measured as a diameter or width of an area or zone of cellular proliferation.

In another aspect, treating or preventing a cell proliferative disorder results in a decrease in the number or proportion of cells having an abnormal appearance or morphology. Preferably, after treatment, the number of cells having an abnormal morphology is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. An abnormal cellular appearance or morphology may be measured by any reproducible means of measurement. In one aspect, an abnormal cellular morphology is measured by microscopy, e.g., using an inverted tissue culture microscope. In one aspect, an abnormal cellular morphology takes the form of nuclear pleiomorphism.

As used herein, the term "selectively" means tending to occur at a higher frequency in one population than in another population. In one aspect, the compared populations are cell populations. In a preferred aspect, a compound of the present invention, or a pharmaceutically acceptable salt, prodrug, metabolite, analog or derivative thereof, acts selectively on a cancer or precancerous cell but not on a normal cell. In another preferred aspect, a compound of the present invention, or a pharmaceutically acceptable salt, prodrug, metabolite, analog or derivative thereof, acts selectively to modulate one molecular target (e.g., c-Met) but does not significantly modulate another molecular target (e.g., Protein Kinase C). In another preferred aspect, the invention provides a method for selectively inhibiting the activity of an enzyme, such as a kinase. Preferably, an event occurs selectively in population A relative to population B if it occurs greater than two times more frequently in population A as compared to population B. More preferably, an event occurs selectively if it occurs greater than five times more frequently in population A. More preferably, an event occurs selectively if it occurs greater than ten times more frequently in population A; more preferably, greater than fifty times; even more preferably, greater than 100 times; and most preferably, greater than 1000 times more frequently in population A as compared to population B. For example, cell death would be said to occur selectively in cancer cells if it occurred greater than twice as frequently in cancer cells as compared to normal cells.

In a preferred aspect, a compound of the present invention or a pharmaceutically acceptable salt, prodrug, metabolite, analog or derivative thereof, modulates the activity of a molecular target (e.g., c-Met). In one aspect, modulating refers to stimulating or inhibiting an activity of a molecular target. Preferably, a compound of the present invention modulates the activity of a molecular target if it stimulates or inhibits the activity of the molecular target by at least 2-fold relative to the activity of the molecular target under the same conditions but lacking only the presence of said compound. More preferably, a compound of the present invention modulates the activity of a molecular target if it stimulates or inhibits the activity of the molecular target by at least 5-fold, at least 10-fold, at least 20-fold, at least 50-fold, at least 100-fold relative to the activity of the molecular target under the same conditions but lacking only the presence of said compound. The activity of a molecular target may be measured by any reproducible means. The activity of a molecular target may be measured in vitro or in vivo. For example, the activity of a molecular target may be measured in vitro by an enzymatic activity assay or a DNA binding assay, or the activity of a molecular target may be measured in vivo by assaying for expression of a reporter gene.

In one aspect, a compound of the present invention, or a pharmaceutically acceptable salt, prodrug, metabolite, analog or derivative thereof, does not significantly modulate the activity of a molecular target if the addition of the compound does not stimulate or inhibit the activity of the molecular target by greater than 10% relative to the activity of the molecular target under the same conditions but lacking only the presence of said compound. In a preferred aspect, a compound of the present invention does not significantly modulate the activity of Protein Kinase C.

As used herein, the term "isozyme selective" means preferential inhibition or stimulation of a first isoform of an enzyme in comparison to a second isoform of an enzyme (e.g., preferential inhibition or stimulation of a kinase isozyme alpha in comparison to a kinase isozyme beta). Preferably, a compound of the present invention demonstrates a minimum of a four fold differential, preferably a ten fold differential, more preferably a fifty fold differential, in the dosage required to achieve a biological effect. Preferably, a compound of the present invention demonstrates this differential across the range of inhibition, and the differential is exemplified at the IC so, i.e., a 50% inhibition, for a molecular target of interest.

In a preferred embodiment, administering a compound of the present invention, or a pharmaceutically acceptable salt, prodrug, metabolite, analog or derivative thereof, to a cell or a subject in need thereof results in modulation (i.e., stimulation or inhibition) of an activity of c-Met. As used herein, an activity of c-Met refers to any biological function or activity that is carried out by c-Met. For example, a function of c-Met includes phosphorylation of downstream target proteins. Other functions of c-Met include autophosphorylation, binding of adaptor proteins such as Gab-1, Grb-2, Shc, SHP2 and c-Cbl, and activation of signal transducers such as Ras, Src, PI3K, PLC-γ, STATs, ERK1 and 2 and FAK.

In a preferred embodiment, administering a compound of the present invention, or a pharmaceutically acceptable salt, prodrug, metabolite, analog or derivative thereof, to a cell or a subject in need thereof results in modulation (i.e., stimulation or inhibition) of an activity of ERK 1 or ERK 2, or both. As used herein, an activity of ERK 1 or ERK 2 refers to any biological function or activity that is carried out by ERK 1 or ERK 2. For example, a function of ERK 1 or ERK 2 includes phosphorylation of downstream target proteins.

In one aspect, activating refers to placing a composition of matter (e.g., protein or nucleic acid) in a state suitable for carrying out a desired biological function. In one aspect, a composition of matter capable of being activated also has an unactivated state. In one aspect, an activated composition of matter may have an inhibitory or stimulatory biological function, or both.

In one aspect, elevation refers to an increase in a desired biological activity of a composition of matter (e.g., a protein or a nucleic acid). In one aspect, elevation may occur through an increase in concentration of a composition of matter.

As used herein, "a cell cycle checkpoint pathway" refers to a biochemical pathway that is involved in modulation of a cell cycle checkpoint. A cell cycle checkpoint pathway may have stimulatory or inhibitory effects, or both, on one or more functions comprising a cell cycle checkpoint. A cell cycle checkpoint pathway is comprised of at least two compositions of matter, preferably proteins, both of which contribute to modulation of a cell cycle checkpoint. A cell cycle checkpoint pathway may be activated through an activation of one or more members of the cell cycle checkpoint pathway. Preferably, a cell cycle checkpoint pathway is a biochemical signaling pathway.

As used herein, "cell cycle checkpoint regulator" refers to a composition of matter that can function, at least in part, in modulation of a cell cycle checkpoint. A cell cycle checkpoint regulator may have stimulatory or inhibitory effects, or both, on one or more functions comprising a cell cycle checkpoint. In one aspect, a cell cycle checkpoint regulator is a protein. In another aspect, a cell cycle checkpoint regulator is not a protein.

In one aspect, treating cancer or a cell proliferative disorder results in cell death, and preferably, cell death results in a decrease of at least 10% in number of cells in a population. More preferably, cell death means a decrease of at least 20%; more preferably, a decrease of at least 30%; more preferably, a decrease of at least 40%; more preferably, a decrease of at least 50%; most preferably, a decrease of at least 75%. Number of cells in a population may be measured by any reproducible means. In one aspect, number of cells in a population is measured by fluorescence activated cell sorting (FACS). In another aspect, number of cells in a population is measured by immunofluorescence microscopy. In another aspect, number of cells in a population is measured by light microscopy. In another aspect, methods of measuring cell death are as shown in Li et al., (2003) *Proc Natl Acad Sci USA*. 100(5): 2674-8. In an aspect, cell death occurs by apoptosis.

In a preferred aspect, an effective amount of a compound of the present invention, or a pharmaceutically acceptable salt, prodrug, metabolite, analog or derivative thereof is not significantly cytotoxic to normal cells. A therapeutically effective amount of a compound is not significantly cytotoxic to normal cells if administration of the compound in a therapeutically effective amount does not induce cell death in greater than 10% of normal cells. A therapeutically effective amount of a compound does not significantly affect the viability of normal cells if administration of the compound in a therapeutically effective amount does not induce cell death in greater than 10% of normal cells. In an aspect, cell death occurs by apoptosis.

In one aspect, contacting a cell with a compound of the present invention, or a pharmaceutically acceptable salt, prodrug, metabolite, analog or derivative thereof, induces or activates cell death selectively in cancer cells. Preferably, administering to a subject in need thereof a compound of the present invention, or a pharmaceutically acceptable salt, prodrug, metabolite, analog or derivative thereof, induces or activates cell death selectively in cancer cells. In another aspect, contacting a cell with a compound of the present invention, or a pharmaceutically acceptable salt, prodrug, metabolite, analog or derivative thereof, induces cell death selectively in one or more cells affected by a cell proliferative disorder. Preferably, administering to a subject in need thereof a compound of the present invention, or a pharmaceutically acceptable salt, prodrug, metabolite, analog or derivative thereof, induces cell death selectively in one or more cells affected by a cell proliferative disorder. In a preferred aspect, the present invention relates to a method of treating or preventing cancer by administering a compound of the present invention, or a pharmaceutically acceptable salt, prodrug, metabolite, analog or derivative thereof to a subject in need thereof, where administration of the compound of the present invention, or a pharmaceutically acceptable salt, prodrug, metabolite, analog or derivative thereof results in one or more of the following: accumulation of cells in G1 and/or S phase of the cell cycle, cytotoxicity via cell death in cancer cells without a significant amount of cell death in normal cells, antitumor activity in animals with a therapeutic index of at least 2, and activation of a cell cycle checkpoint. As used herein, "therapeutic index" is the maximum tolerated dose divided by the efficacious dose.

One skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* (3d ed.), Cold Spring Harbor Press, Cold Spring Harbor, N.Y. (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, Pa., 18th edition (1990). These texts can, of course, also be referred to in making or using an aspect of the invention.

In additional aspects, a compound of the present invention, or a pharmaceutically acceptable salt, prodrug, metabolite, analog or derivative thereof, may be administered in combination with a second chemotherapeutic agent. The second chemotherapeutic agent can be a taxane, an aromatase inhibitor, an anthracycline, a microtubule targeting drug, a topoisomerase poison drug, a targeted monoclonal or polyconal antibody, an inhibitor of a molecular target or enzyme (e.g., a kinase inhibitor), or a cytidine analogue drug. In preferred aspects, the chemotherapeutic agent can be, but not restricted to, tamoxifen, raloxifene, anastrozole, exemestane, letrozole, HERCEPTIN® (trastuzumab), GLEEVEC® (imatinib), TAXOL® (paclitaxel), cyclophosphamide, lovastatin, minosine, araC, 5-fluorouracil (5-FU), methotrexate (MTX), TAXOTERE® (docetaxel), ZOLADEX® (goserelin), vincristine, vinblastine, nocodazole, teniposide, etoposide, GEMZAR® (gemcitabine), epothilone, navelbine, camptothecin, daunorubicin, dactinomycin, mitoxantrone, amsacrine, doxorubicin (adriamycin), epirubicin or idarubicin or agents listed in www.cancer.org/docroot/cdg/cdg_0.asp.

In another aspect, the second chemotherapeutic agent can be a cytokine such as G-CSF (granulocyte colony stimulating factor). In another aspect, a compound of the present invention, or a pharmaceutically acceptable salt, prodrug, metabolite, analog or derivative thereof, may be administered in combination with radiation therapy. In yet another aspect, a compound of the present invention, or a pharmaceutically acceptable salt, prodrug, metabolite, analog or derivative thereof, may be administered in combination with standard chemotherapy combinations such as, but not restricted to, CMF (cyclophosphamide, methotrexate and 5-fluorouracil), CAF (cyclophosphamide, adriamycin and 5-fluorouracil), AC (adriamycin and cyclophosphamide), FEC (5-fluorouracil, epirubicin, and cyclophosphamide), ACT or ATC (adriamycin, cyclophosphamide, and paclitaxel), or CMFP (cyclophosphamide, methotrexate, 5-fluorouracil and prednisone).

A compound of the present invention, or a pharmaceutically acceptable salt, prodrug, metabolite, analog or derivative thereof, can be incorporated into pharmaceutical compositions suitable for administration. Such compositions typically comprise the compound (i.e. including the active compound), and a pharmaceutically acceptable excipient or carrier. As used herein, "pharmaceutically acceptable excipient" or "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field. Preferred examples of such carriers or diluents include, but are not limited to, water, saline, ringer's solutions, dextrose solution, and 5% human serum albumin. Pharmaceutically acceptable carriers include solid carriers such as lactose, terra alba, sucrose, talc, gelatin, agar, pectin, acacia, magnesium stearate, stearic acid and the like. Exemplary liquid carriers include syrup, peanut oil, olive oil, water and the like. Similarly, the carrier or diluent may include time-delay material known in the art, such as glyceryl monostearate or glyceryl distearate, alone or with a wax, ethylcellulose, hydroxypropylmethylcellulose, methylmethacrylate or the like. Other fillers, excipients, flavorants, and other additives such as are known in the art may also be included in a pharmaceutical composition according to this invention. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

In one aspect, a compound of the present invention, or a pharmaceutically acceptable salt, prodrug, metabolite, analog or derivative thereof, is administered in a suitable dosage form prepared by combining a therapeutically effective amount (e.g., an efficacious level sufficient to achieve the desired therapeutic effect through inhibition of tumor growth, killing of tumor cells, treatment or prevention of cell proliferative disorders, etc.) of a compound of the present invention, or a pharmaceutically acceptable salt, prodrug, metabolite, analog or derivative thereof, (as an active ingredient) with standard pharmaceutical carriers or diluents according to conventional procedures (i.e., by producing a pharmaceutical composition of the invention). These procedures may involve mixing, granulating, and compressing or dissolving the ingredients as appropriate to attain the desired preparation.

4. The Pharmaceutical Compositions and Formulations

A pharmaceutical composition of the invention is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A compound or pharmaceutical composition of the invention can be administered to a subject in many of the well-known methods currently used for chemotherapeutic treatment. For example, for treatment of cancers, a compound of the invention may be injected directly into tumors, injected into the blood stream or body cavities or taken orally or applied through the skin with patches. The dose chosen should be sufficient to constitute effective treatment but not so high as to cause unacceptable side effects. The state of the disease condition (e.g., cancer, precancer, and the like) and the health of the patient should preferably be closely monitored during and for a reasonable period after treatment.

The term "therapeutically effective amount," as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In a preferred aspect, the disease or condition to be treated is cancer. In another aspect, the disease or condition to be treated is a cell proliferative disorder.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present invention may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In one aspect, the active compounds are prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

In therapeutic applications, the dosages of the pharmaceutical compositions used in accordance with the invention vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. Dosages can range from about 0.01 mg/kg per day to about 3000 mg/kg per day. In preferred aspects, dosages can range from about 1 mg/kg per day to about 1000 mg/kg per day. In an aspect, the dose will be in the range of about 0.1 mg/day to about 50 g/day; about 0.1 mg/day to about 25 g/day; about 0.1 mg/day to about 10 g/day; about 0.1 mg to about 3 g/day; or about 0.1 mg to about 1 g/day, in single, divided, or continuous doses (which dose may be adjusted for the patient's weight in kg, body surface area in $m^2$, and age in years). An effective amount of a pharmaceutical agent is that which provides an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

The pharmaceutical compositions can be included in a container, pack, or dispenser together with instructions for administration.

All patents, patent applications and references cited herein are incorporated by reference herein in their entirety.

EXAMPLES

Examples are provided below to further illustrate different features of the present invention. The examples also illustrate useful methodology for practicing the invention. These examples do not limit the claimed invention.

Example 1

Preparation of 3-(5,6-Dihydro-4H-pyrrolo[3,2,1-ij]quinolin-1-yl)-4(1H-indol-3-yl) pyrrole-2,5-dione Step 1

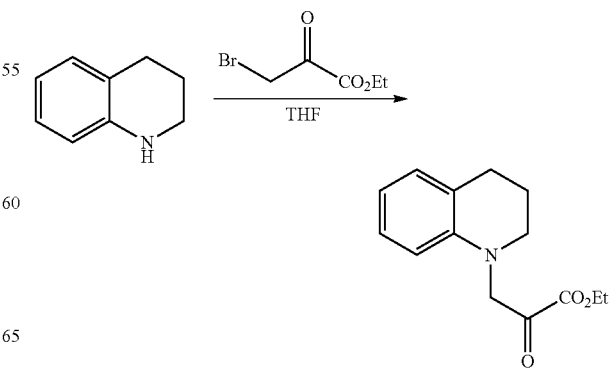

To a solution of 1,2,3,4-tetrahydroquinoline (100 ml) in anhydrous tetrahydrofuran (300 ml), bromoethylpyrruvate (53 ml) was added dropwise over 30 minutes. The mixture was stirred for 24 hours at room temperature. The reaction mixture was filtered and the solid washed with tetrahydrofuran (100 ml). The filtrate was evaporated to dryness to give 3-(3,4-dihydro-2H-quinolin-1-yl)-2-oxopropionic acid ethyl ester as a brown oil 117 g.

Step 2

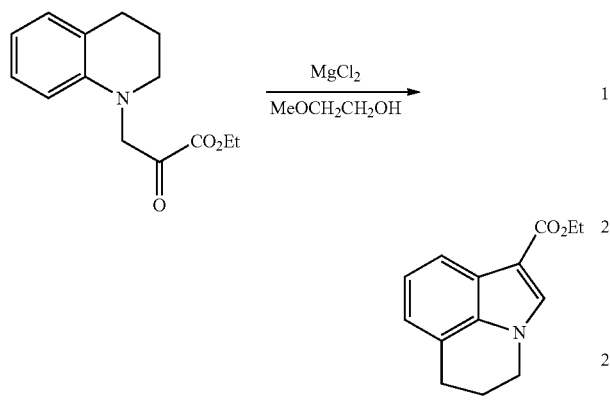

Anhydrous magnesium chloride (29.4 g, 0.31 mol) was suspended in 2-methoxyethanol (400 mil), and the mixture was stirred for 15 minutes at 125° C. A solution of 3-(3,4-dihydro-2H-quinolin-1-yl)-2-oxopropionic acid ethyl ester (76.57 g 0.31 mol) in 2-methoxyethanol (100 ml) was then added and the mixture stirred at 125° C. for 60 minutes. The mixture was stirred for a further 5 hours at reflux, cooled and evaporated to dryness. The residue was then acidified with 2 M hydrochloric acid (500 ml) and extracted with dichloromethane (3×500 ml). The combined organic layers were then washed with 5% sodium bicarbonate solution and dried over anhydrous magnesium sulfate before being evaporated to dryness. The residue was then purified on a silica gel chromatography column, eluting with ethyl acetate/hexanes (1:4) to provide 5,6-dihydro-4H-pyrrolo[3,2,1-ij]quinoline-1-carboxylic acid ethyl ester (31.0 g, 47%). $^1$H NMR (CDCl$_3$) 400 MHz δ: 7.9 (d, 1H, J=8 Hz), 7.79 (s, 1H), 7.17 (m, 1H), 6.99 (d, 1H, J=7.2 Hz), 4.37 (m, 2H), 4.18 (t, 2H, J=5.6 Hz), 3.0 (t, 2H, J=6 Hz), 2.24 (t, 2H, J=6 Hz), 1.42 (t, 3H, J=7.2 Hz).

Step 3

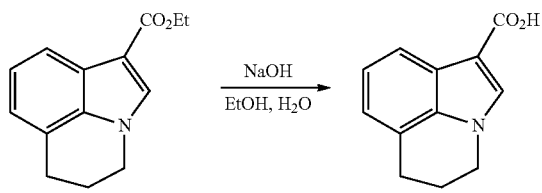

To a solution of 5,6-dihydro-4H-pyrrolo[3,2,1-ij]quinoline-1-carboxylic acid ethyl ester (31 g, 0.14 mol) in ethanol (200 ml) and water (200 ml) was added sodium hydroxide (30.8 g, 0.77 mol). The mixture was heated to reflux for 2 hours before being cooled to room temperature and diluted with water (2.64 L). The mixture was then washed with dichloromethane (2×300 ml) and the aqueous layer was acidified with concentrated hydrochloric acid to pH 1.0. The precipitate formed was collected by filtration, washed with water and dried to yield 5,6-dihydro-4H-pyrrolo[3,2,1-ij]quinoline-1-carboxylic acid as a dark yellow solid (23 g, 85%). $^1$H NMR (DMSO-d$_6$) 400 MHz δ: 11.95 (brs, 1H), 7.96 (s, 1H), 7.69 (d, 1H, J=8.4 Hz), 7.06 (t, 1H, J=6.8 Hz), 6.92 (d, 1H, J=6.8 Hz), 4.19 (t, 2H, J=6 Hz), 2.91 (t, 2H, J=6 Hz), 2.11 (t, 2H, J=5.6 Hz).

Step 4

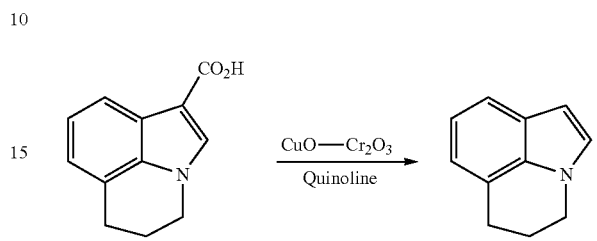

5,6-dihydro-4H-pyrrolo[3,2,1-ij]quinoline-1-carboxylic acid (37.5 g, 0.186 mol), copper chromite (13.5 g, 43 mmol) and quinoline (180 ml) were heated with stirring to 185° C. for 2 hours. The mixture was cooled, diluted with dichloromethane (1 L) and filtered over hyflo. The filtrate was washed with 2 M hydrochloric acid (2×600 ml) and twice with 2 M sodium hydroxide (150 ml) before being evaporated to dryness. The residue was purified by silica gel chromatography, eluting with a ethyl acetate/hexanes (1:6) to afford 5,6-dihydro-4H-pyrrolo[3,2,1-ij]quinoline (21 g, 72%) as a pale yellow solid. $^1$H NMR (CDCl$_3$) 400 MHz δ: 7.44 (dd, 1H, J=0.8 and 7.6 Hz), 7.07 (d, 1H, J=3.2 Hz), 7.01 (t, 1H, J=7.2 Hz), 6.9 (dd, 1H, J=0.8 and 6.8 Hz), 6.43 (d, 1H, J=3.2 Hz), 4.16 (t, 2H, J=6 Hz), 2.99 (t, 2H, J=6.4 Hz), 2.24 (m, 2H).

Step 5

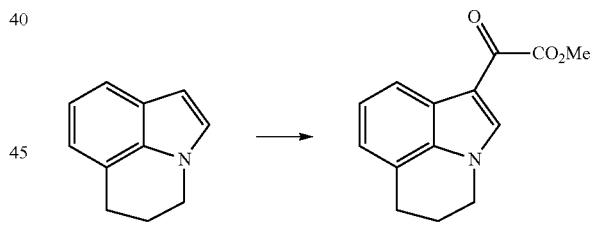

To a solution of 5,6-dihydro-4H-pyrroloquinoline (4.0 g, 25.3 mmol), in anhydrous ether (300 ml) at 0° C., was added oxalyl chloride (2.22 ml, 25.3 mmol). The mixture was stirred for 30-45 minutes at 0° C. before being cooled to −78° C. Sodium methoxide in methanol (0.5M) (60 ml) was then added slowly and the mixture allowed to warm to room temperature. The mixture was then diluted with ethyl acetate (200 ml), washed with water (100 ml) followed by a wash with saturated aqueous sodium chloride (50 ml). The organic layer was dried over anhydrous sodium sulfate and evaporated to dryness. The residue was dissolved in ethyl acetate (100 ml) filtered through a 2 inch plug of coarse silica gel and evaporated to give 5,6-dihydro-4H-pyrrolo[3,2,1-ij]quinolin-1-yl)oxoacetic acid methyl ester as a yellow solid (5.3 g, 85%). $^1$H NMR (CDCl$_3$) 400 MHz δ: 8.3 (s, 1H), 8.14 (d, 1H), 7.22 (t, 1H), 7.04 (d, 1H, J=7.2 Hz), 4.2 (t, 2H), 3.95 (s, 3H), 3.0 (t, 2H), 2.3 (t, 2H).

Step 6

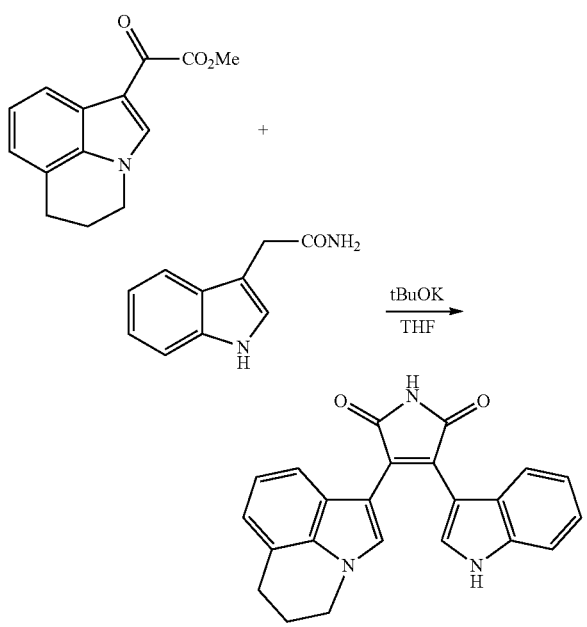

To a solution of 5,6-dihydro-4H-pyrrolo[3,2,1-ij]quinolin-1-yl)oxoacetic acid methyl ester (1.0 g, 4.12 mmol) and indole-3-acetamide (0.8 g, 4.5 mmol) in anhydrous tetrahydrofuran at 0° C. was added a solution of potassium t-butoxide (1M in tetrahydrofuran) (12.4 ml, 12.4 mmol) dropwise over 30 minutes. The mixture was stirred at 0° C. for 2 hours. Concentrated hydrochloric acid (10 ml) was then added and the mixture stirred for 1 hour at room temperature. The mixture was then diluted with ethyl acetate (200 ml), washed twice with water (50 ml), and saturated aqueous sodium chloride solution (50 ml) and the organic layer dried over anhydrous sodium sulfate. The residue was purified by silica gel chromatography, eluting with ethyl acetate/hexanes (1:4) to afford 3-(5,6-dihydro-4H-pyrrolo[3,2,1-ij]quinolin-1-yl)-4(1H-indol-3-yl)pyrrole-2,5-dione as a bright red solid (1.2 g, 80%). $^1$H NMR (CDCl$_3$) 400 MHz δ: 8.5 (brs, 1H), 7.78 (s, 1H), 7.63 (d, 1H, J=2.8 Hz), 7.44 (s, 1H), 7.35 (d, 1H, J=8 Hz), 7.16 (d, 1H, J=8.4 Hz), 7.11 (t, 1H, J=7.6 Hz), 6.86 (t, 1H, J=7.6 Hz), 6.80 (d, 1H, J=7.2 Hz), 6.64 (t, 1H, J=8 Hz), 6.57 (d, 1H, J=8 Hz), 4.2 (t, 2H, J=6 Hz), 2.96 (t, 2H, J=6 Hz), 2.24 (m, 2H).

Example 2

Preparation of (±)-Cis-3-(5,6-dihydro-4H-pyrrolo[3,2,1-ij]quinolin-1-yl)-4(1H-indol-3-yl)pyrrolidine-2,5-dione and (±)-Trans-3-(5,6-dihydro-4H-pyrrolo[3,2,1-ij]quinolin-1-yl)-4(1H-indol-3-yl)pyrrolidine-2,5-dione Preparation of the (±)-cis compounds, (±)-trans compounds, or mixtures thereof were obtained using reducing conditions as described in each of Procedures A through C.

Procedure A: Reduction of 3-(5,6-dihydro-4H-pyrrolo[3,2,1-ij]quinolin-1-yl)-4(1H-indol-3-yl)pyrrole-2,5-dione with Zn/Hg

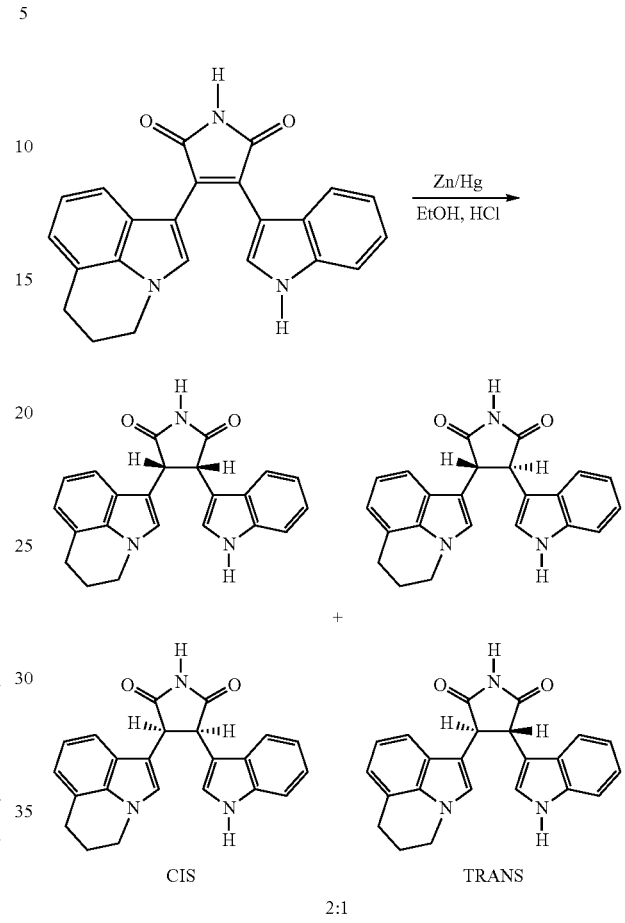

The active zinc-mercury reducing agent for the reduction of 3-(5,6-dihydro-4H-pyrrolo[3,2,1-ij]quinolin-1yl)-4(1H-indol-3-yl)pyrrole-2,5-dione was prepared from metallic zinc and HgCl$_2$. Zinc powder (2.5 g) and mercury (II) chloride (0.25 g) were suspended in de-ionized water (3 ml) and stirred for 20 minutes. A few drops of concentrated hydrochloric acid was then added and the mixture stirred for few minutes. The solid was filtered off, washed with de-ionized water (50 ml), ethanol (50 ml) and dried.

To a suspension of the Zn(Hg) reducing agent prepared as above in dry ethanol (50 ml) was added 3-(5,6-dihydro-4H-pyrrolo[3,2,1-ij]quinolin-1-yl)-4(1H-indol-3-yl)pyrrole-2,5-dione (0.35 g, 95.4 µmol.). The mixture was heated to reflux for 30-60 minutes while dry hydrogen chloride gas was slowly passed through the mixture. The mixture was then cooled, filtered, and evaporated to dryness. A 5% potassium carbonate solution (150 ml) and ethyl acetate (300 ml) were then added. The organic layer was dried over anhydrous magnesium sulfate and evaporated to give ~2:1 mixture of (±)-cis-3-(5,6-dihydro-4H-pyrrolo[3,2,1-ij]quinolin-1-yl)-4(1H-indol-3-yl)pyrrolidine-2,5-dione and (±)-trans-3-(5,6-dihydro-4H-pyrrolo[3,2,1-ij]quinolin-1-yl)-4(1H-indol-3-yl)pyrrolidine-2,5-dione (0.2 g).

Procedure B: Reduction of 3-(5,6-dihydro-4H-pyrrolo[3,2,1-ij]quinolin-1-yl)-4(1H-indol-3-yl) pyrrole-2,5-dione with hydrogen in the presence of palladium on carbon

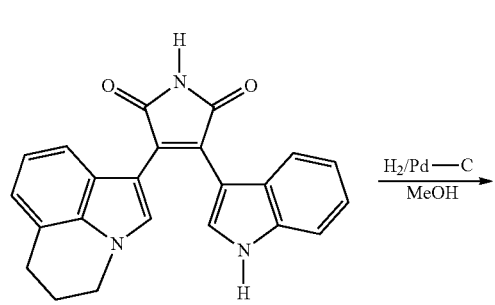

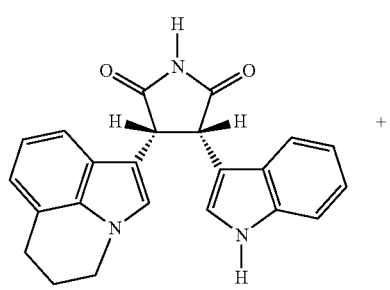

+

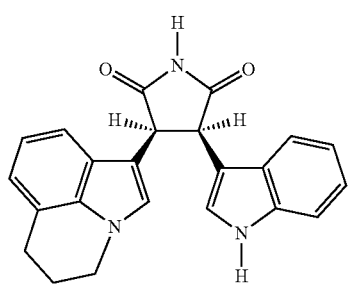

A suspension of 3-(5,6-dihydro-4H-pyrrolo[3,2,1-ij]quinolin-1-yl)-4(1H-indol-3-yl)pyrrole-2,5-dione (16 g, 43.6 mmol) and 10% palladium on carbon (Pd/C, wet catalyst) (8 g) were stirred under 1 atmosphere of hydrogen in methanol (600 ml) at room temperature for 48 hours. The catalyst was then filtered through a bed of Celite and the filtrate evaporated to dryness. The residue was re-dissolved in methanol and the product precipitated by the addition of cold water. The precipitate was filtered, washed with water and dried under vacuum to yield (+)-cis-3-(5,6-dihydro-4H-pyrrolo[3,2,1-ij]quinolin-1-yl)-4(1H-indol-3-yl)pyrrolidine-2,5-dione (9.2 g). $^1$H NMR (DMSO-d$_6$) 400 MHz δ: 11.56 (s, 1H), 10.66 (s, 1H), 7.43 (d, 1H, J=7.6 Hz), 7.14 (d, 2H, J=8 Hz), 6.86-6.97 (m, 4H), 6.78 (t, 1H, J=7.2 Hz), 6.69 (d, 1H, J=6.8 Hz), 4.88 (dd, 2H, J=9.2 and 45.6 Hz), 3.88 (m, 2H), 2.76 (t, 2H, J=5.6 Hz), 1.94 (t, 2H, J=6 Hz).

Procedure C: Reduction of 3-(5,6-dihydro-4H-pyrrolo[3,2,1-ij]quinolin-1-yl)-4(1H-indol-3-yl) pyrrole-2,5-dione by magnesium in methanol

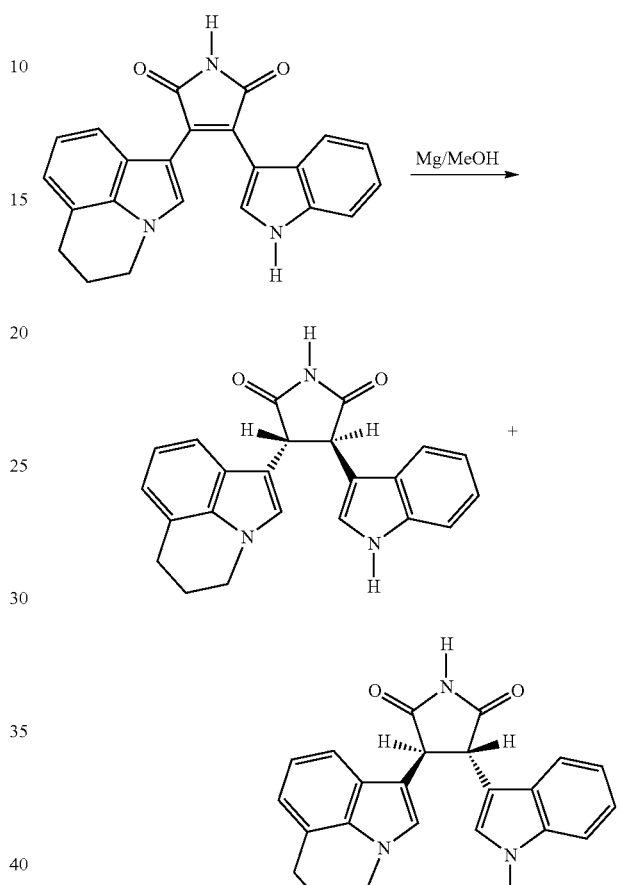

Magnesium turnings (3.05 g, 0.125 mol) were added to a solution of 3-(5,6-dihydro-4H-pyrrolo[3,2,1-ij]quinolin-1-yl)-4(1H-indol-3-yl)pyrrole-2,5-dione (2.56 g, 6.97 mmol) in anhydrous methanol (100 ml) and heated to reflux under an atmosphere of nitrogen for 40 minutes. After cooling to room temperature the mixture was poured into ethyl acetate (300 ml), washed with 1M hydrochloric acid (300 ml) and water (500 ml). The organic layer was dried over anhydrous sodium sulfate and evaporated to dryness. The residue was then purified by silica gel chromatography using 40-50% ethyl acetate in hexanes to yield (±)-trans-3-(5,6-dihydro-4H-pyrrolo[3,2,1-ij]quinolin-1-yl)-4(1H-indol-3-yl)pyrrolidine-2,5-dione as a pale pink solid (2.3 g). $^1$H NMR (DMSO-d$_6$) 400 MHz δ: 11.54 (s, 1H), 11.03 (s, 1H), 7.32-7.4 (m, 4H), 7.17 (d, 1H, J=7.2 Hz), 7.07 (t, 1H, J=7.6 Hz), 6.96 (t, 1H, J=7.6 Hz), 6.82-6.89 (m, 2H), 4.5 (dd, 2H, J=7.2 and 20 Hz), 4.07 (t, 2H, J=5.2 Hz), 2.87 (t, 2H, J=6 Hz), 2.08 (m, 2H).

Example 3

Preparation of (±)-Trans-3-(5,6-dihydro-4H-pyrrolo[3,2,1-ij]quinolin-1-yl)-4(1H-indol-3-yl) pyrrolidine-2,5-dione from (±)-Cis-3-(5,6-dihydro-4H-pyrrolo[3,2,1-ij]quinolin-1-yl)-4(1H-indol-3-yl)pyrrolidine-2,5-dione

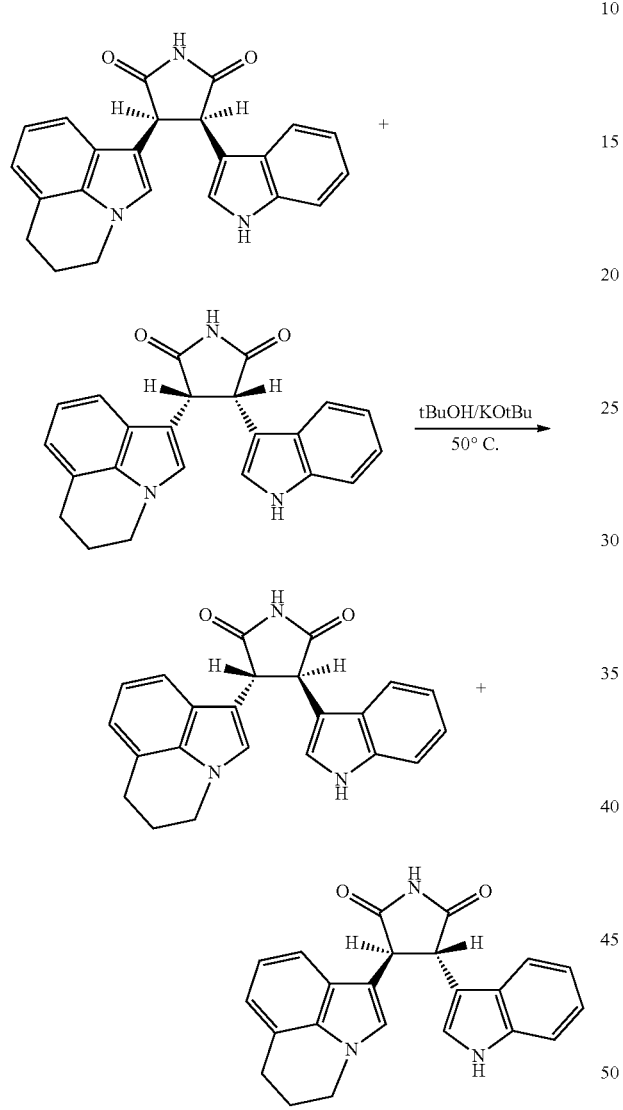

A preparation of (±)-cis-3-(5,6-dihydro-4H-pyrrolo[3,2,1-ij]quinolin-1-yl)-4(1H-indol-3-yl) pyrrolidine-2,5-dione (378 mg, 1.02 mmol) was heated to 50° C. in tert-butanol (10 ml) and potassium t-butoxide (11 mg, 98 μmol) for 16 hours. The mixture was poured into ethyl acetate (100 ml) and washed with water (100 ml). The organic layer was dried over anhydrous sodium sulfate and evaporated to dryness to give (±)-trans-3-(5,6-dihydro-4H-pyrrolo[3,2,1-ij]quinolin-1-yl)-4(1H-indol-3-yl)pyrrolidine-2,5-dione as a tan powder (276 mg). $^1$H NMR (DMSO-$d_6$) 400 MHz δ: 11.54 (s, 1H), 11.03 (s, 1H), 7.32-7.4 (m, 4H), 7.17 (d, 1H, J=7.2 Hz), 7.07 (t, 1H, J=7.6 Hz), 6.96 (t, 1H, J=7.6 Hz), 6.82-6.89 (m, 2H), 4.5 (dd, 2H, J=7.2 and 20 Hz), 4.07 (t, 2H, J=5.2 Hz), 2.87 (t, 2H, J=6 Hz), 2.08 (m, 2H).

Example 4

Chromatographic Separation of 3(R),4(S)-3-(5,6-Dihydro-4H-pyrrolo[3,2,1-ij]quinolin-1-yl)-4(1H-indol-3-yl)pyrrolidine-2,5-dione and 3(S),4(R)-3-(5,6-Dihydro-4H-pyrrolo[3,2,1-ij]quinolin-1-yl)-4(1H-indol-3-yl)pyrrolidine-2,5-dione

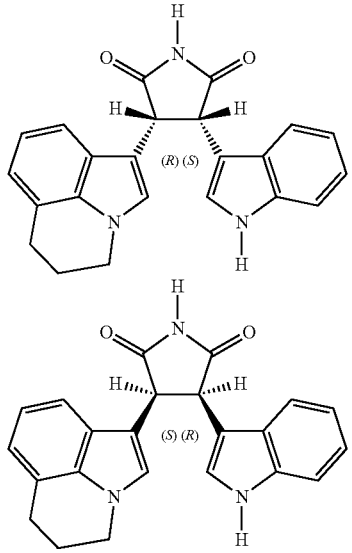

A mixture of (±)-cis-3-(5,6-dihydro-4H-pyrrolo[3,2,1-ij]quinolin-1-yl)-4(1H-indol-3-yl) pyrrolidine-2,5-dione (135 mg) in methanol (10 ml) and acetonitrile (6 ml) was subjected to preparative supercritical fluid chromatography, using a chiral AD column 20 mm×250 mm, eluting with 35% methanol/C02 at a flow rate of 3.5 ml/minutes. To give a faster eluting peak at 4.55 minutes (60 mg) assigned 3(R),4(S)-3-(5,6-dihydro-4H-pyrrolo[3,2,1-ij]quinolin-1-yl)-4(1H-indol-3-yl)pyrrolidine-2,5-dione and a slower eluting peak 6.05 minutes (56 mg), assigned 3(S),4(R)-3-(5,6-dihydro-4H-pyrrolo[3,2,1-ij]quinolin-1-yl)-4(1H-indol-3-yl)pyrrolidine-2,5-dione. The absolute stereochemical assignments were based solely upon the relative retention time of related compounds and may be reversed.

Example 5

Chromatographic Separation of 3(R),4(R)-3-(5,6-Dihydro-4H-pyrrolo[3,2,1-ij]quinolin-1-yl)-4(1H-indol-3-yl)pyrrolidine-2,5-dione and 3(S),4(S)-3-(5,6-Dihydro-4H-pyrrolo[3,2,1-ij]quinolin-1-yl)-4(1H-indol-3-yl) pyrrolidine-2,5-dione

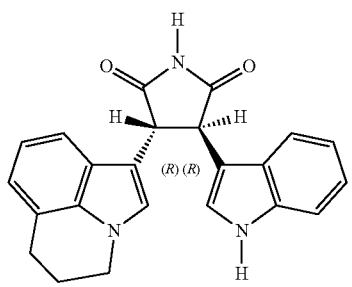

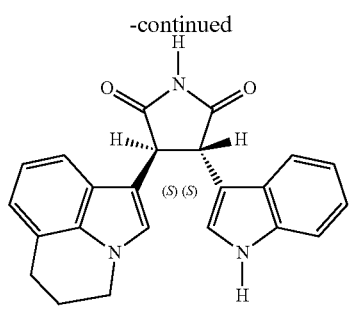

A mixture of (±)-trans-3-(5,6-dihydro-4H-pyrrolo[3,2,1-ij]quinolin-1-yl)-4(1H-indol-3-yl) pyrrolidine-2,5-dione (200 mg) in acetonitrile (1 ml) was subjected to preparative supercritical fluid chromatography using a CHIRALPAK® AD column (Daicel, U.S.A.) 20 mm×250 mm, eluting with 35% methanol/C02 at a flow rate of 3.5 ml/minutes. Chromatography yielded a faster eluting peak of the trans isomer (82 mg) having a negative optical rotation assigned (−)-3(R),4(R)-3-(5,6-dihydro-4H-pyrrolo[3,2,1-ij]quinolin-1-yl)-4(1H-indol-3-yl)pyrrolidine-2,5-dione and a slower eluting peak of the trans isomer (86 mg) having a positive optical rotation assigned (+)-3(S),4(R)-3-(5,6-dihydro-4H-pyrrolo[3,2,1-ij]quinolin-1-yl)-4(1H-indol-3-yl)pyrrolidine-2,5-dione. Absolute stereochemical assignments were based solely upon relative retention time of related compounds they may be reversed. All optical rotation measurements were conducted in chloroform at 25° C. at 589 nm.

Crystals of the chromatographically separated (+) or (−) isomers of trans-3-(5,6-dihydro-4H-pyrrolo[3,2,1-ij]quinolin-1-yl)-4(1H-indol-3-yl)pyrrolidine-2,5-dione may be prepared from 2,2,2-trifluoroethanol using vapor stress techniques and slow evaporation at 49° C. Crystals of these isomers may also be prepared from ethanol at room temperature by evaporation employing seed crystals, such as those prepared by vapor stress techniques.

Example 6

Preparation of 3-(5,6-dihydro-4H-pyrrolo[3,2,1-ij]quinolin-1-yl)-4(2-trifluoromethyl-phenyl)-pyrrole-2,5-dione 3-(5,6-Dihydro-4H-pyrrolo[3,2,1-ij]quinolin-1-yl)-4(2-trifluoromethyl-phenyl)-pyrrole-2,5-dione was prepared according to Example 1, steps 1-6, employing 2'-trifluoromethylphenyl acetamide in place of indole-3-acetamide in step 6. $^1$H NMR (CDCl$_3$) 400 MHz δ: 8.16 (s, 1H), 7.83 (d, 2H, J=7.2 Hz), 7.58 (m, 2H), 7.37 (d, 1H, J=7.6 Hz), 7.33 (s, 1H), 6.85 (d, 1H, J=6.8 Hz), 6.66 (t, 1H, J=7.2 Hz), 5.96 (d, 1H, J=8.8 Hz), 4.2 (t, 2H, J=5.6 Hz), 2.95 (t, 2H, J=6.4 Hz), 2.22 (m, 2H).

Example 7

Preparation of 3-(5,6-Dihydro-4H-pyrrolo[3,2,1-ij]quinolin-1-yl)-4-thiophen-2-yl-pyrrole-2,5-dione 3-(5,6-Dihydro-4H-pyrrolo[3,2,1-ij]quinolin-1-yl)-4-thiophen-2-yl-pyrrole-2,5-dione was prepared according to Example 1, steps 1-6, employing 2-thienylacetamide in place of indole-3-acetamide in step 6. $^1$H NMR (CDCl$_3$) 400 MHz δ: 7.87 (s, 1H), 7.49 (d, 1H, J=5.2 Hz), 7.37 (s, 1H), 7.3 (d, 1H, J=4 Hz), 7.02 (t, 1H, J=4 Hz), 6.89-6.98 (m, 2H), 6.53 (d, 1H, J=7.6 Hz), 4.92 (t, 2H, J=6 Hz), 3.04 (t, 2H, J=6 Hz), 2.31 (m, 2H).

Example 8

Preparation of 3-(5,6-Dihydro-4H-pyrrolo[3,2,1-ij]quinolin-1-yl)-4(3-methoxy-phenyl)-pyrrole-2,5-dione 3-(5,6-Dihydro-4H-pyrrolo[3,2,1-ij]quinolin-1-yl)-4(3-methoxy-phenyl)-pyrrole-2,5-dione was prepared according to Example 1, steps 1-6, employing 3-methoxyphenylacetamide in place of indole-3-acetamide in step 6. $^1$H NMR (CDCl$_3$) 400 MHz δ: 8.01 (s, 1H), 7.31 (s, 1H), 7.23 (t, 1H, J=7.6 Hz), 7.09 (m, 2H), 6.87-6.92 (m, 2H), 6.73 (t, 1H, J=7.6 Hz), 6.14 (d, 1H, J=8 Hz), 4.25 (t, 2H, J=5.2 Hz), 2.99 (t, 2H, J=5.6 Hz), 2.67 (m, 2H).

Example 9

Preparation of 3-(5,6-Dihydro-4H-pyrrolo[3,2,1-ij]quinolin-1-yl)-4-pyridin-2-yl-pyrrole-2,5-dione 3-(5,6-Dihydro-4H-pyrrolo[3,2,1-ij]quinolin-1-yl)-4-pyridin-2-yl-pyrrole-2,5-dione was prepared according to Example 1, steps 1-6, employing pyridin-2-ylacetamide in place of indole-3-acetamide in step 6. $^1$H NMR (CDCl$_3$) 400 MHz δ: 8.58 (d, 1H, J=4.4 Hz), 8.12 (s, 1H), 7.78 (dt, 1H, J=1.6 and 7.6 Hz), 7.68 (d, 1H, J=8 Hz), 7.31 (s, 1H), 7.25 (m, 1H), 6.87 (d, 1H, J=6 Hz), 6.68 (t, 1H, J=8 Hz), 5.91 (d, 1H, J=7.6 Hz), 4.24 (t, 2H, J=5.6 Hz), 2.97 (t, 2H, J=6 Hz), 2.25 (m, 2H).

Example 10

Preparation of 3-(5,6-Dihydro-4H-pyrrolo[3,2,1-ij]quinolin-1-yl)-4(4-methoxy-phenyl)-pyrrole-2,5-dione 3-(5,6-Dihydro-4H-pyrrolo[3,2,1-ij]quinolin-1-yl)-4(4-methoxy-phenyl)-pyrrole-2,5-dione was prepared according to Example 1, steps 1-6, employing 4-methoxyphenylacetamide in place of indole-3-acetamide in step 6. $^1$H NMR (CDCl$_3$) 400 MHz δ: 7.95 (s, 1H), 7.51 (m, 2H), 7.25 (s, 1H), 6.85-6.89 (m, 3H), 6.75 (t, 1H, J=8 Hz), 6.24 (d, 1H, J=8 Hz), 4.26 (t, 2H, J=5.6 Hz), 3.82 (s, 3H), 2.99 (t, 2H, J=6.4 Hz), 2.27 (m, 2H).

Example 11

Preparation of 3-Benzo[1,3]dioxol-5-yl-4-(5,6-dihydro-4H-pyrrolo[3,2,1-ij]quinolin-1-yl)-pyrrole-2,5-dione 3-Benzo[1,3]dioxol-5-yl-4-(5,6-dihydro-4H-pyrrolo[3,2,1-ij]quinolin-1-yl)-pyrrole-2,5-dione was prepared according to Example 1, steps 1-6, employing 3,4-(methylenedioxy)phenylacetamide in place of indole-3-acetamide in step 6. $^1$H NMR (CDCl$_3$) 400 MHz δ: 7.98 (s, 1H), 7.04-7.07 (m, 2H), 6.90 (d, 1H, J=7.2 Hz), 6.76-6.82 (m, 2H), 6.30 (d, 1H, J=8 Hz), 5.98 (s, 2H), 4.26 (t, 2H, J=5.6 Hz), 2.99 (t, 2H, J=6 Hz), 2.28 (m, 2H).

Example 12

Preparation of 3-(5,6-Dihydro-4H-pyrrolo[3,2,1-ij]quinolin-1-yl)-4-phenyl-pyrrole-2,5-dione 3-(5,6-Dihydro-4H-pyrrolo[3,2,1-ij]quinolin-1-yl)-4-phenyl-pyrrole-2,5-dione was prepared according to Example 1, steps 1-6, employing phenylacetamide in place of indole-3-acetamide in step 6. $^1$H NMR (CDCl$_3$) 400 MHz δ: 8.01 (s, 1H), 7.52 (m, 2H), 7.35 (m, 3H), 7.27 (s, 1H), 6.87 (d, 1H, J=7.2 Hz), 6.7 (t, 1H, J=7.2 Hz), 6.08 (d, 1H, J=8 Hz), 4.26 (t, 2H, J=5.6 Hz), 2.99 (t, 2H, J=5.6 Hz), 2.27 (m, 2H).

Example 13

Preparation of 3-Benzo[b]thiophen-2-yl-4-(5,6-dihydro-4H-pyrrolo[3,2,1-ij]quinolin-1-yl)-pyrrole-2,5-dione 3-Benzo[b]thiophen-2-yl-4-(5,6-dihydro-4H-pyrrolo[3,2,1-ij]quinolin-1-yl)-pyrrole-2,5-dione was prepared according to Example 1, steps 1-6, employing 2-benzothiophenylacetamide in place of indole-3-acetamide in step 6. $^1$H NMR (DMSO-d$_6$) 400 MHz δ: 11.11 (s, 1H), 8.14 (s, 1H), 8.01 (d, 1H, J=8 Hz), 7.84 (s, 1H), 7.45 (d, 1H, J=8 Hz), 7.3 (t, 1H, J=7.2 Hz), 7.15 (t, 1H, J=7.6 Hz), 6.71 (d, 1H, J=6.8 Hz), 6.43 (t, 1H, J=7.6 Hz), 5.99 (d, 1H, J=8 Hz), 4.26 (t, 2H, J=5.2 Hz), 2.86 (t, 2H, J=5.6 Hz), 2.1 (m, 2H).

Example 14

Preparation of 3-(5,6-Dihydro-4H-pyrrolo[3,2,1-ij]quinolin-1-yl)-4-(3-phenoxy-phenyl)-pyrrole-2,5-dione 3-(5,6-Dihydro-4H-pyrrolo[3,2,1-ij]quinolin-1-yl)-4-(3-phenoxy-phenyl)-pyrrole-2,5-dione was prepared according to Example 1, steps 1-6, employing 3-phenoxyphenylacetamide in place of indole-3-acetamide in step 6. $^1$H NMR (DMSO-d$_6$) 400 MHz δ: 11.03 (s, 1H), 8.01 (s, 1H), 7.43 (t, 1H, J=7.6 Hz), 7.28 (d, 1H, J=7.6 Hz), 7.15 (t, 2H, J=7.6 Hz), 7.03 (t, 2H, J=7.6 Hz), 6.92 (d, 1H, J=6.8 Hz), 6.8 (s, 1H), 6.76 (t, 1H, J=8 Hz), 6.60 (d, 2H, J=7.6 Hz), 6.08 (d, 1H, J=8 Hz), 4.27 (t, 2H, J=5.6 Hz), 2.97 (t, 2H, J=6 Hz), 2.16 (m, 2H).

Example 15

Preparation of 3-(5,6-Dihydro-4H-pyrrolo[3,2,1-ij]quinolin-1-yl)-4-(3-chloro-phenyl)-pyrrole-2,5-dione 3-(5,6-Dihydro-4H-pyrrolo[3,2,1-ij]quinolin-1-yl)-4-(3-chloro-phenyl)-pyrrole-2,5-dione was prepared according to Example 1, steps 1-6, employing 3-chlorophenylacetamide in place of indole-3-acetamide in step 6. $^1$H NMR (DMSO-d$_6$) 400 MHz δ: 11.11 (s, 1H), 8.13 (s, 1H), 7.47-7.43 (m, 2H), 7.36 (t, 1H, J=7.6 Hz), 7.29 (d, 1H, J=7.6 Hz), 6.86 (d, 1H, J=6.8 Hz), 6.68 (t, 1H, J=7.6 Hz), 5.97 (d, 1H, J=8 Hz), 4.31 (t, 2H, J=5.6 Hz), 2.93 (t, 2H, J=5.6 Hz), 2.16 (m, 2H).

Example 16

Preparation of 3-(5,6-Dihydro-4H-pyrrolo[3,2,1-ij]quinolin-1-yl)-4-(2-chloro-phenyl)-pyrrole-2,5-dione 3-(5,6-Dihydro-4H-pyrrolo[3,2,1-ij]quinolin-1-yl)-4-(2-chloro-phenyl)-pyrrole-2,5-dione was prepared according to Example 1, steps 1-6, employing 2-chlorophenylacetamide in place of indole-3-acetamide in step 6. $^1$H NMR (DMSO-d$_6$) 400 MHz δ: 11.1 (s, 1H), 8.17 (s, 1H), 7.55 (d, 1H, J=8 Hz), 7.45-7.49 (m, 1H), 7.36 (d, 2H, J=4.4 Hz), 6.81 (d, 1H, J=7.2 Hz), 6.58 (t, 1H, J=8 Hz), 5.92 (d, 1H, J=8.4 Hz), 4.27 (m, 2H), 2.89 (t, 2H, J=6 Hz), 2.11 (m, 2H).

Example 17

Preparation of 3-(5,6-Dihydro-4H-pyrrolo[3,2,1-ij]quinolin-1-yl)-4-(2,5-dimethoxy-phenyl)-pyrrole-2,5-dione 3-(5,6-Dihydro-4H-pyrrolo[3,2,1-ij]quinolin-1-yl)-4-(2,5-dimethoxy-phenyl)-pyrrole-2,5-dione was prepared according to Example 1, steps 1-6, employing 2,5-dimethoxyphenylacetamide in place of indole-3-acetamide in step 6. $^1$H NMR (DMSO-d$_6$) 400 MHz δ: 10.93 (s, 1H), 8.06 (s, 1H), 6.97 (s, 2H), 6.81 (d, 1H, J=7.6 Hz), 6.77 (s, 1H), 6.6 (t, 1H, J=8 Hz), 5.92 (d, 1H, J=8 Hz), 4.26 (t, 2H, J=5.2 Hz), 3.63 (s, 3H), 3.3 (s, 3H), 2.9 (t, 2H, J=5.6 Hz), 2.11 (m, 2H).

Example 18

Preparation of 3-(5,6-Dihydro-4H-pyrrolo[3,2,1-ij]quinolin-1-yl)-4-(2-chloro-4-fluoro-phenyl)-pyrrole-2,5-dione 3-(5,6-Dihydro-4H-pyrrolo[3,2,1-ij]quinolin-1-yl)-4-(2-chloro-4-fluoro-phenyl)-pyrrole-2,5-dione was prepared according to Example 1, steps 1-6, employing 2-chloro-4-fluorophenylacetamide in place of indole-3-acetamide in step 6. $^1$H NMR (DMSO-d$_6$) 400 MHz δ: 11.11 (s, 1H), 8.16 (s, 1H), 7.57 (dd, 1H, J=2.8 and 9.2 Hz), 7.44 (dd, 1H, J=6.8 and 8.4 Hz), 7.28 (dt, 1H, J=2.4 and 8.4 Hz), 6.84 (d, 1H, J=7.2 Hz), 6.66 (t, 1H, J=8 Hz), 5.98 (d, 1H, J=8 Hz), 4.27 (m, 2H), 2.9 (t, 2H, J=5.6 Hz), 2.11 (m, 2H).

Example 19

Preparation of 3-(5,6-Dihydro-4H-pyrrolo[3,2,1-ij]quinolin-1-yl)-4-naphthalene-1-yl-pyrrole-2,5-dione 3-(5,6-Dihydro-4H-pyrrolo[3,2,1-ij]quinolin-1-yl)-4-naphthalene-1-yl-pyrrole-2,5-dione was prepared according to Example 1, steps 1-6, employing 1-naphthylacetamide in place of indole-3-acetamide in step 6. $^1$H NMR (DMSO-d$_6$) 400 MHz δ: 11.1 (s, 1H), 8.17 (s, 1H), 8.02 (d, 1H, J=8 Hz), 7.97 (d, 1H, J=8 Hz), 7.75 (d, 1H, J=8 Hz), 7.43-7.55 (m, 3H), 7.37 (t, 1H, J=8 Hz), 6.66 (d, 1H, J=6.8 Hz), 6.27 (t, 1H, J=8 Hz), 5.57 (d, 1H, J=8 Hz), 4.24 (t, 2H, J=5.2 Hz), 2.83 (t, 2H, J=5.6 Hz), 2.08 (m, 2H).

Example 20

Preparation of 3-(5,6-Dihydro-4H-pyrrolo[3,2,1-ij]quinolin-1-yl)-4-(2,6-dichloro-phenyl)-pyrrole-2,5-dione 3-(5,6-Dihydro-4H-pyrrolo[3,2,1-ij]quinolin-1-yl)-4-(2,6-dichloro-phenyl)-pyrrole-2,5-dione was prepared according to Example 1, steps 1-6, employing 2,6-dichlorophenylacetamide in place of indole-3-acetamide in step 6. $^1$H NMR (DMSO-d$_6$) 400 MHz δ: 11.23 (s, 1H), 8.27 (s, 1H), 7.53-7.62 (m, 3H), 6.85 (d, 1H, J=7.2 Hz), 6.64 (t, 1H, J=8.4 Hz), 6.01 (d, 1H, J=8 Hz), 4.27 (t, 2H, J=5.6 Hz), 2.9 (t, 2H, J=5.6 Hz), 2.11 (m, 2H).

Example 21

Preparation of 3-(5,6-Dihydro-4H-pyrrolo[3,2,1-ij]quinolin-1-yl)-4-(2-bromo-phenyl)-pyrrole-2,5-dione 3-(5,6-Dihydro-4H-pyrrolo[3,2,1-ij]quinolin-1-yl)-4-(2-bromo-phenyl)-pyrrole-2,5-dione was prepared according to Example 1, steps 1-6, employing 2-bromophenylacetamide in place of indole-3-acetamide in step 6. $^1$H NMR (DMSO-$d_6$) 400 MHz δ: 11.09 (s, 1H), 8.17 (s, 1H), 7.75 (m, 1H), 7.37 (m, 2H), 7.33 (m, 1H), 6.81 (d, 1H, J=7.2 Hz), 6.58 (t, 1H, J=8 Hz), 5.95 (d, 1H, J=8 Hz), 4.26 (t, 2H, J=5.6 Hz), 2.9 (t, 2H, J=5.6 Hz), 2.11 (m, 2H).

Example 22

Preparation of 3-(5,6-Dihydro-4H-pyrrolo[3,2,1-ij]quinolin-1-yl)-4-indol-1-yl-pyrrole-2,5-dione 3-(5,6-Dihydro-4H-pyrrolo[3,2,1-ij]quinolin-1-yl)-4-indol-1-yl-pyrrole-2,5-dione was prepared according to Example 1, steps 1-6, employing N-indolyl-2-acetamide in place of indole-3-acetamide in step 6. $^1$H NMR (DMSO-$d_6$) 400 MHz δ: 11.21 (s, 1H), 8.18 (s, 1H), 7.58 (d, 1H, J=8 Hz), 7.52 (d, 1H, J=3.2 Hz), 7.01 (m, 2H), 6.91 (t, 1H, J=6.8 Hz), 6.74 (d, 1H, J=2.8 Hz), 6.71 (d, 1H, J=7.2 Hz), 6.4 (t, 1H, J=8 Hz), 5.63 (d, 1H, J=8 Hz), 4.28 (t, 2H, J=4.8 Hz), 2.85 (t, 2H, J=5.6 Hz), 2.11 (m, 2H).

Example 23

Preparation of 3-(5,6-Dihydro-4H-pyrrolo[3,2,1-ij]quinolin-1-yl)-4-pyridine-3-yl-pyrrole-2,5-dione 3-(5,6-Dihydro-4H-pyrrolo[3,2,1-ij]quinolin-1-yl)-4-pyridine-3-yl-pyrrole-2,5-dione was prepared according to Example 1, steps 1-6, employing pyridine-3-ylacetamide in place of indole-3-acetamide in step 6. $^1$H NMR (DMSO-$d_6$) 400 MHz δ: 11.14 (s, 1H), 8.53 (m, 2H), 8.12 (s, 1H), 7.78 (d, 1H, J=7.6 Hz), 7.41 (dd, 1H, J=4.8 and 8 Hz), 6.86 (d, 1H, J=7.2 Hz), 6.66 (t, 1H, J=7.6 Hz), 5.97 (d, 1H, J=8.4 Hz), 4.3 (t, 2H, J=5.2 Hz), 2.93 (t, 2H, J=5.6 Hz), 2.16 (m, 2H).

Example 24

Preparation of 3-(5,6-Dihydro-4H-pyrrolo[3,2,1-ij]quinolin-1-yl)-4-(5-bromo-1H-indol-3-yl)-pyrrole-2,5-dione 3-(5,6-Dihydro-4H-pyrrolo[3,2,1-ij]quinolin-1-yl)-4-(5-bromo-1H-indol-3-yl)-pyrrole-2,5-dione was prepared according to Example 1, steps 1-6, employing 5-bromo-1H-indolyl-3-ylacetamide in place of indole-3-acetamide in step 6. $^1$H NMR (DMSO-$d_6$) 400 MHz δ: 11.77 (s, 1H), 10.92 (s, 1H), 7.82 (s, 1H), 7.69 (d, 1H, J=2.4 Hz), 7.33 (d, 1H, J=8.4 Hz), 7.10 (dd, 1H, J=2 and 8.4 Hz), 6.99 (d, 1H, J=1.6 Hz), 6.76 (d, 1H, J=7.2 Hz), 6.55 (t, 1H, J=8 Hz), 6.36 (d, 1H, J=8 Hz), 4.25 (t, 2H, J=5.6 Hz), 2.92 (t, 2H, J=5.6 Hz), 2.17 (m, 2H).

Example 25

Preparation of 3-(5,6-Dihydro-4H-pyrrolo[3,2,1-ij]quinolin-1-yl)-4-pyridine-4-yl-pyrrole-2,5-dione 3-(5,6-Dihydro-4H-pyrrolo[3,2,1-ij]quinolin-1-yl)-4-pyridine-4-yl-pyrrole-2,5-dione was prepared according to Example 1, steps 1-6, employing pyridine-4-ylacetamide in place of indole-3-acetamide in step 6. $^1$H NMR (DMSO-$d_6$) 400 MHz δ: 11.17 (s, 1H), 8.53 (m, 2H), 8.54 (d, 2H, J=6 Hz), 8.17 (s, 1H), 7.32 (d, 2H, J=4.8 Hz), 6.88 (d, 1H, J=7.2 Hz), 6.69 (t, 1H, J=7.6 Hz), 5.93 (d, 1H, J=8 Hz), 4.31 (t, 2H, J=6 Hz), 2.94 (t, 2H, J=6 Hz), 2.16 (m, 2H).

Example 26

Preparation of 3-Biphenyl-4-yl-4-(5,6-dihydro-4H-pyrrolo[3,2,1-ij]quinolin-1-yl)-pyrrole-2,5-dione 3-Biphenyl-4-yl-4-(5,6-dihydro-4H-pyrrolo[3,2,1-ij]quinolin-1-yl)-pyrrole-2,5-dione was prepared according to Example 1, steps 1-6, employing 4-phenylphenylacetamide in place of indole-3-acetamide in step 6. $^1$H NMR (acetone-$d_6$) 400 MHz δ: 8.08 (s, 1H), 7.6-7.73 (m, 7H), 7.48 (t, 2H, J=6.8 Hz), 7.39 (d, 1H, J=7.2 Hz), 6.84 (d, 1H, J=8 Hz), 6.65 (t, 1H, J=8.4 Hz), 6.23 (t, 1H, J=7.2 Hz), 5.97 (d, 1H, J=8.4 Hz), 4.38 (m, 2H), 2.98 (m, 2H), 2.28 (m, 2H).

Example 27

Preparation of 3-(5,6-Dihydro-4H-pyrrolo[3,2,1-ij]quinolin-1-yl)-4-(4-methanesulfonyl-phenyl)-pyrrole-2,5-dione 3-(5,6-Dihydro-4H-pyrrolo[3,2,1-ij]quinolin-1-yl)-4-(4-methanesulfonyl-phenyl)-pyrrole-2,5-dione was prepared according to Example 1, steps 1-6, employing 4-methanesulfonylphenylacetamide in place of indole-3-acetamide in step 6. $^1$H NMR (CDCl$_3$) 400 MHz δ: 8.09 (s, 1H), 7.9 (d, 2H, J=8.4 Hz), 7.71 (d, 2H, J=8.4 Hz), 7.64 (s, 1H), 6.91 (d, 1H, J=7.2 Hz), 6.73 (t, 1H, J=7.6 Hz), 5.95 (d, 1H, J=8.4 Hz), 4.29 (t, 2H, J=5.6 Hz), 3.06 (s, 3H), 3.0 (t, 2H, J=6 Hz), 2.29 (m, 2H).

Example 28

Preparation of 3-(5,6-Dihydro-4H-pyrrolo[3,2,1-ij]quinolin-1-yl)-4-(2-trifluoromethyl-quinolin-4-yl-sulfanyl)-pyrrole-2,5-dione 3-(5,6-Dihydro-4H-pyrrolo[3,2,1-ij]quinolin-1-yl)-4-(2-trifluoromethyl-quinolin-4-yl-sulfanyl)-pyrrole-2,5-dione was prepared according to Example 1, steps 1-6, employing 2-[[2-(trifluoromethyl)-4-quinolinyl]thio]acetamide in place of indole-3-acetamide in step 6. $^1$H NMR (CDCl$_3$) 400 MHz δ: 8.3 (d, 1H, J=7.6 Hz), 8.11 (d, 1H, J=8.4 Hz), 8.05 (s, 1H), 7.68-7.82 (m, 4H), 7.23 (s, 1H), 6.83 (m, 2H), 4.21 (t, 2H, J=6 Hz), 2.92 (t, 2H, J=6 Hz), 2.21 (m, 2H).

Example 29

Preparation of 3-(4-Benzoyloxyphenyl)-4-(5,6-dihydro-4H-pyrrolo[3,2,1-ij]quinolin-1-yl)-pyrrole-2,5-dione 3-(4-Benzoyloxyphenyl)-4-(5,6-dihydro-4H-pyrrolo[3,2,1-ij]quinolin-1-yl)-pyrrole-2,5-dione was prepared according to Example 1, steps 1-6, employing 4-benzyloxyphenylacetamide in place of indole-3-acetamide in step 6. $^1$H NMR (CDCl$_3$) 400 MHz δ: 7.95 (s, 1H), 7.5 (d, 2H, J=8.8 Hz), 7.33-7.43 (m, 6H), 6.93 (d, 2H, J=8.8 Hz), 6.88 (d, 1H, J=7.2 Hz), 6.73 (t, 1H, J=7.2 Hz), 6.23 (d, 1H, J=8.4 Hz), 5.08 (s, 2H), 4.25 (t, 2H, J=5.6 Hz), 2.99 (t, 2H, J=6 Hz), 2.27 (m, 2H).

Example 30

Preparation of 3-(5,6-Dihydro-4H-pyrrolo[3,2,1-ij]quinolin-1-yl)-4-[4-(2-morpholin-4-yl-ethoxy)-phenyl]-pyrrole-2,5-dione 3-(5,6-Dihydro-4H-pyrrolo[3,2,1-ij]quinolin-1-yl)-4-[4-(2-morpholin-4-yl-ethoxy)-phenyl]-pyrrole-2,5-dione was prepared according to Example 1, steps 1-6, employing 4-(2-morpholin-4-yl-ethoxy)-phenylacetamide in place of indole-3-acetamide in step 6. $^1$H NMR (CDCl$_3$) 400 MHz δ: 7.95 (s, 1H), 7.48 (m, 3H), 6.86 (m, 3H), 6.74 (t, 1H, J=8 Hz), 6.23 (d, 1H, J=8. Hz), 4.26 (t, 2H, J=5.2 Hz), 4.16 (t, 2H, J=5.6 Hz), 3.77 (t, 4H, J=4.8 Hz), 2.99 (t, 2H, J=6 Hz), 2.87 (t, 2H, J=5.2 Hz), 2.65 (m, 4H), 2.28 (m, 2H).

Example 31

Preparation of 3-(5,6-Dihydro-4H-pyrrolo[3,2,1-ij]quinolin-1-yl)-4-(5-1-naphthyl-1H-indol-3-yl)pyrrole-2,5-dione A mixture of 1-naphthyl boronic acid (41 mg, 0.24 mmol), 3-(5,6-dihydro-4H-pyrrolo[3,2,1-ij]quinolin-1yl)-4-(5-bromo-1H-indol-3-yl)pyrrole-2,5-dione (88 mg, 0.2 mmol) (prepared as in Example 24), tetrakistriphenylphosphine palladium (5 mol %) in toluene (4 ml), ethanol (4 ml), saturated NaHCO$_3$ (1 ml), and water (2 ml) was heated at 100° C. under nitrogen for 5 hours. After cooling to room temperature, the mixture was extracted with ethyl acetate (3×15 ml) and concentrated. The residue was purified by silica gel chromatography, eluting with ethyl acetate/hexanes (1:4) to afford 3-(5,6-dihydro-4H-pyrrolo[3,2,1-ij]quinolin-1-yl)-4(5-1-naphthyl-1H-indol-3-yl)pyrrole-2,5-dione as a bright red solid (70 mg, 71%). $^1$H NMR (CD$_3$OD) δ: 1.80-1.92 (m, 2H), 2.72-2.80 (t, J=6.0 Hz, 2H), 3.94-3.99 (t, J=6.0 Hz, 2H), 6.50-6.58 (m, 3H), 6.66 (s, 1H), 6.72 (m, 1H), 6.98 (dd, J=8.4 Hz, J'=2.0 Hz, 1H), 7.00-7.50 (m, 2H), 7.28 (dd, J=6.8 Hz, J'=8.4 Hz, 1H), 7.38-7.43 (m, 2H), 7.61 (s, 1H), 7.72 (d, J=8.4 Hz, 1H), 7.82 (d, J=8.4 Hz, 1H), 7.97 (s, 1H).

Example 32

Preparation of 3-(5,6-Dihydro-4H-pyrrolo[3,2,1-ij]quinolin-1yl)-4-(5-phenyl-1H-indol-3-yl)pyrrole-2,5-dione 3-(5,6-Dihydro-4H-pyrrolo[3,2,1-ij]quinolin-1yl)-4-(5-phenyl-1H-indol-3-yl)pyrrole-2,5-dione was prepared according to the method of Example 31 employing phenyl boronic acid in place of 1-naphthyl boronic acid. $^1$H NMR (CD$_3$OD) δ: 2.10-2.18 (m, 2H), 2.90 (t, J=5.6 Hz, 2H), 4.18 (t, J=5.6 Hz, 2H), 6.63 (t, J=7.6 Hz, 1H), 6.75-6.83 (m, 5H), 7.11-7.20 (m, 3H), 7.22 (dd, J=8.4 Hz, J'=1.2 Hz, 1H), 7.38 (d, J=8.4 Hz, 1H), 7.59 (s, 1H), 7.93 (s, 1H).

Example 33

Preparation of 3-(5,6-Dihydro-4H-pyrrolo[3,2,1-ij]quinolin-1yl)-4-(5-(4-methoxyphenyl)-1H-indol-3-yl)pyrrole-2,5-dione 3-(5,6-Dihydro-4H-pyrrolo[3,2,1-ij]quinolin-1 yl)-4-(5-(4-methoxyphenyl)-1H-indol-3-yl) pyrrole-2,5-dione was prepared according to the method of Example 31 employing 4-methoxyphenyl boronic acid in place of 1-naphthyl boronic acid. $^1$H NMR (CD$_3$OD) δ: 2.09-2.18 (m, 2H), 2.90 (t, J=6.0 Hz, 2H), 4.15 (t, J=6.0 Hz, 2H), 6.62-6.68 (m, 2H), 6.73 (s, 4H), 6.77-6.82 (m, 2H), 7.18 (d, J=8.4 Hz, 1H), 7.33 (d, J=8.4 Hz, 1H), 7.53 (s, 1H), 7.91 (s, 1H).

Example 34

Preparation of 3-(5,6-Dihydro-4H-pyrrolo[3,2,1-ij]quinolin-1yl)-4-(5-(3-methylphenyl)-1H-indol-3-yl)pyrrole-2,5-dione 3-(5,6-Dihydro-4H-pyrrolo[3,2,1-ij]quinolin-1yl)-4-(5-(3-methylphenyl)-1H-indol-3-yl) pyrrole-2,5-dione was prepared according to the method of Example 31 employing 3-methylphenyl boronic acid in place of 1-naphthyl boronic acid. $^1$H NMR (CD$_3$OD) δ: 2.00-2.10 (m, 2H), 2.11 (s, 3H), 2.81-2.88 (t, J=6.0 Hz, 2H), 4.03-4.11 (t, J=5.6 Hz, 2H), 6.50 (d, J=7.2 Hz, 1H), 6.64 (t, J=7.6 Hz, 1H), 6.74-6.81 (m, 3H), 6.86 (d, J=8.0 Hz, 1H), 6.94 (d, J=7.6 Hz, 1H), 7.03 (t, J=7.2 Hz, 1H), 7.22 (dd, J=8.4 Hz, J'=2.0 Hz, 1H), 7.36 (d, J=8.8 Hz, 1H), 7.48 (s, 1H), 7.90 (s, 1H).

Example 35

Preparation of (±)-Trans-3-(5,6-dihydro-4H-pyrrolo[3,2,1-ij]quinolin-1yl)-4-(5-bromo-1H-indol-3-yl)pyrrolidine-2,5-dione 3-(5,6-dihydro-4H-pyrrolo[3,2,1-ij]quinolin-1yl)-4-(5-bromo-1H-indol-3-yl)pyrrole-2,5-dione, prepared as in Example 24, was reduced with Mg in methanol as described in Example 2, Procedure C, to yield (±)-trans-3-(5,6-dihydro-4H-pyrrolo[3,2,1-ij]quinolin-1 yl)-4-(5-bromo-1H-indol-3-yl)pyrrolidine-2,5-dione. $^1$H NMR (CD$_3$OD) δ: 2.18-2.26 (m, 2H), 2.96 (t, J=6.0 Hz, 2H), 4.12 (t, J=6.4 Hz, 2H), 4.40 (d, J=6.8 Hz, 1H), 4.52 (d, J=6.8 Hz, 1H), 6.86-6.96 (m, 2H), 7.08 (s, 1H), 7.13-7.30 (m, 5H)

Example 36

Preparation of (±)-Trans-3-(5,6-dihydro-4H-pyrrolo[3,2,1-ij]quinolin-1yl)-4-(5-phenyl-1H-indol-3-yl)pyrrolidine-2,5-dione 3-(5,6-Dihydro-4H-pyrrolo[3,2,1-ij]quinolin-1yl)-4-(5-phenyl-1H-indol-3-yl)pyrrole-2,5-dione, prepared as in Example 32, was reduced with Mg in methanol as described in Example 2, Procedure C, to yield (±)-trans-3-(5,6-dihydro-4H-pyrrolo[3,2,1-ij]quinolin-1yl)-4-(5-phenyl-1H-indol-3-yl)pyrrolidine-2,5-dione. $^1$H NMR (CD$_3$OD) δ: 2.00-2.16 (m, 2H), 2.94 (t, J=6.0 Hz, 2H), 3.92-3.99 (m, 1H), 4.00-4.08 (m, 1H), 4.36 (d, J=6.4 Hz, 1H), 4.68 (d, J=6.4 Hz 1H), 6.88-6.97 (m, 2H), 7.04 (s, 1H), 7.12-7.15 (m, 1H), 7.17-7.47 (m, 9H).

Example 37

Preparation of (±)-Trans-3-(5,6-dihydro-4H-pyrrolo[3,2,1-ij]quinolin-1yl)-4-(5-(1-naphthyl)-1H-indol-3-yl)pyrrolidine-2,5-dione 3-(5,6-Dihydro-4H-pyrrolo[3,2,1-ij]quinolin-1yl)-4-(5-1-naphthyl-1H-indol-3-yl)pyrrole-2,5-dione, prepared as in Example 31, was reduced with Mg in methanol as described in Example 2, Procedure C, to yield (±)-trans-3-(5,6-dihydro-4H-pyrrolo[3,2,1-ij]quinolin-1yl)-4-(5-(1-naphthyl)-1H-indol-3-yl)pyrrolidine-2,5-dione. $^1$H NMR (CD$_3$OD) δ: 1.85-1.95 (m, 1H), 1.95-2.05 (m, 1H), 2.74-2.88 (m, 2H), 3.72-3.83 (m, 1H), 3.88-3.98 (m, 1H), 4.40 (d, J=6.4 Hz, 1H), 4.62 (d, J=6.4 Hz, 1H), 6.80 (d, J=6.8 Hz, 1H), 6.78 (t, J=8.0 Hz, 1H), 7.46 (s, 1H), 7.07-7.13 (m, 2H), 7.18-7.23 (dd, J=8.4 Hz, J=1.6 Hz, 2H), 7.27-7.34 (m, 2H), 7.41-7.49 (m, 3H), 7.78-7.83 (dd, J=8.4 Hz, J=3.2 Hz, 2H), 7.86-7.90 (d, J=7.6 Hz, 1H).

Example 38

Preparation of (±)-Trans-3-(5,6-dihydro-4H-pyrrolo[3,2,1-ij]quinolin-1yl)-4-(5-(4-methoxyphenyl)-1H-indol-3-yl) pyrrolidine-2,5-dione 3-(5,6-Dihydro-4H-pyrrolo[3,2,1-ij]quinolin-1yl)-4-(5-(4-methoxyphenyl)-1H-indol-3-yl) pyrrole-2,5-dione, prepared as in Example 33, was reduced with Mg in methanol as described in Example 2, Procedure C, to yield (±)-trans-3-(5,6-dihydro-4H-pyrrolo[3,2,1-ij]quinolin-1yl)-4-(5-(4-methoxyphenyl)-1H-indol-3-yl)pyrrolidine-2,5-dione. $^1$H NMR (CD$_3$OD) a: 2.03-2.22 (m, 2H), 2.98 (t, J=6.0 Hz, 2H), 3.80 (s, 3H), 3.97-4.06 (m, 1H), 4.06-4.14 (m, 1H), 4.38 (d, J=6.8 Hz, 1H), 4.67 (d, J=6.8 Hz, 1H), 6.86 (d, J=8.4 Hz, 2H), 6.91-7.00 (m, 2H), 7.08 (s, 2H), 7.17-7.27 (m, 4H), 7.31 (d, J=8.4 Hz, 1H), 7.37 (d, J=8.8 Hz, 1H).

Example 39

(±)-Trans-3-(5,6-dihydro-4H-pyrrolo[3,2,1-ij]quinolin-1yl)-4-(5-(3-methylphenyl)-1H-indol-3-yl)pyrrolidine-2,5-dione 3-(5,6-Dihydro-4H-pyrrolo[3,2,1-ij]quinolin-1yl)-4-(5-(3-methylphenyl)-1H-indol-3-yl) pyrrole-2,5-dione, prepared as in Example 34, was reduced with Mg in methanol as described in Example 2, Procedure C, to yield (±)-trans-3-(5,6-dihydro-4H-pyrrolo[3,2,1-ij]quinolin-1yl)-4-(5-(3-methylphenyl)-1H-indol-3-yl)pyrrolidine-2,5-dione. $^1$H NMR (CD$_3$OD) δ: 1.98-2.18 (m, 2H), 2.34 (s, 3H), 2.85-3.00 (m, 2H), 3.90-3.98 (m, 1H), 3.98-4.09 (m, 1H), 4.35 (d, J=7.2 Hz, 1H), 4.64 (d, J=6.8 Hz, 1H), 6.88-6.99 (m, 2H), 7.00-7.10 (m, 3H), 7.13-7.26 (m, 5H), 7.36 (m, 2H).

Example 40

Preparation of (±)-Trans-3-(5,6-dihydro-4H-pyrrolo[3,2,1-ij]quinolin-1yl)-4-(2-chloro-4-fluorophenyl)pyrrolidine-2,5-dione To a solution of 5,6-dihydro-4H-pyrrolo[3,2,1-ij]quinolin-1-yl)oxoacetic acid methyl ester (0.243 g, 1 mmol) and 2-chloro-4-fluorophenylacetamide (1 mmol) in anhydrous tetrahydrofuran (5 ml) at 0° C. was added a solution of potassium t-butoxide (1 M in tetrahydrofuran) (2.5 ml, 2.5 mmol). The mixture was stirred at 0° C. for 2 hours. Concentrated hydrochloric acid (0.5 ml) was then added and the mixture stirred for 1 hour at room temperature. The mixture was then diluted with ethyl acetate (20 ml), washed with water (2×15 ml) and saturated aqueous sodium chloride solution (15 ml). The organic layer was then dried over anhydrous sodium sulfate and concentrated under reduced pressure to yield an oil. This residue was diluted in anhydrous methanol (15 ml) and the resulting solution charged with oven dried magnesium turnings (0.5 g, 20.5 mmol) and stirred at 70° C. in a ventilated vial until the Mg turnings fully dissolved or for two hours. The vial was then allowed to cool to room temperature. The mixture was diluted with ethyl acetate (25 ml) and washed with 10% hydrochloric acid (2×25 m) and saturated aqueous sodium chloride solution (20 ml). The organic layer was dried over anhydrous sodium sulfate and concentrated under reduced pressure. The residue was purified by silica gel chromatography, eluting with an ethyl acetate/hexanes gradient (10% ethyl acetate to 50% ethyl acetate over 40 minutes) to yield (25.6 mg, 6.7%) of (±)-trans-3-(5,6-dihydro-4H-pyrrolo[3,2,1-ij]quinolin-1yl)-4-(2-chloro-4-fluorophenyl)pyrrolidine-2,5-dione. $^1$H NMR (DMSO-d$_6$) 400 MHz δ: 12.5 (s, 1H), 7.52 (t, 1H, J=6.4 Hz), 7.49 (dd, 1H, J=6.4 2.4 Hz), 7.34 (s, 1H), 7.21 (td, 1H, J=6.0 2.8 Hz), 7.10 (d, 1H, J=7.6 Hz), 6.87 (m, 2H), 4.67 (d, 1H, J=8.0 Hz), 4.51 (d, 1H, J=7.2 Hz), 2.90 (t, 2H, J=5.6 Hz), 2.11 (t, 2H, J=5.2 Hz).

Example 41

Preparation of (±)-Trans-3-(5,6-dihydro-4H-pyrrolo[3,2,1-ij]quinolin-1yl)-4-(2,6-dichlorophenyl) pyrrolidine-2,5-dione (±)-Trans-3-(5,6-dihydro-4H-pyrrolo[3,2,1-ij]quinolin-1yl)-4-(2,6-dichlorophenyl) pyrrolidine-2,5-dione was prepared according to Example 40 replacing 2-chloro-4-fluorophenylacetamide with 2,6-dichlorophenylacetamide. Yield 52.2 mg, 13.0%. $^1$H NMR (DMSO-d$_6$) 400 MHz δ: 11.82 (s, 1H), 7.34 (m, 3H), 7.10 (d, 1H, J=7.2 Hz), 6.87 (m, 2H), 5.16 (d, 1H J=7.6 Hz), 5.10 (d, 1H, J=7.6 Hz), 2.91 (t, 2H, J=6.0 Hz) 2.10 (m, 2H).

Example 42

Preparation of (±)-Trans-3-(5,6-dihydro-4H-pyrrolo[3,2,1-ij]quinolin-1yl)-4-(4-bromophenyl)pyrrolidine-2,5-dione (±)-Trans-3-(5,6-dihydro-4H-pyrrolo[3,2,1-ij]quinolin-1yl)-4-(4-bromophenyl)pyrrolidine-2,5-dione was prepared according to Example 40 replacing 2-chloro-4-fluorophenylacetamide with 4-bromophenylacetamide. Yield 33.1 mg, 8.1%. $^1$H NMR (DMSO-d$_6$) 400 MHz δ: 11.55 (s, 1H), 7.53 (dt, 2H, J=8.8 2.0 Hz), 7.34 (dt, 3H, J=8.0 2.0 Hz), 7.15 (dd, 1H, J=7.6 1.0 Hz), 6.86 (m, 2H), 4.53 (d, 1H, J=8.0 Hz), 4.37 (d, 1H, J=8.0 Hz), 4.10 (t, 2H, J=1.6 Hz), 2.90 (t, 2H, J=2.0 Hz), 2.12 (t, 2H, J=1.8 Hz).

Example 43

Preparation of (±)-Trans-3-(5,6-dihydro-4H-pyrrolo[3,2,1-ij]quinolin-1yl)-4-(4-chlorophenyl) pyrrolidine-2,5-dione (±)-Trans-3-(5,6-dihydro-4H-pyrrolo[3,2,1-ij]quinolin-1yl)-4-(4-chlorophenyl)pyrrolidine-2,5-dione was prepared according to Example 40 replacing 2-chloro-4-fluorophenylacetamide with 4-chlorophenylacetamide. Yield 32.7 mg, 9.0%. $^1$H NMR (DMSO-$d_6$) 400 MHz δ: 11.54 (s, 1H), 7.40 (m, 4H), 7.33 (s, 1H), 7.15 (dd, 1H, J=6.8 0.8 Hz), 6.86 (m, 2H), 4.54 (d, 1H, J=8.0 Hz), 7.38 (d, 1H, J=7.6 Hz), 4.10 (t, 2H, J=5.6 Hz), 2.90 (t, 2H, J=6.0 Hz), 2.11 (m, 2H).

Example 44

Preparation of (±)-Trans-3-(5,6-dihydro-4H-pyrrolo[3,2,1-ij]quinolin-1yl)-4-(4-trifluoromethoxyphenyl)pyrrolidine-2,5-dione (±)-Trans-3-(5,6-dihydro-4H-pyrrolo[3,2,1-ij]quinolin-1yl)-4-(4-trifluoromethoxyphenyl) pyrrolidine-2,5-dione was prepared according to Example 40 replacing 2-chloro-4-fluorophenylacetamide with 4-trifluoromethoxyphenylacetamide. Yield 67.8 mg, 16.4%. $^1$H NMR (DMSO-$d_6$) 400 MHz δ: 11.56 (s, 1H), 7.52 (d, 2H, J=8.4 Hz), 7.35 (s, 1H), 7.33 (d, 2H, J=8.0 Hz), 7.15 (d, 1H, J=7.2 Hz), 6.86 (m, 2H), 4.58 (d, 1H, J=8.0 Hz), 4.45 (d, 1H, J=8.0 Hz), 4.10 (t, 2H, J=6.0 Hz), 2.90 (t, 2H, J=6.0), 2.10 (t, 2H, J=5.6).

Example 45

Preparation of (±)-Trans-3-(5,6-dihydro-4H-pyrrolo[3,2,1-ij]quinolin-1yl)-4-(thiophen-3-yl)pyrrolidine-2,5-dione (±)-Trans-3-(5,6-dihydro-4H-pyrrolo[3,2,1-ij]quinolin-1yl)-4-(thiophen-3-yl)pyrrolidine-2,5-dione was prepared according to Example 40 replacing 2-chloro-4-fluorophenylacetamide with thiophen-3-ylacetamide. Yield 50.3 mg, 15.0%. $^1$H NMR (DMSO-$d_6$) 400 MHz δ: 11.50 (s, 1H), 7.52 (m, 1H), 7.49 (m, 1H), 7.35 (s, 1H), 7.21 (dd, 1H, J=4.0 1.2 Hz), 7.16 (d, 1H, 7.6 Hz), 6.89 (d, 1H, J=4.4 Hz), 6.85 (t, 1H, J=6.8 Hz), 4.56 (d, 1H, J=7.2 Hz), 4.41 (d, 1H, J=7.2 Hz), 4.10 (t, 2H, J=6.0 Hz), 2.90 (t, 2H, J=6.0 Hz), 2.10 (m, 2H).

Example 46

Preparation of (±)-Trans-3-(5,6-dihydro-4H-pyrrolo[3,2,1-ij]quinolin-1yl)-4-(2-fluorophenyl) pyrrolidine-2,5-dione (±)-Trans-3-(5,6-dihydro-4H-pyrrolo[3,2,1-ij]quinolin-1yl)-4-(2-fluorophenyl)pyrrolidine-2,5-dione was prepared according to Example 40 replacing 2-chloro-4-fluorophenylacetamide with 2-fluorophenylacetamide. Yield 30.6 mg, 8.8%. $^1$H NMR (DMSO-$d_6$) 400 MHz δ: 11.64 (s, 1H), 7.36 (m, 3H), 7.17 (m, 3H), 6.84 (m, 2H), 4.44 (d, 1H, J=7.2 Hz), 4.40 (d, 1H, J=7.6 Hz), 4.10 (s, 2H), 2.88 (s, 2H), 2.09 (s, 2H).

Example 47

Preparation of (±)-Trans-3-(5,6-dihydro-4H-pyrrolo[3,2,1-ij]quinolin-1yl)-4-(2-thiophen-2-yl)pyrrolidine-2,5-dione (±)-Trans-3-(5,6-dihydro-4H-pyrrolo[3,2,1-ij]quinolin-1yl)-4-(2-thiophen-2-yl)pyrrolidine-2,5-dione was prepared according to Example 40 replacing 2-chloro-4-fluorophenylacetamide with 2-thiophen-2-ylacetamide. Yield 30.6 mg, 8.8%. $^1$H NMR (DMSO-$d_6$) 400 MHz δ: 11.58 (s, 1H), 7.45 (dd, 1H, J=5.2 0.8 Hz), 7.40 (s, 1H), 7.22 (d, 1H, J=8.0 Hz), 7.12 (d, 1H, J=3.2 Hz), 6.99 (dd, 1H, J=5.2 and 3.6 Hz), 4.63 (d, 1H, J=8.0 Hz), 4.60 (d, 1H, J=7.6 Hz), 2.90 (t, 2H, J=6.0 Hz), 2.12 (t, 2H, J=6.0 Hz).

Example 48

Preparation of (±)-Trans-3-(5,6-dihydro-4H-pyrrolo[3,2,1-ij]quinolin-1yl)-4-(2,4-dichlorophenyl)pyrrolidine-2,5-dione (±)-Trans-3-(5,6-dihydro-4H-pyrrolo[3,2,1-ij]quinolin-1yl)-4-(2,4-dichlorophenyl) pyrrolidine-2,5-dione was prepared according to Example 40 replacing 2-chloro-4-fluorophenylacetamide with 2,4-dichlorophenylacetamide. Yield 20.9 mg, 5.2%. $^1$H NMR (DMSO-$d_6$) 400 MHz δ: 11.65 (s, 1H), 7.69 (s, 1H), 7.51 (d, 1H, J=8.0 Hz), 7.43 (d, 1H, J=8.0 Hz), 7.34 (s, 1H), 7.12 (m, 1H), 6.87 (m, 2H), 4.65 (d, 1H, J=7.6 Hz), 4.55 (d, 1H, J=7.6 Hz), 4.10 (t, 2H, J=6.0 Hz), 2.90 (t, 2H, J=6.0), 2.12 (t, 2H, J=6.0 Hz).

Example 49

Preparation of (±)-Trans-3-(5,6-dihydro-4H-pyrrolo[3,2,1-ij]quinolin-1yl)-4-phenyl-pyrrolidine-2,5-dione (±)-Trans-3-(5,6-dihydro-4H-pyrrolo[3,2,1-ij]quinolin-1yl)-4-phenyl-pyrrolidine-2,5-dione was prepared according to the Example 40 replacing 2-chloro-4-fluorophenylacetamide with phenylacetamide. $^1$H NMR (DMSO-$d_6$) 400 MHz δ: 11.511 (s, 1H), 7.24-7.36 (m, 6H), 7.13 (d, 1H, J=7.2), 6.8-6.88 (m, 2H), 4.49 (d, 1H, J=8.0 Hz), 4.3 (d, 1H, J=7.6 Hz), 4.08 (m, 2H), 2.88 (m, 2H), 2.088 (m, 2H).

Example 50

Preparation of (±)-Trans-3-(5,6-dihydro-4H-pyrrolo[3,2,1-ij]quinolin-1yl)-4-(2-chlorophenyl)-pyrrolidine-2,5-dione (±)-Trans-3-(5,6-dihydro-4H-pyrrolo[3,2,1-ij]quinolin-1yl)-4-(2-chlorophenyl)-pyrrolidine-2,5-dione was prepared according to Example 40 replacing 2-chloro-4-fluorophenylacetamide with 2-chlorophenylacetamide. $^1$H NMR (DMSO-$d_6$) 400 MHz δ: 11.655 (s, 1H), 7.41-7.48 (m, 2H), 7.27-7.35 (m, 3H, J=7.2), 7.87 (d, 1H, J=7.6), 6.81-6.88 (m, 2H), 4.632 (d, 1H, J=7.6 Hz), 4.494 (d, 1H, J=7.2), 4.07-4.10 (m, 2H), 2.884 (m, 2H), 2.09 (m, 2H).

Example 51

Preparation of (±)-Trans-3-(5,6-dihydro-4H-pyrrolo[3,2,1-ij]quinolin-1yl)-4-(N-methylindol-3-yl)pyrrolidine-2,5-dione (±)-Trans-3-(5,6-dihydro-4H-pyrrolo[3,2,1-ij]quinolin-1yl)-4-(N-methylindol-3-yl) pyrrolidine-2,5-dione was prepared according to Example 40 replacing 2-chloro-4-fluorophenylacetamide with N-methylindol-3-ylacetamide. $^1$H NMR (DMSO-$d_6$) 400 MHz δ: 11.55 (s, 1H), 7.44-7.34 (m, 4H), 7.2-7.18 (m, 2H), 7.01 (t, 1H), 6.82-6.89 (m, 2H), 4.49 (dd, 2H), 4.093 (t, 2H), 4.093 (t, 2H), 3.73 (s, 3H), 2.89 (t, 2H), 2.07 (m, 2H).

Example 52

Preparation of (+)-Cis-3-(5,6-dihydro-4H-pyrrolo[3,2,1-ij]quinolin-1yl)-4-(4-methoxyphenyl)-pyrrolidine-2,5-dione 3-(5,6-Dihydro-4H-pyrrolo[3,2,1-ij]quinolin-1-yl)-4(4-methoxy-phenyl)-pyrrole-2,5-dione, prepared as in Example 10 and was reduced by employing the method of Example 2, Protocol B, to yield (±)-cis-3-(5,6-dihydro-4H-pyrrolo[3,2,1-ij]quinolin-1yl)-4-(4-methoxyphenyl)-pyrrolidine-2,5-dione. $^1$H NMR (CDCl$_3$) 400 MHz δ: 8.62 (s, 1H), 7.15 (d, 1H, J=7.6 Hz), 6.8-6.93 (m, 4H), 6.7 (s, 1H), 6.55 (d, 2H, J=8.4 Hz), 4.8 (d, 1H, J=8.8 Hz), 4.48 (d, 1H, J=8.8 Hz), 3.96 (m, 2H), 3.63 (s, 3H), 2.87 (t, 2H, J=6 Hz), 2.10 (m, 2H).

Example 53

Preparation of (±)-Cis-3-(5,6-dihydro-4H-pyrrolo[3,2,1-ij]quinolin-1yl)-4-(2,5-dimethoxyphenyl)-pyrrolidine-2,5-dione 3-(5,6-Dihydro-4H-pyrrolo[3,2,1-ij]quinolin-1-yl)-4-(2,5-dimethoxy-phenyl)-pyrrole-2,5-dione, prepared as in Example 17, was reduced by employing the method of Example 2, Protocol B, to yield (±)-cis-3-(5,6-dihydro-4H-pyrrolo[3,2,1-ij]quinolin-1yl)-4-(2,5-dimethoxyphenyl)-pyrrolidine-2,5-dione. $^1$H NMR (CDCl$_3$) 400 MHz δ: 8.0 (s, 1H), 7.19 (d, 1H, J=7.6 Hz), 6.89 (t, 1H, J=7.2 Hz), 6.77 (d, 2H, J=7.2 Hz), 6.44-6.51 (m, 3H), 4.84 (d, 2H, J=9.6 Hz), 3.88-4.00 (m, 2H), 3.6 (s, 3H), 3.49 (s, 3H), 2.8 (m, 2H), 2.05 (m, 2H).

Example 54

Preparation of (±)-Cis-3-(5,6-dihydro-4H-pyrrolo[3,2,1-ij]quinolin-1yl)-4-(2-chloro-4-fluoro-phenyl)-pyrrolidine-2,5-dione 3-(5,6-Dihydro-4H-pyrrolo[3,2,1-ij]quinolin-1-yl)-4-(2-chloro-4-fluoro-phenyl)-pyrrole-2,5-dione, prepared as in Example 18, was reduced by employing the method of Example 2, Protocol B, to yield (±)-cis-3-(5,6-dihydro-4H-pyrrolo[3,2,1-ij]quinolin-1yl)-4-(2-chloro-4-fluoro-phenyl)-pyrrolidine-2,5-dione. $^1$H NMR (DMSO-d$_6$) 400 MHz δ: 11.82 (s, 1H), 7.02-7.18 (m, 4H), 6.7-6.85 (m, 3H), 5.01 (d, 1H, J=9.2 Hz), 4.79 (d, 2H, J=9.6 Hz), 3.96 (m, 2H), 2.79 (m, 2H), 1.97 (m, 2H).

Example 55

Preparation of (±)-Cis-3-(5,6-dihydro-4H-pyrrolo[3,2,1-ij]quinolin-1yl)-4-(3-chlorophenyl)-pyrrolidine-2,5-dione 3-(5,6-Dihydro-4H-pyrrolo[3,2,1-ij]quinolin-1-yl)-4-(3-chloro-phenyl)-pyrrole-2,5-dione, prepared as in Example 15, was reduced by employing the method of Example 2, Procedure B, to yield (±)-cis-3-(5,6-dihydro-4H-pyrrolo[3,2,1-ij]quinolin-1yl)-4-(3-chlorophenyl)-pyrrolidine-2,5-dione. $^1$H NMR (DMSO-d$_6$) 400 MHz δ: 11.66 (s, 1H), 7.13 (d, 1H, J=8 Hz), 6.95-7.02 (m, 5H), 6.78 (t, 1H, J=7.6 Hz), 6.7 (d, 1H, J=7.2 Hz), 4.84 (d, 1H, J=9.2 Hz), 4.65 (d, 2H, J=8.8 Hz), 3.9-4.03 (m, 2H), 2.79 (t, 2H, J=5.6 Hz), 1.97 (m, 2H).

Example 56

Preparation of (±)-Phosphoric acid mono-[trans-3-(5,6-dihydro-4H-pyrrolo[3,2,1-ij]quinolin-1-yl)-4-(1H-indol-3-yl)-2,5-dioxo-pyrrolidin-1-ylmethyl] ester Step 1

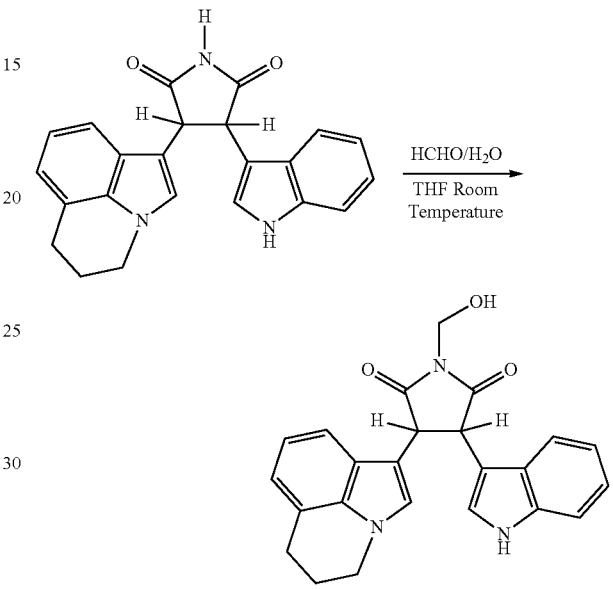

(±)-Trans-3-(5,6-dihydro-4H-pyrrolo[3,2,1-ij]quinolin-1-yl)-4(1H-indol-3-yl)pyrrolidine-2,5-dione (3.0 g, 8.13 mmol, prepared as in Example 2, Procedure C) and formaldehyde (30 ml, 37% in water) in tetrahydrofuran (30 ml) were stirred for 14-16 hours at room temperature. The mixture was then taken up in ethyl acetate (50 ml) and water (50 ml). The organic layer was washed with brine and dried over sodium sulfate. Solvent was removed under reduced pressure and residue was purified using a silica gel chromatography column eluted with EtOAc/Hexane 1:1 to yield 2.5 g, 77%, of (+)-trans-3-(5,6-dihydro-4H-pyrrolo[3,2,1-ij]quinolin-1-yl)-1-hydroxymethyl-4-(1H-indol-3-yl)-pyrrolidine-2,5-dione an orange foamy solid (2.5 g, 77%).

Step 2

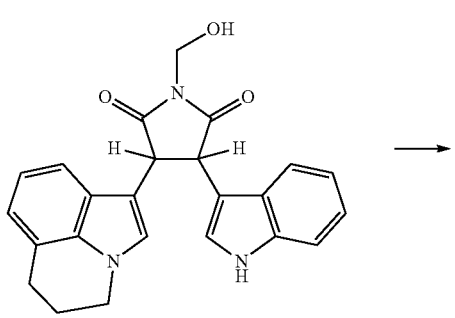

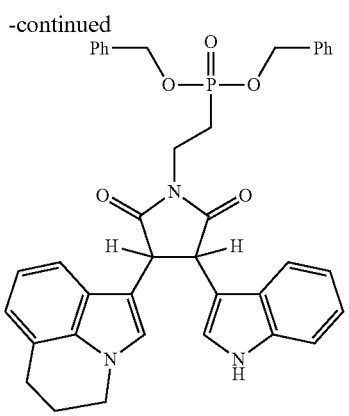

(±)-Trans-3-(5,6-Dihydro-4H-pyrrolo[3,2,1-ij]quinolin-1-yl)-1-hydroxymethyl-4-(1H-indol-3-yl)-pyrrolidine-2,5-dione (0.06 g) in anhydrous tetrahydrofuran (5 ml) was treated with dibenzylphosphoramidate (0.156 ml, 3.5 equivalents) followed by the addition of tetrazole (3% solution in acetonitrile, 2 ml). The reaction mixture was stirred at room temperature for 20 min and cooled to −78° C. A solution of m-chloroperbenzoic acid (70%, 0.162 g) in dichloromethane (2 ml) was added at −78° C. After 5 min at −78° C., the reaction was brought to room temperature and stirred for 5 min. Solvents were removed under reduced pressure and the residue was purified by flash chromatography on a silica column, eluted with ethyl acetate, hexane to give phosphoric acid dibenzyl ester trans-3-(5,6-dihydro-4H-pyrrolo[3,2,1-ij]quinolin-1-yl)-4-(1H-indol-3-yl)-2,5-dioxo-pyrrolidin-1-ylmethyl ester as a solid (70 mg). $^1$H NMR (DMSO-d$_6$) 400 MHz δ: 11.10 (s, 1H), 7.32-7.39 (m, 12H), 6.84-7.24 (m, 2H), 5.49 (brs, 2H), 5.03 (m, 4H), 4.61 (dd, 2H), 4.06 (brs, 2H), 2.87 (brs, 2H), 2.07 (brs, 2H).

Step 3

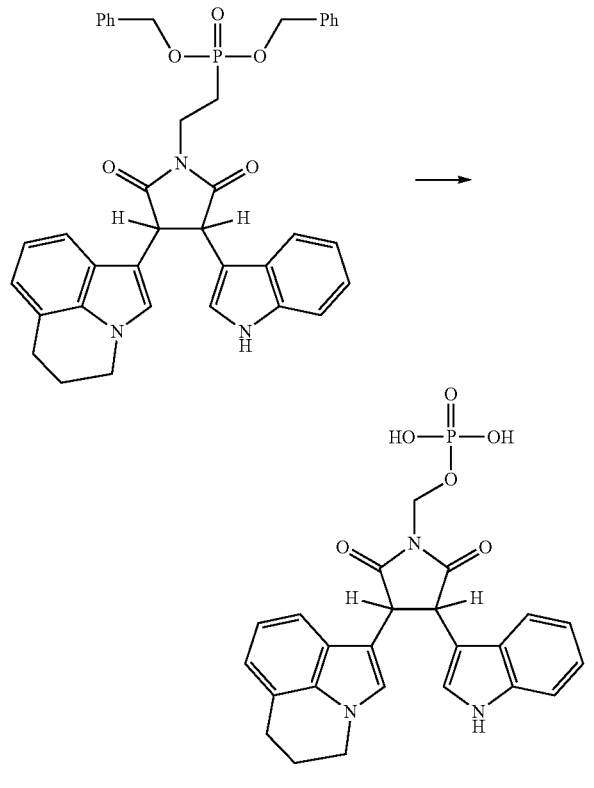

The phosphoric acid dibenzyl ester of (±)-trans-3-(5,6-dihydro-4H-pyrrolo[3,2,1-ij]quinolin-1-yl)-4-(1H-indol-3-yl)-2,5-dioxo-pyrrolidin-1-yl-methyl ester (0.160 g) in methanol (2 ml) and Pd/C (10%, 20 mg) was stirred at room temperature under 1 atmosphere of hydrogen for two hours. The mixture was filtered over Celite and the solvent removed to give (±)-phosphoric acid mono-[trans-3-(5,6-dihydro-4H-pyrrolo[3,2,1-ij]quinolin-1-yl)-4-(1H-indol-3-yl)-2,5-dioxo-pyrrolidin-1-ylmethyl]ester (0.110 g).

Example 57

Preparation of (±)-trans-2-Amino-propionic acid-3-(5,6-dihydro-4H-pyrrolo[3,2,1-ij]quinolin-1-yl)-4-(1H-indol-3-yl)-2,5-dioxo-pyrrolidin-1-yl methyl ester Step 1

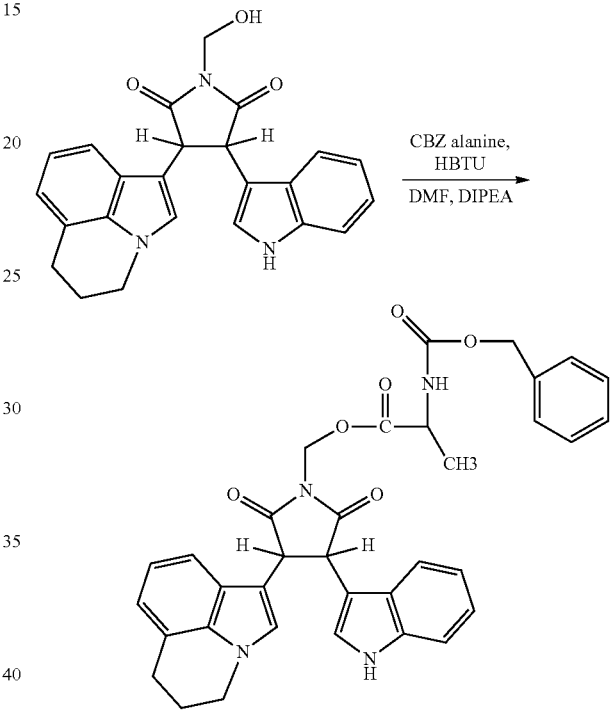

To a solution of (±)-trans-3-(5,6-dihydro-4H-pyrrolo[3,2,1-ij]quinolin-1-yl)-1-hydroxymethyl-4-(1H-indol-3-yl)-pyrrolidine-2,5-dione (0.5 mmol) in tetrahydrofuran (8 ml) was added N-carbobenzyloxy alanine (1.1 equivalents) followed by the addition of HBTU (1.5 equivalents) and DIPEA (2.2 equivalents). The mixture was stirred at room temperature for 15 h. The solvents were removed under reduced pressure and the residue was taken up in ethyl acetate and water (1:1, 15 ml). The organic layer was separated and dried. The residue was purified by silica gel chromatography to provide the N-carbobenzyloxy protected product.

Step 2

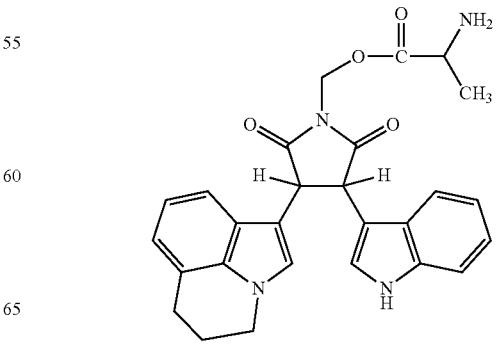

A solution of the N-carbobenzyloxy protected product from Step 1 (0.5 mmol) in methanol (8 ml) and a few drops of 4 M HCl in ethyl acetate and 10% Pd/C (10% w/w) were stirred at room temperature under 1 atmosphere of hydrogen for 2 hours. The mixture was then filtered over celite and the solvent removed to provide final product (±)-trans-2-aminopropionic acid-3-(5,6-dihydro-4H-pyrrolo[3,2,1-ij]quinolin-1-yl)-4-(1H-indol-3-yl)-2,5-dioxo-pyrrolidin-1-ylmethyl ester. $^1$H NMR (DMSO-$d_6$) 400 MHz δ: 11.10 (s, 1H), 8.57 (s, 2H), 6.84-7.41 (m, 9H), 5.61 (m, 2H), 4.62 (dd, 2H), 4.07 (brs, 2H), 3.72 (brm, 1H), 2.87 (brs, 2H), 2.23 (s, 6H), 2.08 (brs, 2H), 1.40 (d, J=6.4 Hz, 3H).

Example 58

Preparation of (±)-trans-2-Amino-acetic acid-3-(5,6-dihydro-4H-pyrrolo[3,2,1-ij]quinolin-1-yl)-4-(1H-indol-3-yl)-2,5-dioxo-pyrrolidin-1-yl methyl ester (±)-trans-2-Amino-acetic acid-3-(5,6-dihydro-4H-pyrrolo[3,2,1-ij]quinolin-1-yl)-4-(1H-indol-3-yl)-2,5-dioxo-pyrrolidin-1-ylmethyl ester was prepared as in Example 57 by replacing N-carbobenzyloxy alanine with N-carbobenzyloxy glycine. $^1$H NMR (DMSO-$d_6$) 400 MHz δ: 11.19 (s, 1H), 8.46 (s, 2H), 6.82-7.43 (m, 9H), 5.61 (s, 2H), 4.65 (dd, 2H), 4.08 (brt, J=5.6 Hz, 2H), 3.88 (brs, 2H), 2.87 (t, J=5.6 Hz, 2H), 2.48 (s, 2H), 2.08 (t, J=4.8 Hz, 2H).

Example 59

Preparation of (±)-trans-2-dimethylamino-acetic acid-3-(5,6-dihydro-4H-pyrrolo[3,2,1-ij]quinolin-1-yl)-4-(1H-indol-3-yl)-2,5-dioxo-pyrrolidin-1-ylmethyl ester To a solution of (±)-trans-3-(5,6-Dihydro-4H-pyrrolo[3,2,1-ij]quinolin-1-yl)-1-hydroxymethyl-4-(1H-indol-3-yl)-pyrrolidine-2,5-dione (0.5 mmol) in tetrahydrofuran (8 ml) was added N,N-dimethylglycine (1.1 equivalents) followed by the addition of HBTU (1.5 equivalents) and DIPEA (N,N-diisopropylethylamine, 2.2 equivalents). The mixture was stirred at room temperature for 15 hours. The solvents were removed under reduced pressure and the residue was taken up in ethyl acetate and water (1:1, 15 ml). The organic layer was separated and dried to yield a residue. The residue was purified by chromatography on a silica gel column eluted with ethyl acetate hexanes to yield (±)-trans-2-dimethylamino-acetic acid-3-(5,6-dihydro-4H-pyrrolo[3,2,1-ij]quinolin-1-yl)-4-(1H-indol-3-yl)-2,5-dioxo-pyrrolidin-1-yl methyl ester. $^1$H NMR (DMSO-$d_6$) 400 MHz δ: 11.10 (s, 1H), 6.82-7.41 (m, 9H), 5.70 (m, 2H), 4.62 (dd, 2H), 4.07 (brs, 2H), 3.23 (s, 2H), 2.87 (brs, 2H), 2.23 (s, 6H), 2.08 (brs, 2H).

Example 60

Preparation of (±)-trans-Isonicotinic acid-3-(5,6-dihydro-4H-pyrrolo[3,2,1-ij]quinolin-1-yl)-4-(1H-indol-3-yl)-2,5-dioxo-pyrrolidin-1-ylmethyl ester (±)-trans-Isonicotinic acid 3-(5,6-dihydro-4H-pyrrolo[3,2,1-ij]quinolin-1-yl)-4-(1H-indol-3-yl)-2,5-dioxo-pyrrolidin-1-ylmethyl ester was prepared as in Example 59 by replacing N,N-dimethylglycine with 4-carboxypyridine. $^1$H NMR (DMSO-$d_6$) 400 MHz δ: 11.19 (s, 1H), 8.83 (d, 2H), 7.83 (d, 2H), 6.83-7.42 (m, 9H), 5.88 (s, 2H), 4.65 (dd, 2H), 4.05 (brt, 2H), 2.86 (brs, 2H), 2.08 (brs, 2H).

Example 61

Preparation of 3-(5,6-dihydro-4H-pyrrolo[3,2,1-ij]quinolin-1-yl)-4(1-methylindol-3-yl)-1-methyl pyrrole-2,5-dione and (±)-cis-3-(5,6-dihydro-4H-pyrrolo[3,2,1-ij]quinolin-1-yl)-4(1-methylindol-3-yl)-1-methyl pyrrolidine-2,5-dione Step 1: To a solution of 3-(5,6-dihydro-4H-pyrrolo[3,2,1-ij]quinolin-1-yl)-4(1H-indol-3-yl)pyrrole-2,5-dione (100 mg, see Example 1) in anhydrous dimethylformamide (5 ml) was added potassium carbonate (0.5 g) and methyl iodide (0.1 ml). The mixture was stirred at room temperature for 48 hours then poured into ethyl acetate (100 ml), washed with water (100 ml), dried over anhydrous sodium sulfate and evaporated to give 3-(5,6-dihydro-4H-pyrrolo[3,2,1-ij]quinolin-1-yl)-4(1-methylindol-3-yl)-1-methyl pyrrole-2,5-dione as a red solid (93 mg).

Step 2: To a solution of 3-(5,6-dihydro-4H-pyrrolo[3,2,1-ij]quinolin-1-yl)-4(1-methylindol-3-yl)-1-methyl pyrrole-2,5-dione (93 mg) in methanol (5 ml) and ethylacetate (5 ml) was added 10% Pd—C (50 mg) and the mixture stirred at room temperature under 1 atmosphere of hydrogen for 48 hours. Toluene (50 ml) was added and the mixture again stirred at room temperature under 1 atmosphere of hydrogen for 2 hours. The mixture was then filtered through a pad of celite and evaporated to dryness to yield a residue. The residue was purified using silica gel chromatography eluting with 35-40% ethylacetate in hexanes to give (±)-cis-3-(5,6-dihydro-4H-pyrrolo[3,2,1-ij]quinolin-1-yl)-4(1-methylindol-3-yl)-1-methyl pyrrolidine-2,5-dione as a pale yellow solid (53 mg). $^1$H NMR (CDCl$_3$) 400 MHz δ: 7.23 (s, 1H), 7.05-7.07 (m, 2H), 7.01 (d, 1H, J=7.2 Hz), 6.92-6.97 (m, 1H), 6.85 (t, 1H, J=7.2 Hz), 6.74 (d, 1H, J=6.8 Hz), 6.64 (d, 2H, J=6.4 Hz), 4.78 (m, 2H), 3.75-3.84 (m, 2H), 3.45 (s, 3H), 3.27 (s, 3H), 2.79 (t, 2H, J=5.6 Hz), 1.98 (m, 2H).

Example 62

Preparation of (±)-Trans-3-(5,6-dihydro-4H-pyrrolo[3,2,1-ij]quinolin-1-yl)-4(1H-indol-3-yl)pyrrolidine-2,5-dione (±)-Trans-3-(5,6-dihydro-4H-pyrrolo[3,2,1-ij]quinolin-1-yl)-4(1H-indol-3-yl)pyrrolidine-2,5-dione may be prepared by reacting 1H-indole and 3,4-dibromo-1-phenyl-pyrrole-2,5-dione in the presence of methyl magnesium bromide to yield 3-bromo-4-(1H-indol-3-yl)-1-phenyl-pyrrole-2,5-dione. The 3-bromo-4-(1H-indol-3-yl)-1-phenyl-pyrrole-2,5-dione is subsequently reacted with 5,6-dihydro-4H-pyrrolo[3,2,1-ij]quinoline and LiHMDS (lithium hexamethyldisilane) in toluene or (5,6-dihydro-4H-pyrrolo[3,2,1-ij]quinolin-1-yl)-boranediol and Pd(PPh$_3$)$_4$(tetrakis (triphenylphosphine)palladium) to yield 3-(5,6-dihydro-4H-pyrrolo[3,2,1-ij]quinolin-1-yl)-4-(1H-indol-3-yl)-1-phenyl-pyrrole-2,5-dione, which is reduced and deprotected by treatment with Mg in methanol, as in Example 2 procedure C, followed by catalytic hydrogenation over palladium on carbon to yield (±)-trans-3-(5,6-dihydro-4H-pyrrolo[3,2,1-ij]quinolin-1-yl)-4(1H-indol-3-yl)pyrrolidine-2,5-dione. Bnz is benzyl.

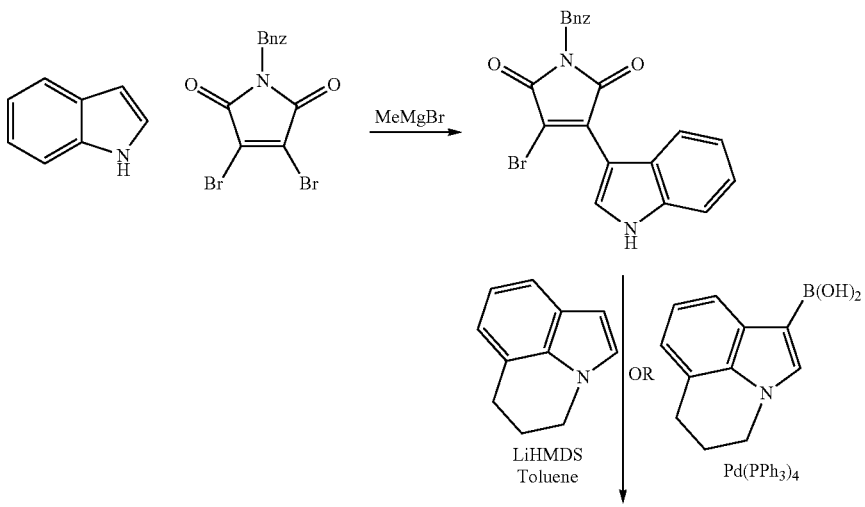

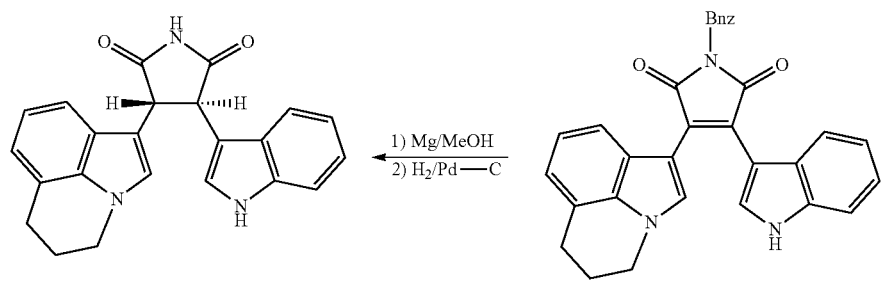

Example 63

Preparation of (±)-Trans-3-(5,6-dihydro-4H-pyrrolo[3,2,1-ij]quinolin-1-yl)-4(1H-indol-3-yl) pyrrolidine-2,5-dione (±)-Trans-3-(5,6-dihydro-4H-pyrrolo[3,2,1-ij]quinolin-1-yl)-4(1H-indol-3-yl)pyrrolidine-2,5-dione may be prepared by reacting 1-allyl-7-bromo-1H-indole with (COCl)₂ (oxalyl chloride) and sodium methoxide in a polar aprotic solvent such as dichloromethane to yield (1-allyl-7-bromo-1H-indol-3-yl)-oxo-acetic acid methyl ester, which is subsequently reacted with 2-(1H-indol-3-yl)-acetamide and tBuOK (potassium tert-butoxide) in THF to yield 3-(1-allyl-7-bromo-1H-indol-3-yl)-4-(1H-indol-3-yl)-pyrrole-2,5-dione. Reduction of the 3-(1-allyl-7-bromo-1H-indol-3-yl)-4-(1H-indol-3-yl)-pyrrole-2,5-dione by Mg in refluxing methanol, as in Example 2 procedure C, yields 3-(1-allyl-7-bromo-1H-indol-3-yl)-4-(1H-indol-3-yl)-pyrrolidine-2,5-dione, which is treated with 9-BBN (9-borabicyclo[3.3.1]nonane) and Pd(PPh₃)₄(tetrakis(triphenylphosphine) palladium) to yield (±)-trans-3-(5,6-dihydro-4H-pyrrolo[3,2,1-ij]quinolin-1-yl)-4(1H-indol-3-yl)pyrrolidine-2,5-dione.

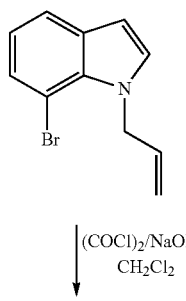

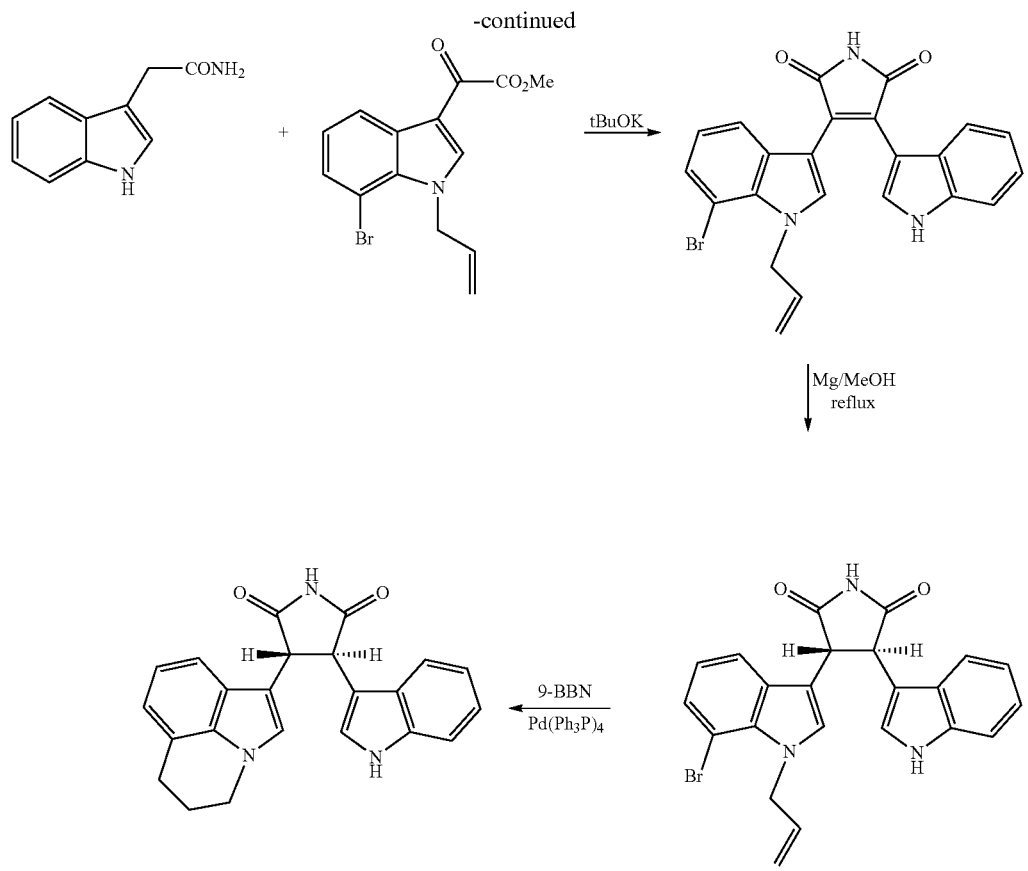

Example 64

Preparation of (+)-Cis-3-(5,6-dihydro-4H-pyrrolo[3,2,1-ij]quinolin-1-yl)-4(1H-indol-3-yl)pyrrolidine-2,5-dione and (±)-Trans-3-(5,6-dihydro-4H-pyrrolo[3,2,1-ij]quinolin-1-yl)-4(1H-indol-3-yl)pyrrolidine-2,5-dione The cis and trans isomers of 3-(5,6-dihydro-4H-pyrrolo[3,2,1-ij]quinolin-1-yl)-4(1H-indol-3-yl)pyrrolidine-2,5-dione may be prepared beginning with the reaction of (1H-indol-3-yl)-oxo-acetic acid methyl ester and (5,6-dihydro-4H-pyrrolo[3,2,1-ij]quinolin-1-yl)-acetic acid methyl ester in the presence of a base such as LDA (lithium diisopropylamide) in a polar aprotic solvent such as THF to yield 2-(5,6-dihydro-4H-pyrrolo[3,2,1-ij]quinolin-1-yl)-3-(1H-indol-3-yl)-but-2-enedioic acid dimethyl ester. Alternatively, 2-(5,6-dihydro-4H-pyrrolo[3,2,1-ij]quinolin-1-yl)-3-(1H-indol-3-yl)-but-2-enedioic acid dimethyl ester may be prepared by reaction of (1H-indol-3-yl)-acetic acid methyl ester and (5,6-dihydro-4H-pyrrolo[3,2,1-ij]quinolin-1-yl)-oxo-acetic acid methyl ester in the presence of a base (e.g., LDA) in THF. The 2-(5,6-dihydro-4H-pyrrolo[3,2,1-ij]quinolin-1-yl)-3-(1H-indol-3-yl)-but-2-enedioic acid dimethyl ester is reduced by catalytic hydrogenation over a noble metal catalyst (e.g., Pd on charcoal) to give 2-(5,6-dihydro-4H-pyrrolo[3,2,1-ij]quinolin-1-yl)-3-(1H-indol-3-yl)-succinic acid dimethyl ester, which is reacted with benzylamine (PhCH$_2$NH$_2$) to yield a mixture of cis and trans 3-(5,6-dihydro-4H-pyrrolo[3,2,1-ij]quinolin-1-yl)-4-(1H-indol-3-yl)-1-phenyl-pyrrolidine-2,5-dione. The mixture of cis and trans isomers may be deprotected by catalytic hydrogenation over Pd on charcoal (Pd—C) to give rise to a mixture of cis and trans 3-(5,6-dihydro-4H-pyrrolo[3,2,1-ij]quinolin-1-yl)-4-(1H-indol-3-yl)-pyrrolidine-2,5-dione. The cis and trans isomers may be separated to give all four cis and trans isomers (e.g., by chromatography as in Examples 4 and 5). The deprotected mixture of cis and trans isomers may be treated with potassium tert-butoxide in tert-butanol (as in Example 3) or a mixture of THF and tert-butanol at 50° C. to yield a mixture with a predominance of the trans isomers. Alternatively, the 2-(5,6-dihydro-4H-pyrrolo[3,2,1-ij]quinolin-1-yl)-3-(1H-indol-3-yl)-succinic acid dimethyl ester can be reacted with ammonia in methanol at elevated temperatures to yield predominantly the cis isomers of 3-(5,6-dihydro-4H-pyrrolo[3,2,1-ij]quinolin-1-yl)-4-(1H-indol-3-yl)-pyrrolidine-2,5-dione, which may be isomerized to yield predominately the trans isomers of 3-(5,6-dihydro-4H-pyrrolo[3,2,1-ij]quinolin-1-yl)-4-(1H-indol-3-yl)-pyrrolidine-2,5-dione with potassium tert-butoxide in tert-butanol (as in Example 3) or a mixture of THF and tert-butanol at 50° C.

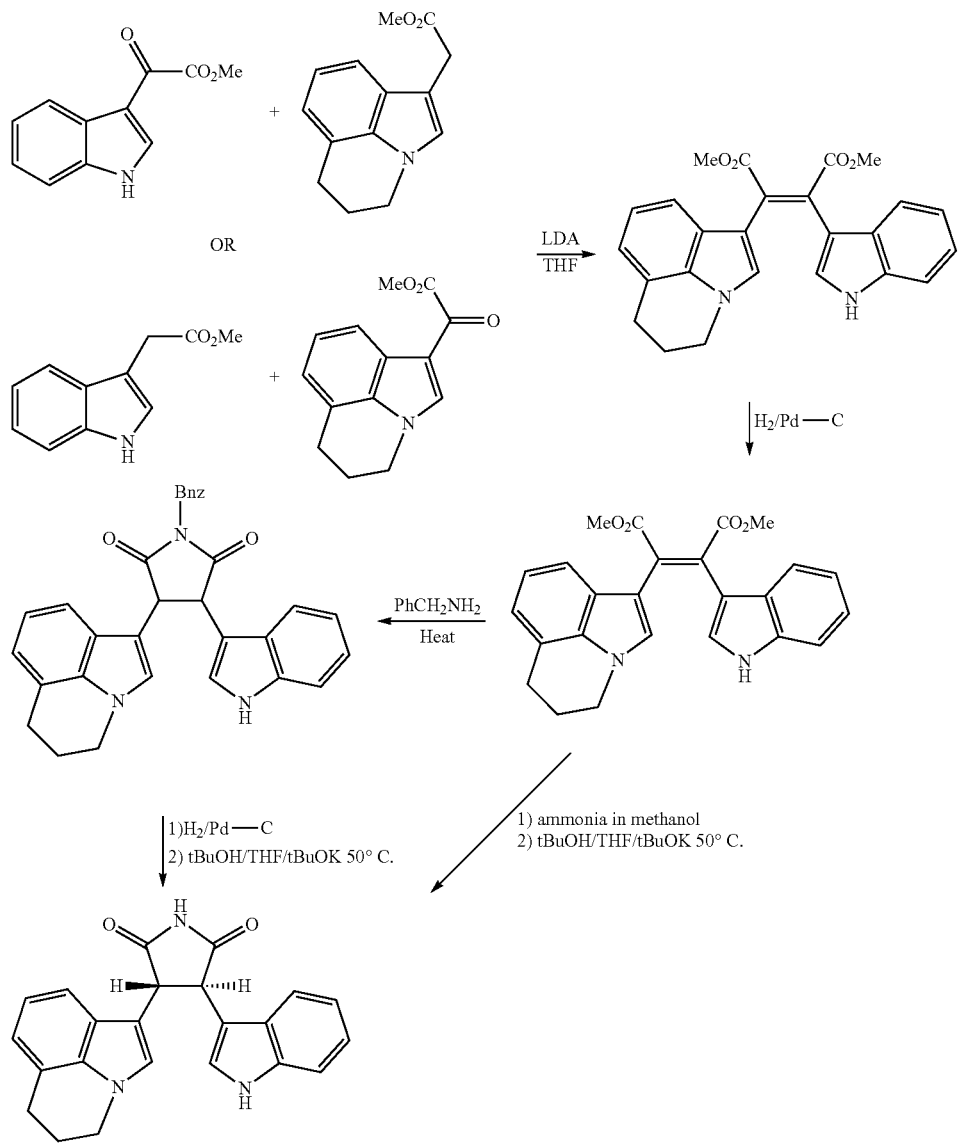

Example 65

Preparation of 3-(5,6-dihydro-4H-pyrrolo[3,2,1-ij]quinolin-1-yl)-4-(3-methoxyphenyl)-1H-pyrrole-2,5-dione To a mixture of 5,6-dihydro-4H-pyrrolo[3,2,1-ij]quinolin-1-yl)oxoacetic acid methyl ester (0.50 g, 2.05 mmol) and 2-(3-methoxyphenyl)acetamide (0.37 g, 2.26 mmol) in anhydrous tetrahydrofuran (5 mL) was added potassium tert-butoxide (1.0 M in tetrahydrofuran, 6.17 mL, 6.17 mmol) dropwise at 0° C. The mixture was stirred at 0° C. for 3 hours then concentrated hydrochloric acid (1.5 mL) was added at 0° C. The resulting mixture was stirred for 1 hour, diluted with ethyl acetate (150 mL), washed with water (2×50 mL), dried over anhydrous sodium sulfate and concentrated to give 0.91 g of an orange solid. The residue was purified by column chromatography eluting with 20-40% ethyl acetate in hexane to give 3-(5,6-dihydro-4H-pyrrolo[3,2,1-ij]quinolin-1-yl)-4-(3-methoxyphenyl)-1H-pyrrole-2,5-dione. Mp 99-101° C.; $^1$H NMR (CDCl$_3$) 400 MHz δ: 8.01 (s, 1H), 7.81 (bs, 1H), 7.20-7.25 (m, 1H), 7.06-7.08 (m, 2H), 6.85-6.91 (m, 2H), 7.25 (t, 1H), 6.13 (d, J=8.0 Hz, 1H), 4.24 (t, 2H), 3.66 (s, 3H), 2.97 (t, J=6.0 Hz, 2H), 2.22-2.26 (m, 2H).

Example 66

Preparation of 3-[4-(benzyloxy)phenyl]-4-(5,6-dihydro-4H-pyrrolo[3,2,1-ij]quinolin-1-yl)-1H-pyrrole-2,5-dione 3-[4-(benzyloxy)phenyl]-4-(5,6-dihydro-4H-pyrrolo[3,2,1-ij]quinolin-1-yl)-1H-pyrrole-2,5-dione was prepared according to Example 65, employing 2-(4-(benzyloxy)phenyl)acetamide in place of 2-(3-methoxyphenyl)acetamide. Mp 262-265° C.; $^1$H NMR (DMSO-d$_6$) 400 MHz δ: 10.96 (s, 1H), 8.01 (d, 1H), 7.33-7.45 (m, 7H), 6.99 (d, J=6.8 Hz, 2H), 6.83 (d, J=7.2 Hz, 1H), 6.63 (t, 1H), 6.09 (d, J=8.4 Hz, 1H), 5.13 (s, 2H), 4.27 (m, 2H), 2.92 (m, 2H), 2.15 (m, 2H).

Example 67

Preparation of 3-(5,6-dihydro-4H-pyrrolo[3,2,1-ij]quinolin-1-yl)-4-(4-fluorophenyl)-1H-pyrrole-2,5-dione 3-(5,6-dihydro-4H-pyrrolo[3,2,1-ij]quinolin-1-yl)-4-(4-fluorophenyl)-1H-pyrrole-2,5-dione was prepared according to Example 65, employing 2-(4-fluorophenyl)acetamide in place of 2-(3-methoxyphenyl)acetamide. Mp 234-235° C.; $^1$H NMR (DMSO-$d_6$) 400 MHz δ: 11.05 (s, 1H), 8.07 (d, 1H), 7.42-7.46 (m, 2H), 7.71-7.22 (m, 2H), 6.83 (d, J=7.2 Hz, 1H), 6.65-6.69 (m, 1H), 6.00 (d, J=8.0 Hz, 1H), 4.21 (s, 2H), 2.92 (bs, 2H), 2.15 (bs, 2H).

Example 68

Preparation of (±)-Trans-3-(5,6-dihydro-4H-pyrrolo[3,2,1-ij]quinolin-1-yl)-4-(3-methoxyphenyl)pyrrolidine-2,5-dione A mixture of 3-(5,6-dihydro-4H-pyrrolo[3,2,1-ij]quinolin-1-yl)-4-(3-methoxyphenyl)-1H-pyrrole-2,5-dione (0.73 g, 2.04 mmol), magnesium (0.89 g, 36.7 mmol) in anhydrous methanol was heated to reflux for 1.5 h. After cooling to room temperature, the light yellow solution was diluted with ethyl acetate (200 mL), washed with 1.0 M hydrochloric acid (2×50 mL), water (100 mL), dried over sodium sulfate and concentrated to provide a light brown solid. The residue was purified by column chromatography on silica gel eluting with 40-50% ethyl acetate in hexane to yield (±)-trans-3-(5,6-dihydro-4H-pyrrolo[3,2,1-ij]quinolin-1-yl)-4-(3-methoxyphenyl)pyrrolidine-2,5-dione as a light yellow solid. Mp 87-91° C.; $^1$H NMR (CDCl$_3$) 400 MHz δ: 8.73 (s, 1H), 7.25-7.30 (m, 1H), 7.14 (d, J=7.6 Hz, 1H), 6.93-7.01 (m, 3H), 6.77-6.86 (m, 3H), 4.36 (d, J=6.4 Hz, 1H), 4.24 (d, J=6.4 Hz, 1H), 4.18 (t J=5.5 Hz, 2H), 3.78 (s, 3H), 2.97 (t, J=5.6 Hz, 2H), 2.19-2.24 (m, 2H).

Example 69

Preparation of (±)-Trans-3-(5,6-dihydro-4H-pyrrolo[3,2,1-ij]quinolin-1-yl)-4-(3-hydroxyphenyl)pyrrolidine-2,5-dione To a solution of (±)-trans-3-(5,6-dihydro-4H-pyrrolo[3,2,1-ij]quinolin-1-yl)-4-(3-methoxyphenyl)pyrrolidine-2,5-dione in dichloromethane (10 mL) at −78° C. under an atmosphere of nitrogen was slowly added boron tribromide (1.0 M in dichloromethane) (5.2 mL). The resulting mixture was stirred at −78° C. for 30 minutes and at room temperature for 3 hours. The reaction mixture was cooled to −78° C. then quenched by the addition of methanol (5 mL). The mixture was allowed to warm to room temperature and maintained at room temperature for 30 minutes. The reaction mixture was diluted with dichloromethane (80 mL), washed with saturated aqueous sodium bicarbonate (15 mL), water (15 mL) and saturated sodium chloride (15 mL). The organic layer was dried over anhydrous sodium sulfate and concentrated to dryness. The residue was purified by flash chromatography on silica gel eluting with ethyl acetate:hexane:dichloromethane (5:5:1, v/v) to give (±)-trans-3-(5,6-dihydro-4H-pyrrolo[3,2,1-ij]quinolin-1-yl)-4-(3-hydroxyphenyl)pyrrolidine-2,5-dione as a brown solid (1.15 g, 63%); Mp 108-110° C. 1H NMR (CDCl3) 400 MHz δ: 8.69 (s, 1H), 7.18 (t, 1H, J=8.0 Hz), 7.12 (d, 1H, J=8.0 Hz), 6.99 (d, 1H, J=6.8 Hz), 6.97 (d, 1H, J=2.0 Hz), 6.93 (d, 1H, J=6.4 Hz), 6.76 (m, 1H), 6.69 (d, 1H, J=1.6 Hz), 5.67 (brs, 1H), 4.32 (d, 1H, J=6.0 Hz), 4.20 (d, 1H, J=6.0 Hz), 4.07 (t, 2H, J=5.6 Hz), 2.96 (t, 2H, J=6.0 Hz), 2.19 (m, 2H), LC/MS: 347.3 [M+H].

Example 70

Preparation of (+_)-Trans-3-(5,6-dihydro-4H-pyrrolo[3,2,1-ij]quinolin-1-yl)-4-(4-fluorophenyl)pyrrolidine-2,5-dione 3-(5,6-dihydro-4H-pyrrolo[3,2,1-ij]quinolin-1-yl)-4-(4-fluorophenyl)-1H-pyrrole-2,5-dione prepared according to Example 67, was reduced by employing the method of Example 68 to yield (±)-trans-3-(5,6-dihydro-4H-pyrrolo[3,2,1-ij]quinolin-1-yl)-4-(4-fluorophenyl)pyrrolidine-2,5-dione 1-ij]quinolin-1-yl)-4-(4-fluorophenyl)-1H-pyrrole-2,5-dione. Mp 208-210° C.; $^1$H NMR (DMSO-$d_6$) 400 MHz δ: 11.52 (s, 1H), 7.40-7.43 (m, 2H), 7.32 (m, 1H), 7.13-7.17 (m, 3H), 6.82-6.89 (m, 2H), 4.53 (m, 1H), 4.36 (m, 1H), 4.09 (t, J=5.2 Hz, 2H), 2.89 (t, J=6.0 Hz, 2H), 2.09-2.11 (m, 2H).

Example 71

Preparation of (±)-Trans-3-[4-(benzyloxy)phenyl]-4-(5,6-dihydro-4H-pyrrolo[3,2,1-ij]quinolin-1-yl)pyrrolidine-2,5-dione 3-[4-(benzyloxy)phenyl]-4-(5,6-dihydro-4H-pyrrolo[3,2,1-ij]quinolin-1-yl)-1H-pyrrole-2,5-dione prepared according to Example 66, was reduced by employing the method of Example 68 to yield (±)-trans 3-[4-(benzyloxy)phenyl]-4-(5,6-dihydro-4H-pyrrolo[3,2,1-ij]quinolin-1-yl)pyrrolidine-2,5-dione. Mp 91-93° C.; $^1$H NMR (DMSO-$d_6$) 400 MHz δ: 11.47 (s, 1H), 7.25-7.43 (m, 8H), 7.15 (d, J=7.6 Hz, 2H), 6.82-6.96 (m, 4H), 5.07 (s, 2H), 4.45 (d, J=7.6 Hz, 1H), 4.24 (d, J=7.6 Hz, 1H), 4.07-4.10 (m, 2H), 2.87-2.90 (m, 2H), 2.09-2.10 (m, 2H).

Example 72

Preparation of (±)-Trans-3-(5,6-dihydro-4H-pyrrolo[3,2,1-ij]quinolin-1-yl)-4-(4-hydroxyphenyl)pyrrolidine-2,5-dione A mixture of (±)-trans-3-[4-(benzyloxy)phenyl]-4-(5,6-dihydro-4H-pyrrolo[3,2,1-ij]quinolin-1-yl)pyrrolidine-2,5-dione (0.2 g) and Pd/C (10% w/w, 0.076 g) was stirred under 1 atmosphere of hydrogen gas overnight. The catalyst was filtered off through a pad of celite and concentrated. The residue was purified by column chromatography on silica gel eluting with 30-40% ethyl acetate in hexane to provide (±)-trans-3-(5,6-dihydro-4H-pyrrolo[3,2,1-ij]quinolin-1-yl)-4-(4-hydroxyphenyl)pyrrolidine-2,5-dione 0.07 g as a light yellow solid. Mp 105-107° C.; $^1$H NMR (acetone-$d_6$) 400 MHz δ: 10.27 (s, 1H), 8.34 (s, 1H), 7.17-7.21 (m, 4H), 6.80-6.91 (m, 4H), 4.39 (d, J=7.0 Hz, 1H), 4.22 (d, J=7.0 Hz, 1H), 4.13 (d, J=5.6 Hz, 2H), 2.92 (d, J=5.2 Hz, 2H), 2.15-2.19 (m, 2H).

Example 73

Preparation of 7-[4-(1H-indol-3-yl)-2,5-dioxo-2,5-dihydro-1H-pyrrol-3-yl]-3,4-dihydro-1H-[1,4]diazepino[6,7,1-hi]indole-2-carboxylic acid benzyl ester Step 1

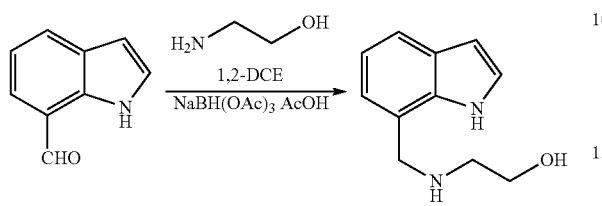

To a solution of 7-formyl indole (2.4 g, 16.6 mmol) in 1,2-dichloroethane (60 mL) was added aminoethanol (1.2 mL, 19.8 mmol) followed by glacial acetic acid (2.0 mL) and sodium triacetoxyborohydride (3.5 g, 16.6 mmol). The reaction mixture was allowed to stir at room temperature for 16 hours. The reaction mixture was quenched by addition of water (10 mL) and 1.0 M sodium hydroxide (10 mL). The organic layer was then separated and the aqueous layer extracted with 1,2-dichloroethane (40 mL). The combined organic extracts were washed with saturated sodium bicarbonate (2×30 mL), water (2×50 mL), dried over anhydrous sodium sulfate and evaporated to dryness. 2-[(1H-indol-7-ylmethyl)-amino]-ethanol (4.4 g) was obtained as an oil LCMS (M+H)=189.

Step 2

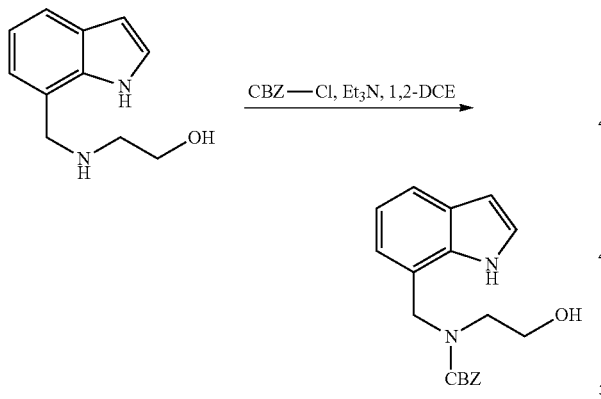

To a solution of 2-[(1H-indol-7-ylmethyl)-amino]-ethanol (4.4 g) in 1,2-dichloroethane (40 mL) was added triethylamine (4.85 mL, 34.6 mmol) followed by benzyl chloroformate (3.57 mL, 25.34 mmol). The mixture was allowed to stir at room temperature for 2 hours. The mixture was quenched by addition of water (20 mL), and 1.0 M sodium hydroxide (10 mL). The organic layer was separated and the aqueous layer extracted with 1,2-dichloroethane (20 mL). The combined organic extracts were washed with 1.0 M hydrochloric acid (20 mL), water (20 mL), dried over anhydrous sodium sulfate and evaporated to dryness. The residue was purified by silica gel chromatography, eluting with 20% ethyl acetate in hexanes to 40% ethyl acetate in hexanes to afford (2-hydroxy-ethyl)-(1H-indol-7-ylmethyl)-carbamic acid benzyl ester (2.79 g, 52% combined yield for two steps) as a colorless oil. $^1$H NMR (CDCl$_3$) 400 MHz δ: 9.97 (br s, 1H), 7.75-6.9 (m, 8H), 6.54 (br s, 1H), 5.21 (s, 2H), 4.9-4.6 (m, 3H), 3.85-3.57 (m, 2H), 3.55-3.23 (m, 3H); LCMS M+H=325.

Step 3

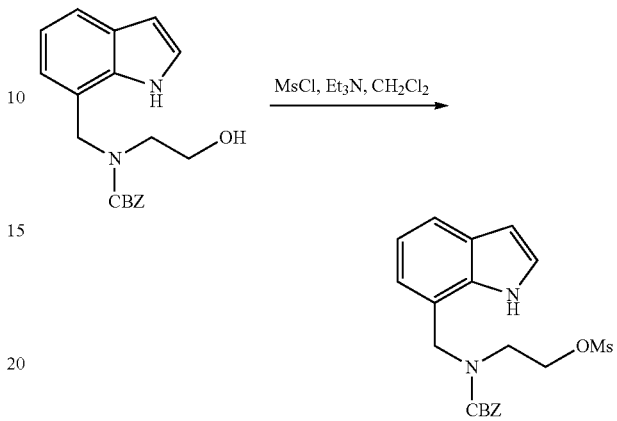

To a solution of (2-hydroxy-ethyl)-(1H-indol-7-ylmethyl)-carbamic acid benzyl ester (2.79 g, 8.61 mmol) in dichloromethane (50 mL) was added triethylamine (1.56 mL, 11.2 mmol). The mixture was cooled to 0° C. and methanesulfonyl chloride (0.74 mL, 9.47 mmol) added in a dropwise manner. The mixture was warmed to room temperature and allowed to stir for 2 hours. The mixture was then quenched with water (30 mL) and 1.0 M sodium hydroxide (10 mL). The organic layer was separated and the aqueous layer extracted with dichloromethane (20 mL). The combined extracts were washed with 1.0 M hydrochloric acid (20 mL), water (30 mL), dried over anhydrous sodium sulfate and evaporated to dryness. Methanesulfonic acid 2-[benzyloxycarbonyl-(1H-indol-7-ylmethyl)-amino]-ethyl ester (3.46 g) was obtained as an oil Step 4

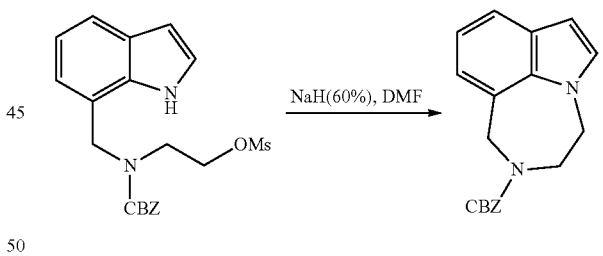

To a solution of methanesulfonic acid 2-[benzyloxycarbonyl-(1H-indol-7-ylmethyl)-amino]-ethyl ester (3.46 g, 8.61 mmol) in dimethylformamide (20 mL), which has been cooled to 0° C. was added sodium hydride (60%) in mineral oil. The reaction mixture was allowed to stir at 0° C. for 1 hour and then quenched by the addition of water (40 mL). The aqueous layer was extracted with ethyl acetate (4×20 mL). The combined organic extracts were washed with water (3×30 mL), dried over anhydrous sodium sulfate and evaporated to dryness. The residue was purified by silica gel chromatography, eluting with dichloromethane to afford 3,4-dihydro-1H-[1,4]diazepino[6,7,1-hi]indole-2-carboxylic acid benzyl ester (1.95 g, 74% combined yield for two steps) as a colorless oil. $^1$H NMR (CDCl$_3$) 400 MHz δ: 7.6-7.45 (m, 1H), 7.4-7.2 (m, 5H), 7.17-6.9 (m, 3H), 6.6-6.48 (m, 1H), 5.2-5.05 (m, 2H), 5.0-4.82 (m, 2H), 4.4-4.2 (m, 2H), 4.1-3.95 (m, 2H); LCMS (M+H)=307.

Step 5

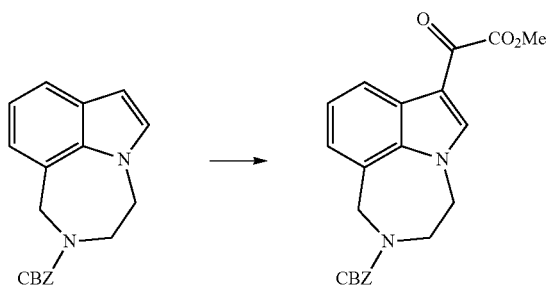

To a solution of 3,4-dihydro-1H-[1,4]diazepino[6,7,1-hi]indole-2-carboxylic acid benzyl ester (557 mg, 1.8 mmol), in anhydrous tetrahydrofuran (10 ml) at 0° C., was added oxalyl chloride (238 µl, 2.7 mmol) followed by a further portion of oxalyl chloride (340 µl, 3.85 mmol). The mixture was stirred at 0° C. until all the starting material has been consumed before being cooled to −78° C. Sodium methoxide in methanol (0.5M) (10 ml) was then added slowly and the mixture allowed to warm to room temperature. After 1 hour at room temperature the mixture was then diluted with ethyl acetate (200 ml) and washed with water (300 ml). The organic layer was dried over anhydrous sodium sulfate and evaporated to dryness. The residue was purified by silica gel chromatography, eluting with a ethyl acetate/hexanes (1:1) to afford 7-methoxyoxalyl-3,4-dihydro-1H-[1,4]diazepino[6,7,1-hi]indole-2-carboxylic acid benzyl ester as a pale yellow solid (481 mg, 67%). $^1$H NMR (CDCl$_3$) 400 MHz δ: 8.26-8.36 (m, 2H), 7.22-7.37 (m, 6H), 7.10 (dd, 1H, J=32.8 and 7.2 Hz), 5.11 (d, 2H, J=8.0 Hz), 4.94 (d, 2H, J=22.4 Hz), 4.41-4.48 (m, 2H), 4.01-4.05 (m, 2H), 3.93 (m, 3H).

Step 6

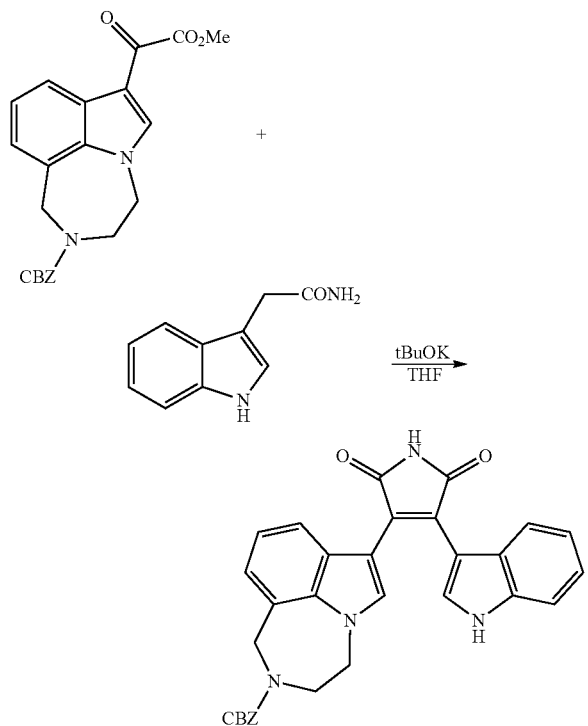

To a solution of 7-methoxyoxalyl-3,4-dihydro-1H-[1,4]diazepino[6,7,1-hi]indole-2-carboxylic acid benzyl ester (481 mg, 1.22 mmol) and indole-3-acetamide (234 mg, 1.34 mmol) in anhydrous tetrahydrofuran (14 ml) at 0° C. was added potassium t-butoxide (412 mg, 3.67 mmol). The mixture was stirred at 0° C. for 2 hours. Concentrated hydrochloric acid (5 ml) was then added and the mixture stirred for 2 hours at room temperature. The mixture was then diluted with ethyl acetate (300 ml), washed with water (500 ml), and the organic layer dried over anhydrous sodium sulfate. The residue was purified by silica gel chromatography, eluting with a ethyl acetate/hexanes (1:1) to afford 7-[4-(1H-indol-3-yl)-2,5-dioxo-2,5-dihydro-1H-pyrrol-3-yl]-3,4-dihydro-1H-[1,4]diazepino[6,7,1-hi]indole-2-carboxylic acid benzyl ester as a bright orange/red solid (1.2 g, 80%). $^1$H NMR (DMSO-d$_6$) 400 MHz δ: 11.66 (d, 1H, J=2.4 Hz), 10.94 (s, 1H), 7.69-7.75 (m, 2H), 7.19-7.38 (m, 6H), 6.98 (t, 1H, J=7.2 Hz), 6.73-6.89 (m, 3H), 6.60-6.66 (m, 2H), 4.90-5.08 (m, 2H), 4.50 (m, 2H), 3.95 (m, 2H).

Example 74

Preparation of (±)-Trans-7-[4-(1H-indol-3-yl)-2,5-dioxo-pyrrolidin-3-yl]-3,4-dihydro-1H-[1,4]diazepino[6,7,1-hi]indole-2-carboxylic acid benzyl ester

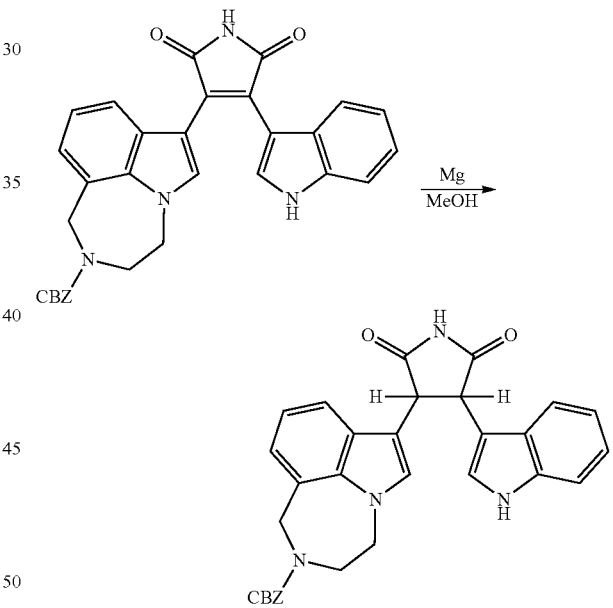

Magnesium turnings (195 mg, 8.0 mmol) were added to a solution of 7-[4-(1H-indol-3-yl)-2,5-dioxo-2,5-dihydro-1H-pyrrol-3-yl]-3,4-dihydro-1H-[1,4]diazepino[6,7,1-hi]indole-2-carboxylic acid benzyl ester (230 mg, 0.44 mmol) in anhydrous methanol (20 ml) and heated to reflux under an atmosphere of nitrogen for 1.5 hours. After cooling to room temperature the mixture was poured into ethyl acetate (200 ml) and washed with 1 M hydrochloric acid (100 ml). The organic layer was dried over anhydrous sodium sulfate and evaporated to dryness. The residue was then purified by silica gel chromatography using 50-60% ethyl acetate in hexanes to yield (±)-trans-7-[4-(1H-indol-3-yl)-2,5-dioxo-pyrrolidin-3-yl]-3,4-dihydro-1H-[1,4]diazepino[6,7,1-hi]indole-2-carboxylic acid benzyl ester as an off white solid (205 mg). $^1$H NMR (DMSO-d$_6$) 400 MHz δ: 11.56 (s, 1H), 11.03

(d, 1H, J=2 Hz), 7.21-7.43 (m, 10H), 7.09 (t, 1H, J=7.2 Hz), 6.92-7.00 (m, 2H), 6.82-6.89 (m, 3H), 5.04 (s, 2H), 4.87 (d, 2H, J=7.6 Hz), 4.54 (dd, 2H, J=7.6 and 28.8 Hz), 4.30 (m, 2H), 3.92 (m, 2H).

Example 75

Preparation of (±)-Trans-3-(1H-indol-3-yl)-4-(1,2,3,4-tetrahydro-[1,4]diazepino[6,7,1-hi]indol-7-yl)-pyrrolidine-2,5-dione

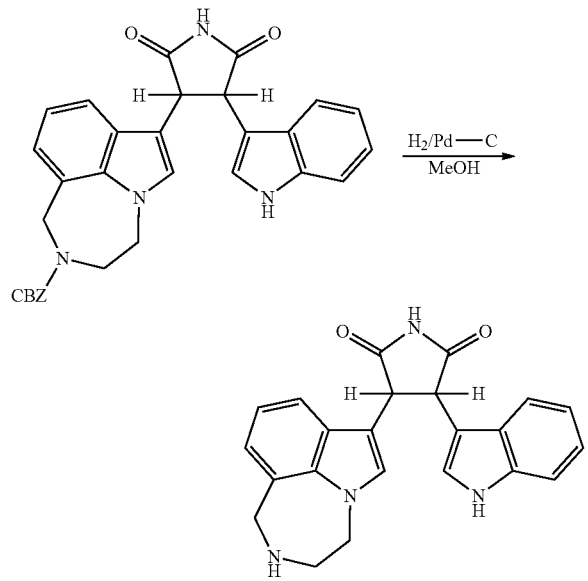

(±)-Trans-7-[4-(1H-indol-3-yl)-2,5-dioxo-pyrrolidin-3-yl]-3,4-dihydro-1H-[1,4]diazepino[6,7,1-hi]indole-2-carboxylic acid benzyl ester (161 mg, 0.31 mmol) and 10% palladium on carbon (100 mg) in anhydrous methanol (15 ml) were stirred under 1 atmosphere of hydrogen for 16 hours. The catalyst was then filtered through a bed of Celite and the filtrate evaporated to dryness to yield (±)-trans-3-(1H-indol-3-yl)-4-(1,2,3,4-tetrahydro-[1,4]diazepino[6,7,1-hi]indol-7-yl)-pyrrolidine-2,5-dione as an off white solid (95 mg). $^1$H NMR (DMSO-$d_6$) 400 MHz δ: 11.04 (d, 1H, J=1.6 Hz), 7.35-7.42 (m, 4H), 7.24 (dd, 1H, J=2.8 and 5.6 Hz), 7.09 (t, 1H, J=7.2 Hz), 6.89-6.98 (m, 3H), 4.52 (dd, 2H, J=7.2 and 24.8 Hz), 4.11 (s, 2H), 4.07-4.10 (m, 2H), 3.14-3.17 (m, 2H).

Example 76

Cell viability was determined by measuring the activity of dehydrogenase enzymes in metabolically active cells using a tetrazolium compound, MTS. The assay was performed as described in Promega Technical Bulletin No. 169 (CellTiter 96 Aqueous Non-Radioactive Cell Proliferation Assay). Thirteen human cancer cell lines were assayed (see, e.g., Table 1). Cells were maintained at 37° C., 5% $CO_2$. Adherent cells were maintained DMEM media (4.5 g/L glucose) supplemented with 15% heat-inactivated FBS, 10 mM L-glutamine, and 10 mM Hepes pH 7.5. Suspension cells were maintained in RPMI 1640 media, supplemented with 10% heat-inactivated FBS and 10 mM Hepes pH 7.5. Briefly, cells were seeded in 96-well plates as set forth in Table 1 and incubated for 16-24 hours. Candidate compounds were serially diluted in DMSO, further diluted in cell culture media, and then added to cells (final DMSO concentration of 0.33%). Cells were incubated in the presence of candidate compound for 72 hours. MTS stock solution (MTS 2 gm/L, PMS 46.6 mg/ml in PBS) was added to the cells (final concentration MTS 2 gm/L and PMS 7.67 mg/L) and incubated for 4 hours. SDS was added to a final concentration of 1.4% and absorbance at 490 nM was measured within two hours using a platereader. The $IC_{50}$ was defined as the concentration of compound that results in a 50% reduction in the number of viable cells as compared to control wells treated with DMSO only (0.33%) and was calculated using non-linear regression analyswas. $IC_{50}$ values were given in Table 2 for the compounds listed.

TABLE 1

| Cell Line | Cancer Type | Cells/well |
| --- | --- | --- |
| NCI-H69 | small cell lung | 8500 |
| NCI-H446 | small cell lung | 10000 |
| NCI-H82 | small cell lung | 8500 |
| HCT-116 | small cell lung | 1200 |
| sHT29 | colon | 2500 |
| MDA-MB-231 | breast | 3500 |
| A549 | lung | 400 |
| DU-145 | prostate | 1000 |
| K562 | chronic myelogenous leukemia | 1200 |
| MCF7 | breast | 8000 |
| PC-3 | prostate | 3000 |
| SK-MEL-28 | melanoma | 1000 |
| SKOV-3 | ovarian | 1800 |

TABLE 2

| Compound | Example Number | A549 | DU-145 | NCI-H69 | HCT-116 | HT29 | K562 | MCF7 |
| --- | --- | --- | --- | --- | --- | --- | --- | --- |
| (±)-Cis-3-(5,6-dihydro-4H-pyrrolo [3,2,1-ij] quinolin-1-yl)-4(1H-indol-3-yl) pyrrolidine-2,5-dione | 2 | | | | | 2.89 | | |
| (±)-Trans-3-(5,6-dihydro-4H-pyrrolo [3,2,1-ij] quinolin-1-yl)-4(1H-indol-3-yl) pyrrolidine-2,5-dione | 2, 3 | 10.7 | 9.61 | | 1.82 | 4.55 | 0.424 | >100 |
| 3(R),4(S)-3-(5,6-Dihydro-4H-pyrrolo [3,2,1-ij] quinolin-1-yl)-4(1H-indol-3-yl) pyrrolidine-2,5-dione (faster eluting peak in supercritical chromatography) | 4 | | | 1.85 | | 5.5 | | |

TABLE 2-continued

| Compound | Ex. | C1 | C2 | C3 | C4 | C5 | C6 | C7 |
|---|---|---|---|---|---|---|---|---|
| 3(S),4(R)-3-(5,6-Dihydro-4H-pyrrolo [3,2,1-ij] quinolin-1-yl)-4(1H-indol-3-yl) pyrrolidine-2,5-dione (slower eluting peak in supercritical chromatography) | 4 | | | 2.07 | 9.71 | | | |
| (−)-Trans-3-(5,6-dihydro-4H-pyrrolo [3,2,1-ij] quinolin-1-yl)-4(1H-indol-3-yl) pyrrolidine-2,5-dione (faster eluting peak in supercritical chromatography) | 5 | 5.8 | 4 | 1.04 | 0.812 | 1.95 | 0.294 | >100 |
| (+)-Trans-3-(5,6-dihydro-4H-pyrrolo [3,2,1-ij] quinolin-1-yl)-4(1H-indol-3-yl) pyrrolidine-2,5-dione (slower eluting peak in supercritical chromatography) | 5 | 27.9 | | 10.5 | 14.4 | 30.13 | 4.52 | >100 |
| 3-(5,6-Dihydro-4H-pyrrolo [3,2,1-ij] quinolin-1-yl)-4(2-trifluoromethyl-phenyl)-pyrrole-2,5-dione | 6 | | | | | 62.7 | | |
| 3-(5,6-Dihydro-4H-pyrrolo [3,2,1-ij] quinolin-1-yl)-4-thiophen-2-yl-pyrrole-2,5-dione | 7 | | | | | >100 | | |
| 3-(5,6-Dihydro-4H-pyrrolo [3,2,1-ij] quinolin-1-yl)-4-pyridin-2-yl-pyrrole-2,5-dione | 9 | | | | | >100 | | |
| 3-(5,6-Dihydro-4H-pyrrolo [3,2,1-ij] quinolin-1-yl)-4(4-methoxy-phenyl)-pyrrole-2,5-dione | 10 | | | | | >100 | | |
| 3-Benzo[1,3]dioxol-5-yl-4-(5,6-dihydro-4H-pyrrolo [3,2,1-ij]quinolin-1-yl)-pyrrole-2,5-dione | 11 | | | | | >100 | | |
| 3-(5,6-Dihydro-4H-pyrrolo [3,2,1-ij] quinolin-1-yl)-4-phenyl-pyrrole-2,5-dione | 12 | | | | | 66.5 | | |
| 3-Benzo[b]thiophen-2-yl-4-(5,6-dihydro-4H-pyrrolo [3,2,1-ij] quinolin-1-yl)-pyrrole-2,5-dione | 13 | | | | | >100 | | |
| 3-(5,6-Dihydro-4H-pyrrolo [3,2,1-ij] quinolin-1-yl)-4-(3-phenoxy-phenyl)-pyrrole-2,5-dione | 14 | | | | | 71.6 | | |
| 3-(5,6-Dihydro-4H-pyrrolo [3,2,1-ij] quinolin-1-yl)-4-(3-chloro-phenyl)-pyrrole-2,5-dione | 15 | | | | | 75.8 | | |
| 3-(5,6-Dihydro-4H-pyrrolo [3,2,1-ij] quinolin-1-yl)-4-(2-chloro-phenyl)-pyrrole-2,5-dione | 16 | | | | | 40.9 | | |
| 3-(5,6-Dihydro-4H-pyrrolo [3,2,1-ij] quinolin-1-yl)-4-(2,5-dimethoxy-phenyl)-pyrrole-2,5-dione | 17 | | | | | >100 | | |
| 3-(5,6-Dihydro-4H-pyrrolo [3,2,1-ij] quinolin-1-yl)-4-(2-chloro-4-fluoro-phenyl)-pyrrole-2,5-dione | 18 | | | | | >100 | | |
| 3-(5,6-Dihydro-4H-pyrrolo [3,2,1-ij] quinolin-1-yl)-4-naphthalene-1-yl-pyrrole-2,5-dione | 19 | 41 | >100 | 26.2 | 46.8 | 14 | | >100 |
| 3-(5,6-Dihydro-4H-pyrrolo [3,2,1-ij] quinolin-1-yl)-4-(2,6-dichloro-phenyl)-pyrrole-2,5-dione | 20 | 38.8 | 31.1 | 4.96 | >100 | 2.47 | | >100 |
| 3-(5,6-Dihydro-4H-pyrrolo [3,2,1-ij] quinolin-1-yl)-4-(2-bromo-phenyl)-pyrrole-2,5-dione | 21 | 28.6 | 21.8 | 5.44 | 56.75 | 6.42 | | >100 |
| 3-(5,6-Dihydro-4H-pyrrolo [3,2,1-ij] quinolin-1-yl)-4-indol-1-yl-pyrrole-2,5-dione | 22 | | | | | >100 | | |
| 3-(5,6-Dihydro-4H-pyrrolo [3,2,1-ij] quinolin-1-yl)-4-pyridine-3-yl-pyrrole-2,5-dione | 23 | | | | | 76.8 | | |
| 3-(4-Benzoyloxy-phenyl)-4-(5,6-dihydro-4H-pyrrolo [3,2,1-ij] quinolin-1-yl)-pyrrole-2,5-dione | 29 | | | | | >100 | | |
| (±)-Trans-3-(5,6-dihydro-4H-pyrrolo [3,2,1-ij] quinolin-1yl)-4-(5-(1-naphthyl)-1H-indol-3-yl) pyrrolidine-2,5-dione | 37 | | | | | 37.4 | | |

TABLE 2-continued

| Compound | # | C1 | C2 | C3 | C4 | C5 | C6 |
|---|---|---|---|---|---|---|---|
| (±)-Trans-3-(5,6-dihydro-4H-pyrrolo [3,2,1-ij] quinolin-1yl)-4-(5-(4-methoxyphenyl)-1H-indol-3-yl) pyrrolidine-2,5-dione | 38 | | | | 10.6 | | |
| (±)-Trans-3-(5,6-dihydro-4H-pyrrolo [3,2,1-ij] quinolin-1yl)-4-(5-(3-methylphenyl)-1H-indol-3-yl) pyrrolidine-2,5-dione | 39 | | | | 10.5 | | |
| (±)-Trans-3-(5,6-dihydro-4H-pyrrolo [3,2,1-ij] quinolin-1yl)-4-(2-chloro-4-fluorophenyl) pyrrolidine-2,5-dione | 40 | | | | 10.5 | | |
| (±)-Trans-3-(5,6-dihydro-4H-pyrrolo [3,2,1-ij] quinolin-1yl)-4-(2,6-dichlorophenyl) pyrrolidine-2,5-dione | 41 | | | | 4.65 | | |
| (±)-Trans-3-(5,6-dihydro-4H-pyrrolo [3,2,1-ij] quinolin-1yl)-4-(4-bromophenyl) pyrrolidine-2,5-dione | 42 | | | | 44.1 | | |
| (±)-Trans-3-(5,6-dihydro-4H-pyrrolo [3,2,1-ij] quinolin-1yl)-4-(4-chlorophenyl) pyrrolidine-2,5-dione | 43 | | | | 48.7 | | |
| (±)-Trans-3-(5,6-dihydro-4H-pyrrolo [3,2,1-ij] quinolin-1yl)-4-(4-trifluoromethoxyphenyl) pyrrolidine-2,5-dione | 44 | | | | 12.5 | | |
| (±)-Trans-3-(5,6-dihydro-4H-pyrrolo [3,2,1-ij] quinolin-1yl)-4-(thiophen-3-yl) pyrrolidine-2,5-dione | 45 | | | | 27.6 | | |
| (±)-Trans-3-(5,6-dihydro-4H-pyrrolo [3,2,1-ij] quinolin-1yl)-4-(2-fluorophenyl) pyrrolidine-2,5-dione | 46 | | | | 4.76 | | |
| (±)-Trans-3-(5,6-dihydro-4H-pyrrolo [3,2,1-ij] quinolin-1yl)-4-(2-thiophen-2-yl) pyrrolidine-2,5-dione | 47 | | | 4.45 | 18.3 | | |
| (±)-Trans-3-(5,6-dihydro-4H-pyrrolo [3,2,1-ij] quinolin-1yl)-4-(2,4-dichlorophenyl) pyrrolidine-2,5-dione | 48 | | | | 8.39 | | |
| (±)-Trans-3-(5,6-dihydro-4H-pyrrolo [3,2,1-ij] quinolin-1yl)-4-phenyl-pyrrolidine-2,5-dione | 49 | | | | 14.6 | | |
| (±)-Trans-3-(5,6-dihydro-4H-pyrrolo [3,2,1-ij] quinolin-1yl)-4-(2-chlorophenyl)-pyrrolidine-2,5-dione | 50 | | | 5.41 | 8.51 | | |
| (±)-Trans-3-(5,6-dihydro-4H-pyrrolo [3,2,1-ij] quinolin-1yl)-4-(N-methylindol-3-yl) pyrrolidine-2,5-dione | 51 | | | 37.7 | 66.75 | | |
| (±)-Cis-3-(5,6-dihydro-4H-pyrrolo [3,2,1-ij] quinolin-1yl)-4-(2,5-dimethoxyphenyl)-pyrrolidine-2,5-dione | 53 | >100 | >100 | >100 | >100 | 36.3 | >100 |
| (±)-Cis-3-(5,6-dihydro-4H-pyrrolo [3,2,1-ij] quinolin-1yl)-4-(2-chloro-4-fluoro-phenyl)-pyrrolidine-2,5-dione | 54 | 22.1 | 21.1 | 7.63 | 8.78 | 3.37 | >100 |
| (±)-Cis-3-(5,6-dihydro-4H-pyrrolo [3,2,1-ij] quinolin-1yl)-4-(3-chlorophenyl)-pyrrolidine-2,5-dione | 55 | 13.1 | 35.7 | 12.1 | 13.1 | 3.47 | >100 |
| Phosphoric acid dibenzyl ester trans-3-(5,6-dihydro-4H-pyrrolo[3,2,1-ij]quinolin-1-yl)-4-(1H-indol-3-yl)-2,5-dioxo-pyrrolidin-1-ylmethyl ester | 56 | | | | 22.6 | | |
| (±)-Phosphoric acid mono-[trans-3-(5,6-dihydro-4H-pyrrolo[3,2,1-ij]quinolin-1-yl)-4-(1H-indol-3-yl)-2,5-dioxo-pyrrolidin-1-ylmethyl] ester | 56 | | | | 4.45 | | |

TABLE 2-continued

| Compound | Example Number | NCI-H82 |
|---|---|---|
| (±)-trans-2-Amino-propionic acid-3-(5,6-dihydro-4H-pyrrolo[3,2,1-ij]quinolin-1-yl)-4-(1H-indol-3-yl)-2,5-dioxo-pyrrolidin-1-yl methyl ester | 57 | 2.9 |
| (±)-trans-Amino-acetic acid-3-(5,6-dihydro-4H-pyrrolo[3,2,1-ij]quinolin-1-yl)-4-(1H-indol-3-yl)-2,5-dioxo-pyrrolidin-1-yl methyl ester | 58 | 2.77 |
| (±)-trans-dimethylamino-acetic acid-3-(5,6-dihydro-4H-pyrrolo[3,2,1-ij]quinolin-1-yl)-4-(1H-indol-3-yl)-2,5-dioxo-pyrrolidin-1-ylmethyl ester | 59 | 3.74 |
| (±)-trans-Isonicotinic acid-3-(5,6-dihydro-4H-pyrrolo[3,2,1-ij]quinolin-1-yl)-4-(1H-indol-3-yl)-2,5-dioxo-pyrrolidin-1-ylmethyl ester | 60 | 3.59 |

| Compound | Example Number | MDA-MB-231 | NCI-H446 | NCI-H82 | PC-3 | SK-MEL-28 | SKOV-3 |
|---|---|---|---|---|---|---|---|
| (±)-cis-3-(5,6-dihydro-4H-pyrrolo[3,2,1-ij] quinolin-1-yl)-4(1-methylindol-3-yl)-1-methyl pyrrolidine-2,5-dione | 61 | 78.9 | >100 | 96.2 | >100 | 18.7 | >100 |
| 3-(5,6-Dihydro-4H-pyrrolo[3,2,1-ij]quinolin-1-yl)-4-(3-methoxyphenyl)-1H-pyrrole-2,5-dione | 65 | | | 35 | | | |
| 3-[4-(Benzyloxy)phenyl]-4-(5,6-dihydro-4H-pyrrolo[3,2,1-ij]quinolin-1-yl)-1H-pyrrole-2,5-dione | 66 | | | >100 | | | |
| 3-(5,6-Dihydro-4H-pyrrolo[3,2,1-ij]quinolin-1-yl)-4-(4-fluorophenyl)-1H-pyrrole-2,5-dione | 67 | | | 53.1 | | | |
| (±)-Trans-3-(5,6-dihydro-4H-pyrrolo[3,2,1-ij]quinolin-1-yl)-4-(3-methoxyphenyl)pyrrolidine-2,5-dione | 68 | | | 3.06 | | | |
| (±)-Trans-3-(5,6-dihydro-4H-pyrrolo[3,2,1-ij]quinolin-1-yl)-4-(3-hydroxyphenyl)pyrrolidine-2,5-dione | 69 | | | 55.4 | | | |
| (±)-Trans-3-(5,6-dihydro-4H-pyrrolo[3,2,1-ij]quinolin-1-yl)-4-(4-fluorophenyl)pyrrolidine-2,5-dione | 70 | | | 26.2 | | | |
| (±)-Trans-3-[4-(benzyloxy)phenyl]-4-(5,6-dihydro-4H-pyrrolo[3,2,1-ij]quinolin-1-yl)pyrrolidine-2,5-dione | 71 | | | 48.7 | | | |
| (±)-Trans-3-(5,6-dihydro-4H-pyrrolo[3,2,1-ij]quinolin-1-yl)-4-(4-hydroxyphenyl)pyrrolidine-2,5-dione | 72 | | | >100 | | | |
| 7-[4-(1H-indol-3-yl)-2,5-dioxo-2,5-dihydro-1H-pyrrol-3-yl]-3,4-dihydro-1H-[1,4]diazepino[6,7,1-hi]indole-2-carboxylic acid benzyl ester | 73 | | | >100 | | | |
| (±)-Trans-7-[4-(1H-indol-3-yl)-2,5-dioxo-pyrrolidin-3-yl]-3,4-dihydro-1H-[1,4]diazepino[6,7,1-hi]indole-2-carboxylic acid benzyl ester | 74 | | | 90.7 | | | |
| (±)-Trans-3-(1H-indol-3-yl)-4-(1,2,3,4-tetrahydro-[1,4]diazepino[6,7,1-hi]indol-7-yl)-pyrrolidine-2,5-dione | 75 | | | >100 | | | |
| (±)-Cis-3-(5,6-dihydro-4H-pyrrolo[3,2,1-ij] quinolin-1-yl)-4(1H-indol-3-yl) pyrrolidine-2,5-dione | 2 | 4.04 | | | | | |

TABLE 2-continued

| | | | | | | | |
|---|---|---|---|---|---|---|---|
| (±)-Trans-3-(5,6-dihydro-4H-pyrrolo [3,2,1-ij] quinolin-1-yl)-4(1H-indol-3-yl) pyrrolidine-2,5-dione | 2, 3 | 3.34 | | | 4.95 | 13 | 0.939 |
| 3(R),4(S)-3-(5,6-Dihydro-4H-pyrrolo [3,2,1-ij] quinolin-1-yl)-4(1H-indol-3-yl) pyrrolidine-2,5-dione (faster eluting peak in supercritical chromatography) | 4 | 3.69 | 1.27 | 1.49 | | | |
| 3(S),4(R)-3-(5,6-Dihydro-4H-pyrrolo [3,2,1-ij] quinolin-1-yl)-4(1H-indol-3-yl) pyrrolidine-2,5-dione (slower eluting peak in supercritical chromatography) | 4 | 5.17 | 1.42 | 1.77 | | | |
| (−)-Trans-3-(5,6-dihydro-4H-pyrrolo [3,2,1-ij] quinolin-1-yl)-4(1H-indol-3-yl) pyrrolidine-2,5-dione (faster eluting peak in supercritical chromatography) | 5 | 2.19 | 0.581 | 0.828 | 1.28 | 8.68 | 0.444 |
| (+)-Trans-3-(5,6-dihydro-4H-pyrrolo [3,2,1-ij] quinolin-1-yl)-4(1H-indol-3-yl) pyrrolidine-2,5-dione (slower eluting peak in supercritical chromatography) | 5 | 26.83 | 8.55 | 9.83 | 18.7 | 25.5 | 4.45 |
| 3-(5,6-Dihydro-4H-pyrrolo [3,2,1-ij] quinolin-1-yl)-4(2-trifluoromethyl-phenyl)-pyrrole-2,5-dione | 6 | 61.2 | | | | | |
| 3-(5,6-Dihydro-4H-pyrrolo [3,2,1-ij] quinolin-1-yl)-4-thiophen-2-yl-pyrrole-2,5-dione | 7 | >100 | | | | | |
| 3-(5,6-Dihydro-4H-pyrrolo [3,2,1-ij] quinolin-1-yl)-4-pyridin-2-yl-pyrrole-2,5-dione | 9 | >100 | | | | | |
| 3-(5,6-Dihydro-4H-pyrrolo [3,2,1-ij] quinolin-1-yl)-4(4-methoxy-phenyl)-pyrrole-2,5-dione | 10 | >100 | | | | | |
| 3-Benzo[1,3]dioxol-5-yl-4-(5,6-dihydro-4H-pyrrolo [3,2,1-ij]quinolin-1-yl)-pyrrole-2,5-dione | 11 | >100 | | | | | |
| 3-(5,6-Dihydro-4H-pyrrolo [3,2,1-ij] quinolin-1-yl)-4-phenyl-pyrrole-2,5-dione | 12 | 81.6 | | | | | |
| 3-Benzo[b]thiophen-2-yl-4-(5,6-dihydro-4H-pyrrolo [3,2,1-ij] quinolin-1-yl)-pyrrole-2,5-dione | 13 | 78.8 | | | | | |
| 3-(5,6-Dihydro-4H-pyrrolo [3,2,1-ij] quinolin-1-yl)-4-(3-phenoxy-phenyl)-pyrrole-2,5-dione | 14 | 98.2 | | | | | |
| 3-(5,6-Dihydro-4H-pyrrolo [3,2,1-ij] quinolin-1-yl)-4-(3-chloro-phenyl)-pyrrole-2,5-dione | 15 | 43.6 | | | | | |
| 3-(5,6-Dihydro-4H-pyrrolo [3,2,1-ij] quinolin-1-yl)-4-(2-chloro-phenyl)-pyrrole-2,5-dione | 16 | 21.5 | | | | | |
| 3-(5,6-Dihydro-4H-pyrrolo [3,2,1-ij] quinolin-1-yl)-4-(2,5-dimethoxy-phenyl)-pyrrole-2,5-dione | 17 | >100 | | | | | |
| 3-(5,6-Dihydro-4H-pyrrolo [3,2,1-ij] quinolin-1-yl)-4-(2-chloro-4-fluoro-phenyl)-pyrrole-2,5-dione | 18 | >100 | | | | | |
| 3-(5,6-Dihydro-4H-pyrrolo [3,2,1-ij] quinolin-1-yl)-4-naphthalene-1-yl-pyrrole-2,5-dione | 19 | 70.5 | | | 96.2 | 39.6 | 36.2 |
| 3-(5,6-Dihydro-4H-pyrrolo [3,2,1-ij] quinolin-1-yl)-4-(2,6-dichloro-phenyl)-pyrrole-2,5-dione | 20 | 50.3 | | | 82.7 | 74 | 23.8 |
| 3-(5,6-Dihydro-4H-pyrrolo [3,2,1-ij] quinolin-1-yl)-4-(2-bromo-phenyl)-pyrrole-2,5-dione | 21 | 30 | | | 22.2 | >100 | 30.2 |
| 3-(5,6-Dihydro-4H-pyrrolo [3,2,1-ij] quinolin-1-yl)-4-indol-1-yl-pyrrole-2,5-dione | 22 | 59.4 | | | | | |

TABLE 2-continued

| | | | | | | |
|---|---|---|---|---|---|---|
| 3-(5,6-Dihydro-4H-pyrrolo [3,2,1-ij] quinolin-1-yl)-4-pyridine-3-yl-pyrrole-2,5-dione | 23 | 28.7 | | | | |
| 3-(4-Benzoyloxy-phenyl)-4-(5,6-dihydro-4H-pyrrolo [3,2,1-ij] quinolin-1-yl)-pyrrole-2,5-dione | 29 | >100 | | | | |
| (±)-Trans-3-(5,6-dihydro-4H-pyrrolo [3,2,1-ij] quinolin-1yl)-4-(5-(1-naphthyl)-1H-indol-3-yl) pyrrolidine-2,5-dione | 37 | 43.4 | | | | |
| (±)-Trans-3-(5,6-dihydro-4H-pyrrolo [3,2,1-ij] quinolin-1yl)-4-(5-(4-methoxyphenyl)-1H-indol-3-yl) pyrrolidine-2,5-dione | 38 | 13.1 | | | | |
| (±)-Trans-3-(5,6-dihydro-4H-pyrrolo [3,2,1-ij] quinolin-1yl)-4-(5-(3-methylphenyl)-1H-indol-3-yl) pyrrolidine-2,5-dione | 39 | 11.2 | | | | |
| (±)-Trans-3-(5,6-dihydro-4H-pyrrolo [3,2,1-ij] quinolin-1yl)-4-(2-chloro-4-fluorophenyl) pyrrolidine-2,5-dione | 40 | 10.7 | | | | |
| (±)-Trans-3-(5,6-dihydro-4H-pyrrolo [3,2,1-ij] quinolin-1yl)-4-(2,6-dichlorophenyl) pyrrolidine-2,5-dione | 41 | 7.63 | | | | |
| (±)-Trans-3-(5,6-dihydro-4H-pyrrolo [3,2,1-ij] quinolin-1yl)-4-(4-bromophenyl) pyrrolidine-2,5-dione | 42 | 49.6 | | | | |
| (±)-Trans-3-(5,6-dihydro-4H-pyrrolo [3,2,1-ij] quinolin-1yl)-4-(4-chlorophenyl) pyrrolidine-2,5-dione | 43 | 54.5 | | | | |
| (±)-Trans-3-(5,6-dihydro-4H-pyrrolo [3,2,1-ij] quinolin-1yl)-4-(4-trifluoromethoxyphenyl) pyrrolidine-2,5-dione | 44 | 14.1 | | | | |
| (±)-Trans-3-(5,6-dihydro-4H-pyrrolo [3,2,1-ij] quinolin-1yl)-4-(thiophen-3-yl) pyrrolidine-2,5-dione | 45 | 42.7 | | | | |
| (±)-Trans-3-(5,6-dihydro-4H-pyrrolo [3,2,1-ij] quinolin-1yl)-4-(2-fluorophenyl) pyrrolidine-2,5-dione | 46 | >100 | | | | |
| (±)-Trans-3-(5,6-dihydro-4H-pyrrolo [3,2,1-ij] quinolin-1yl)-4-(2-thiophen-2-yl) pyrrolidine-2,5-dione | 47 | 19.87 | 9.82 | 7.25 | | |
| (±)-Trans-3-(5,6-dihydro-4H-pyrrolo [3,2,1-ij] quinolin-1yl)-4-(2,4-dichlorophenyl) pyrrolidine-2,5-dione | 48 | 14.8 | | | | |
| (±)-Trans-3-(5,6-dihydro-4H-pyrrolo [3,2,1-ij] quinolin-1yl)-4-phenyl-pyrrolidine-2,5-dione | 49 | 12 | | | | |
| (±)-Trans-3-(5,6-dihydro-4H-pyrrolo [3,2,1-ij] quinolin-1yl)-4-(2-chlorophenyl)-pyrrolidine-2,5-dione | 50 | 4.56 | 4.22 | 4.65 | | |
| (±)-Trans-3-(5,6-dihydro-4H-pyrrolo [3,2,1-ij] quinolin-1yl)-4-(N-methylindol-3-yl) pyrrolidine-2,5-dione | 51 | 67.3 | 65.7 | 37.7 | | |
| (±)-Cis-3-(5,6-dihydro-4H-pyrrolo [3,2,1-ij] quinolin-1yl)-4-(2,5-dimethoxyphenyl)-pyrrolidine-2,5-dione | 53 | >100 | | | >100 | >100 | 57.4 |
| (±)-Cis-3-(5,6-dihydro-4H-pyrrolo [3,2,1-ij] quinolin-1yl)-4-(2-chloro-4-fluoro-phenyl)-pyrrolidine-2,5-dione | 54 | 9.3 | | | 11.5 | 25.2 | 6.88 |
| (±)-Cis-3-(5,6-dihydro-4H-pyrrolo [3,2,1-ij] quinolin-1yl)-4-(3-chlorophenyl)-pyrrolidine-2,5-dione | 55 | 15.54 | | | 12.9 | >100 | 11.6 |

TABLE 2-continued

| | | | | | |
|---|---|---|---|---|---|
| Phosphoric acid dibenzyl ester trans-3-(5,6-dihydro-4H-pyrrolo[3,2,1-ij]quinolin-1-yl)-4-(1H-indol-3-yl)-2,5-dioxo-pyrrolidin-1-ylmethyl ester | 56 | >100 | | | |
| (±)-Phosphoric acid mono-[trans-3-(5,6-dihydro-4H-pyrrolo[3,2,1-ij]quinolin-1-yl)-4-(1H-indol-3-yl)-2,5-dioxo-pyrrolidin-1-ylmethyl] ester | 56 | 5.89 | | | |
| (±)-trans-2-Amino-propionic acid-3-(5,6-dihydro-4H-pyrrolo[3,2,1-ij]quinolin-1-yl)-4-(1H-indol-3-yl)-2,5-dioxo-pyrrolidin-1-yl methyl ester | 57 | 3.14 | | | |
| (±)-trans-Amino-acetic acid-3-(5,6-dihydro-4H-pyrrolo[3,2,1-ij]quinolin-1-yl)-4-(1H-indol-3-yl)-2,5-dioxo-pyrrolidin-1-yl methyl ester | 58 | 3.45 | | | |
| (±)-trans-dimethylamino-acetic acid-3-(5,6-dihydro-4H-pyrrolo[3,2,1-ij]quinolin-1-yl)-4-(1H-indol-3-yl)-2,5-dioxo-pyrrolidin-1-ylmethyl ester | 59 | 4.47 | | | |
| (±)-trans-Isonicotinic acid-3-(5,6-dihydro-4H-pyrrolo[3,2,1-ij]quinolin-1-yl)-4-(1H-indol-3-yl)-2,5-dioxo-pyrrolidin-1-ylmethyl ester | 60 | 3.55 | | | |
| (±)-cis-3-(5,6-dihydro-4H-pyrrolo[3,2,1-ij] quinolin-1-yl)-4(1-methylindol-3-yl)-1-methyl pyrrolidine-2,5-dione | 61 | >100 | >100 | >100 | 37.6 |
| 3-(5,6-Dihydro-4H-pyrrolo[3,2,1-ij]quinolin-1-yl)-4-(3-methoxyphenyl)-1H-pyrrole-2,5-dione | 65 | 60.8 | | | |
| 3-[4-(Benzyloxy)phenyl]-4-(5,6-dihydro-4H-pyrrolo[3,2,1-ij]quinolin-1-yl)-1H-pyrrole-2,5-dione | 66 | >100 | | | |
| 3-(5,6-Dihydro-4H-pyrrolo[3,2,1-ij]quinolin-1-yl)-4-(4-fluorophenyl)-1H-pyrrole-2,5-dione | 67 | 57 | | | |
| (±)-Trans-3-(5,6-dihydro-4H-pyrrolo[3,2,1-ij]quinolin-1-yl)-4-(3-methoxyphenyl)pyrrolidine-2,5-dione | 68 | 14.7 | | | |
| (±)-Trans-3-(5,6-dihydro-4H-pyrrolo[3,2,1-ij]quinolin-1-yl)-4-(3-hydroxyphenyl)pyrrolidine-2,5-dione | 69 | 65.9 | | | |
| (±)-Trans-3-(5,6-dihydro-4H-pyrrolo[3,2,1-ij]quinolin-1-yl)-4-(4-fluorophenyl)pyrrolidine-2,5-dione | 70 | 49.2 | | | |
| (±)-Trans-3-[4-(benzyloxy)phenyl]-4-(5,6-dihydro-4H-pyrrolo[3,2,1-ij]quinolin-1-yl)pyrrolidine-2,5-dione | 71 | 97.5 | | | |
| (±)-Trans-3-(5,6-dihydro-4H-pyrrolo[3,2,1-ij]quinolin-1-yl)-4-(4-hydroxyphenyl)pyrrolidine-2,5-dione | 72 | >100 | | | |
| 7-[4-(1H-indol-3-yl)-2,5-dioxo-2,5-dihydro-1H-pyrrol-3-yl]-3,4-dihydro-1H-[1,4]diazepino[6,7,1-hi]indole-2-carboxylic acid benzyl ester | 73 | >100 | | | |
| (±)-Trans-7-[4-(1H-indol-3-yl)-2,5-dioxo-pyrrolidin-3-yl]-3,4-dihydro-1H-[1,4]diazepino[6,7,1-hi]indole-2-carboxylic acid benzyl ester | 74 | >100 | | | |

TABLE 2-continued

| | | |
|---|---|---|
| (±)-Trans-3-(1H-indol-3-yl)-4-(1,2,3,4-tetrahydro-[1,4]diazepino[6,7,1-hi]indol-7-yl)-pyrrolidine-2,5-dione | 75 | >100 |

Example 77

Figure 1:
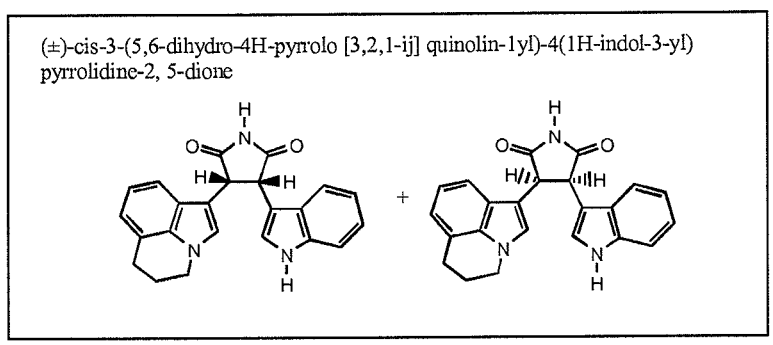
FIG. 1 sets forth the chemical structures of (±)-cis-3-(5,6-dihydro-4H-pyrrolo[3,2,1-ij]quinolin-1yl)-4(1H-indol-3-yl)pyrrolidine-2,5-dione and (±)-trans-3-(5,6-dihydro-4H-pyrrolo[3,2,1-ij]quinolin-1-yl)-4(1H-indol-3-yl)pyrrolidine-2,5-dione.
Figure 1:
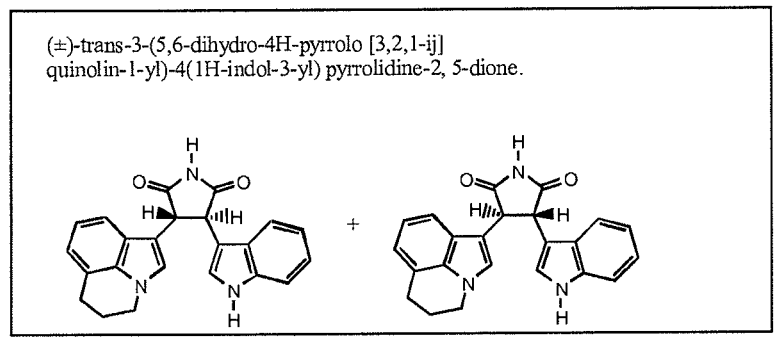
Figure 2:
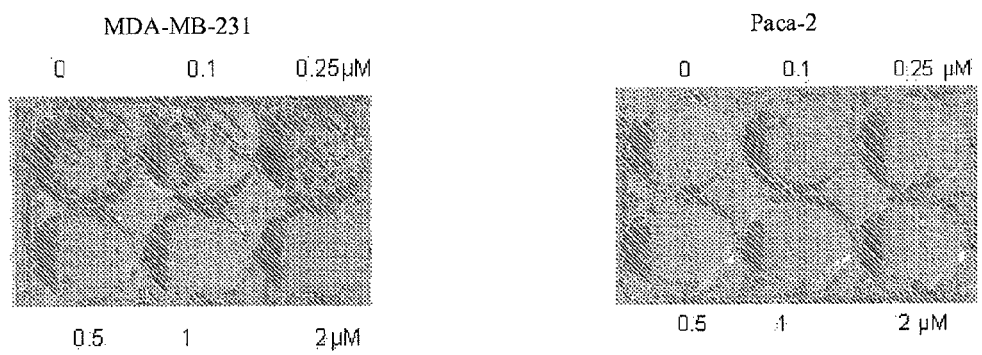
FIG. 2 sets forth an effect of (±)-cis-3-(5,6-dihydro-4H-pyrrolo[3,2,1-ij]quinolin-1yl)-4(1H-indol-3-yl)pyrrolidine-2,5-dione or (±)-trans-3-(5,6-dihydro-4H-pyrrolo[3,2,1-ij]quinolin-1-yl)-4(1H-indol-3-yl)pyrrolidine-2,5-dione on survival of MDA-MB-231 or Paca-2 cells in vitro.
Figure 2:
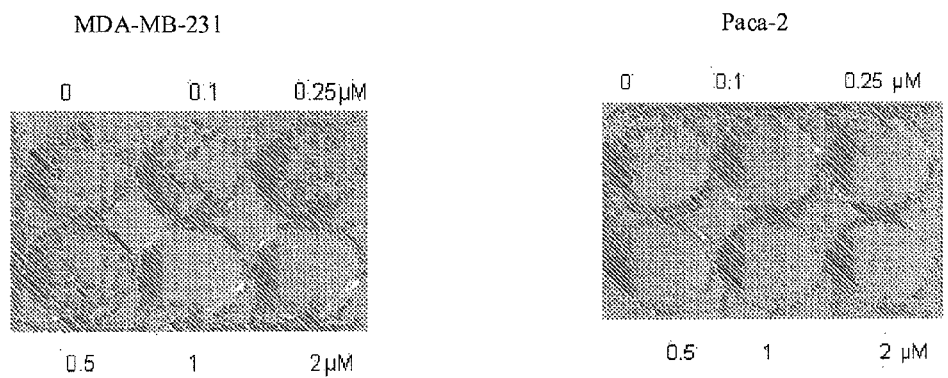

Exponentially growing MDA-MB-231 cells or Paca-2 cells were seeded at 1,000 cells per well in six-well plates and allowed to attach for 24 hours. MDA-MB-231 and Paca-2 cells were cultured in DMEM supplemented with 10% (v/v) fetal calf serum (FCS) and 5 ml Penicillin/Streptomycin at 37° C. in 5% $CO_2$. MDA-MB-231 and Paca-2 were established estrogen receptor negative human breast cancer and pancreatic carcinoma cell lines, respectively. (±)-cis-3-(5,6-dihydro-4H-pyrrolo[3,2,1-ij]quinolin-1yl)-4(1H-indol-3-yl)pyrrolidine-2,5-dione or (±)-trans-3-(5,6-dihydro-4H-pyrrolo[3,2,1-ij]quinolin-1-yl)-4(1H-indol-3-yl)pyrrolidine-2,5-dione were each dissolved at a concentration of 10 mM in DMSO, and separately added to cells at a concentration of 0.1, 0.25, 0.5, 1 or 2 µM. Control plates received DMSO alone, at the same percentage of total culture volume as that administered in conjunction with the highest concentration of drug. Cell cultures were observed daily for 10-15 days, then fixed and stained with modified Wright-Giemsa stain (Sigma). Treatment with (±)-cis-3-(5,6-dihydro-4H-pyrrolo[3,2,1-ij]quinolin-1yl)-4(1H-indol-3-yl)pyrrolidine-2,5-dione or (±)-trans-3-(5,6-dihydro-4H-pyrrolo[3,2,1-ij]quinolin-1-yl)-4(1H-indol-3-yl)pyrrolidine-2,5-dione results in cell death of MDA-MB-231 cells or Paca-2 cells. See, e.g., FIG. 2. The $IC_{50}$ for (±)-cis-3-(5,6-dihydro-4H-pyrrolo[3,2,1-ij]quinolin-1yl)-4(1H-indol-3-yl) pyrrolidine-2,5-dione was found to be 0.5 µM. The $IC_{50}$ for (±)-trans-3-(5,6-dihydro-4H-pyrrolo[3,2,1-ij]quinolin-1-yl)-4(1H-indol-3-yl) pyrrolidine-2,5-dione was found to be 0.5 µM.

Example 78

Figure 3:
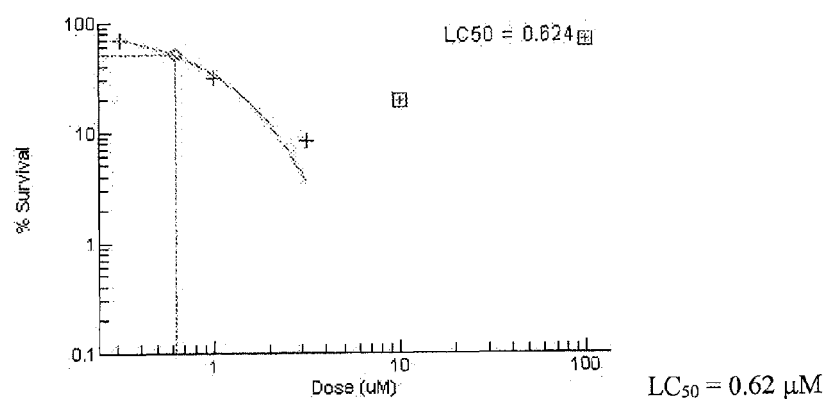
FIG. 3 sets forth an effect of (−)-trans-3-(5,6-dihydro-4H-pyrrolo[3,2,1-ij]quinolin-1-yl)-4(1H-indol-3-yl)pyrrolidine-2,5-dione or (+)-trans-3-(5,6-dihydro-4H-pyrrolo[3,2,1-ij]quinolin-1-yl)-4(1H-indol-3-yl)pyrrolidine-2,5-dione on survival of MDA-MB-231 cells in vitro.
Figure 3:
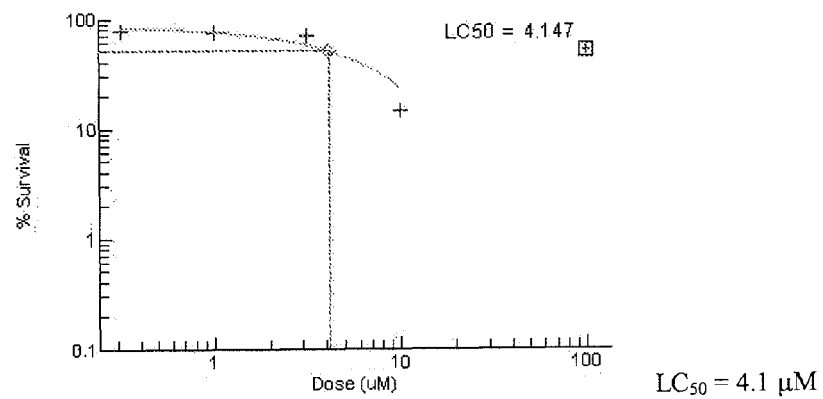

MDA-MB-231 cells (ATCC#HTB-26), grown in DMEM plus 15% heat inactivated fetal bovine serum plus 10 mM HEPES pH 7.5, were plated in 60 mm plates ($2\times10^5$ cells per plate). After two days candidate compounds in DMSO at various concentrations were diluted in media and added to individual plates such that the final DMSO concentration in the cell culture media was 0.1%. After two days incubation the culture was trypsinized, cells were washed with media, counted using a hemocytometer and 500 cells, including cell bodies, were plated in 100 mM plates in media. Two weeks later the media was removed and the cell colonies were fixed with methanol for 10 minutes, stained with 1% crystal violet 10 minutes, washed with water and airdried. Cell colonies were visually counted when there were greater then 50 cells present per colony. Plating efficiency was defined as the average number of colonies formed divided by 500. The surviving fraction was defined as the plating efficiency of a candidate compound divided by the plating efficiency of DMSO multiplied by 100. For candidate compound titrations, the $IC_{50}$ concentration was determined by fitting the equation $y=Ae^{Bx}$ to the data points and extrapolating the concentration where surviving fraction equaled 50. Treatment with (−)-trans-3-(5,6-dihydro-4H-pyrrolo[3,2,1-ij]quinolin-1-yl)-4(1H-indol-3-yl) pyrrolidine-2,5-dione or (+)-trans-3-(5,6-dihydro-4H-pyrrolo[3,2,1-ij]quinolin-1-yl)-4(1H-indol-3-yl)pyrrolidine-2,5-dione results in cell death of MDA-MB-231 cells. See, e.g., FIG. 3. The $IC_{50}$ for (−)-trans-3-(5,6-dihydro-4H-pyrrolo[3,2,1-ij]quinolin-1-yl)-4(1H-indol-3-yl)pyrrolidine-2,5-dione was found to be 0.62 µM. The $IC_{50}$ for (+)-trans-3-(5,6-dihydro-4H-pyrrolo[3,2,1-ij]quinolin-1-yl)-4(1H-indol-3-yl)pyrrolidine-2,5-dione was found to be 4.1 µM.

Example 79

Recombinant Protein Kinase C (Calbiochem) (100 ng) was incubated with (±)-cis-3-(5,6-dihydro-4H-pyrrolo[3,2,1-ij]quinolin-1yl)-4(1H-indol-3-yl)pyrrolidine-2,5-dione or (±)-trans-3-(5,6-dihydro-4H-pyrrolo[3,2,1-ij]quinolin-1-yl)-4(1H-indol-3-yl)pyrrolidine-2,5-dione at 0.05, 0.5, or 1 µM for 15 minutes at room temperature. Subsequently, a radioactive labeling mix in kinase buffer (20 mM Tris-HCl pH 7.5, 10 mM $MgCl_2$) containing 20 LM ATP, 0.2 µCi/µl $\gamma^{32}$P-ATP, 0.2 µg/µl Histone H1 (Upstate) was added to each sample. The kinase reaction was carried out for 5 minutes at room temperature. Reaction products were analyzed by 12% SDS-PAGE and autoradiography.

Figure 4:
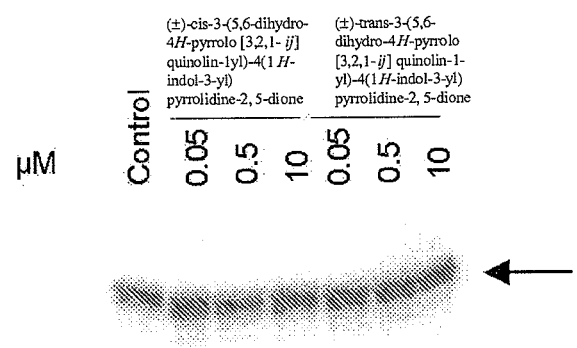
FIG. 4 sets forth an effect of (±)-cis-3-(5,6-dihydro-4H-pyrrolo[3,2,1-ij]quinolin-1yl)-4(1H-indol-3-yl)pyrrolidine-2,5-dione or (±)-trans-3-(5,6-dihydro-4H-pyrrolo[3,2,1-ij]quinolin-1-yl)-4(1H-indol-3-yl)pyrrolidine-2,5-dione on Protein Kinase C activity in vitro.

Treatment of recombinant Protein Kinase C for 15 minutes at room temperature with (±)-cis-3-(5,6-dihydro-4H-pyrrolo[3,2,1-ij]quinolin-1yl)-4(1H-indol-3-yl)pyrrolidine-2,5-dione or (±)-trans-3-(5,6-dihydro-4H-pyrrolo[3,2,1-ij]quinolin-1-yl)-4(1H-indol-3-yl)pyrrolidine-2,5-dione at the tested concentrations did not reduce kinase activity in comparison to treatment with carrier alone. See, e.g., FIG. 4.

Example 80

Figure 5:
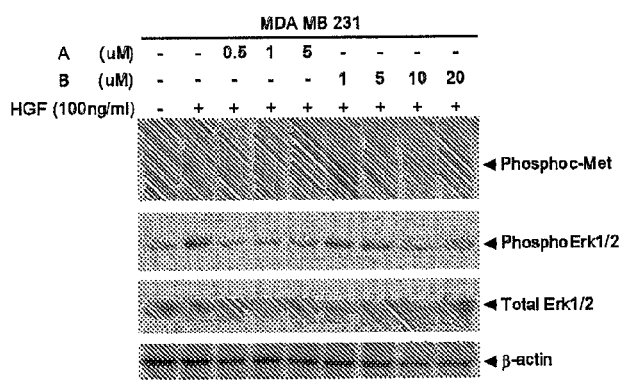
FIG. 5 sets forth inhibition of c-Met phosphorylation and ERK1/2 phosphorylation by (−)-trans-3-(5,6-dihydro-4H-pyrrolo[3,2,1-ij]quinolin-1-yl)-4(1H-indol-3-yl)pyrrolidine-2,5-dione or (+)-trans-3-(5,6-dihydro-4H-pyrrolo[3,2,1-ij]quinolin-1-yl)-4(1H-indol-3-yl)pyrrolidine-2,5-dione.

MDA-MB-231 cells were serum-deprived overnight (16 hours) in the absence or in the presence of the indicated concentrations of the separate enantiomers (+)-trans-3-(5,6-dihydro-4H-pyrrolo[3,2,1-ij]quinolin-1-yl)-4(1H-indol-3-yl)pyrrolidine-2,5-dione and (−)-trans-3-(5,6-dihydro-4H-pyrrolo[3,2,1-ij]quinolin-1-yl)-4(1H-indol-3-yl)pyrrolidine-2,5-dione. Cells were treated with 100 ng/ml recombinant human Hepatocyte Growth Factor/Scatter Factor (HGF/SF) (R&D Systems #294-HG) for 10 minutes. Whole cell extracts were prepared in lysis buffer (20 mM Trwas-HCl pH 7.5, 150 mM NaCl, 1 mM $Na_2EDTA$, 1 mM EGTA, 1% Triton X-100, 2.5 mM sodium pyrophosphate, 1 mM beta-glycerophosphate, 1 mM $Na_3VO_4$, 1 µg/ml leupeptin, 1 mM phenylmethylsulfonyl fluoride) and sonicated. Protein concentration was measured by Bradford assay using the Bio-Rad reagent (BioRad, Hercules, Calif.), according to the manufacturer's directions. Samples (50 µg of protein) were resolved by 8% SDS-PAGE under reducing conditions, and transferred onto a PVDF membrane (BioRad). The membrane was incubated 1 hour in TBS-T (50 mM Trwas-HCl pH 7.6, 200 mM NaCl, 0.05% Tween 20) with 5% milk. Proteins were detected by incubation overnight at 4° C. in TBS-T with 5% milk and either a polyclonal antibody against phosphorylated c-Met (#3121), phosphorylated Erk1/2 (#9101), total Erk1/2 protein (#9102) (Cell Signaling Technology); or a monoclonal antibody against β-actin (A-5441) (Sigma), which was used as a control for total protein loading. After extensive washing in TBS-T, a horseradish peroxidase-conjugated anti-rabbit IgG (1:5000) or anti-mouse IgG (1:2000) (Amersham Biosciences) was added for 1 hour, and specific protein bands visualized using an enhanced chemiluminescence detection system (Amersham Biosciences), according to the manufacturer's instructions. See, e.g., FIG. 5.

Treatment with (−)-trans-3-(5,6-dihydro-4H-pyrrolo[3,2,1-ij]quinolin-1-yl)-4(1H-indol-3-yl) pyrrolidine-2,5-dione inhibits both basal and HGF-induced autophosphorylation of c-Met at a concentration of at least 500 nM. (+)-trans-3-(5,6-dihydro-4H-pyrrolo[3,2,1-ij]quinolin-1-yl)-4(1H-indol-3-yl)pyrrolidine-2,5-dione has a partial inhibitory effect on c-Met phosphorylation at greater concentrations (10 to 20 µM). Additionally, (−)-trans-3-(5,6-dihydro-4H-pyrrolo[3,2,1-ij]quinolin-1-yl)-4(1H-indol-3-yl)pyrrolidine-2,5-dione decreases the phosphorylation of ERK1/2; a well-known downstream target in the signaling of the c-Met tyrosine kinase receptor. See, e.g., FIG. 5.

Example 81

Athymic female nude mice (CRL:NU/NU-nuBR) were injected subcutaneously in the flank with MDA-MB-231 human breast cancer cells ($8 \times 10^6$ cells/mouse). Prior to injection, MDA-MB-231 cells were cultured in DMEM (Invitrogen #11965-092) supplemented with 10% (v/v) heat inactivated fetal bovine serum (FBS), 1% Hepes buffer solution (Invitrogen #15630-080) and 1% Penicillin/Streptomycin (Invitrogen #15140-122) at 37° C. in 5% $CO_2$. Tumors were allowed to grow to approximately 50 $mm^3$ in size. Animals were randomized into three groups of five animals per group. At day ten post injection, mice with established tumors were treated intraperitoneally with (±)-cis-3-(5,6-dihydro-4H-pyrrolo[3,2,1-ij]quinolin-1yl)-4(1H-indol-3-yl)pyrrolidine-2,5-dione (160 mg/kg), (±)-trans-3-(5,6-dihydro-4H-pyrrolo[3,2,1-ij]quinolin-1-yl)-4(1H-indol-3-yl)pyrrolidine-2,5-dione (160 mg/kg) administered in iodinated poppy seed oil (lipiodol) as the vehicle at 10 mg/ml, or vehicle control. Drug or vehicle was administered every three days for a total of ten doses (q3d×10). Tumor size was evaluated periodically during the study. For each subject, tumor volume was calculated using the formula $(L \times W^2)/2$ where L and W were the length and width of the tumor, respectively. The arithmetic mean tumor volume was calculated for each treatment group+/−standard error of the mean (SEM). The means for each group were normalized with respect to the mean starting tumor volume in order to determine fold increase in tumor volume. See, e.g., FIG. 6.

Treatment with (±)-cis-3-(5,6-dihydro-4H-pyrrolo[3,2,1-ij]quinolin-1yl)-4(1H-indol-3-yl) pyrrolidine-2,5-dione or (±)-trans-3-(5,6-dihydro-4H-pyrrolo[3,2,1-ij]quinolin-1-yl)-4(1H-indol-3-yl)pyrrolidine-2,5-dione at 160 mg/kg reduced the normalized mean tumor volume of human breast cancer xenograft by 80.5% (p=0.0037) and 43.5% (p=0.133), respectively, compared to vehicle treated control. See, e.g., FIG. 6.

Example 82

Figure 6:
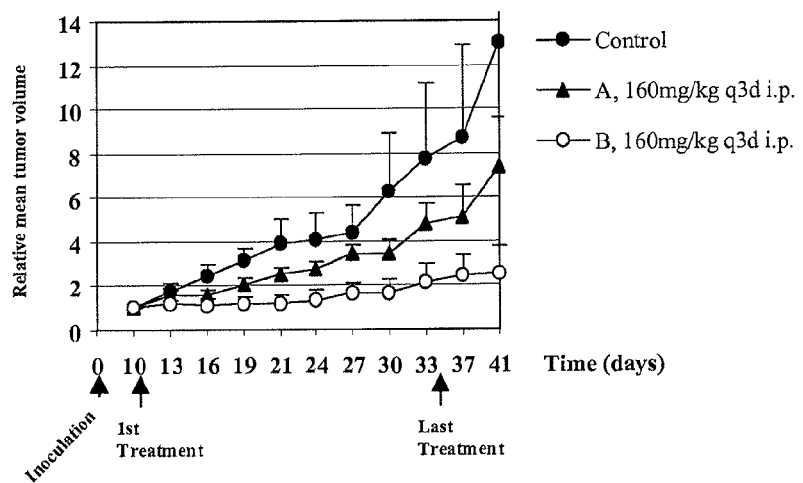
FIG. 6 sets forth an effect of (±)-cis-3-(5,6-dihydro-4H-pyrrolo[3,2,1-ij]quinolin-1yl)-4(1H-indol-3-yl)pyrrolidine-2,5-dione or (±)-trans-3-(5,6-dihydro-4H-pyrrolo[3,2,1-ij]quinolin-1-yl)-4(1H-indol-3-yl)pyrrolidine-2,5-dione, administered individually at 160 mg/kg, on the growth of xenografted MDA-MB-231 human breast cancer tumors in athymic female nude mice.

Athymic female nude mice (CRL:NU/NU-nuBR) were injected subcutaneously in the flank with MDA-MB-231 human breast cancer cells ($8 \times 10^6$ cells/mouse). Prior to injection, MDA-MB-231 cells were cultured in DMEM (Invitrogen #11965-092) supplemented with 10% (v/v) heat inactivated fetal bovine serum (FBS), 1% Hepes buffer solution (Invitrogen #15630-080) and 1% Penicillin/Streptomycin (Invitrogen #15140-122) at 37° C. in 5% $CO_2$. Tumors were allowed to grow to approximately 50 $mm^3$ in size. Animals were randomized into three groups of eight animals per group. At day four post injection, mice with established tumors were treated intraperitoneally with (±)-Cis-3-(5,6-dihydro-4H-pyrrolo[3,2,1-ij]quinolin-1yl)-4(1H-indol-3-yl)pyrrolidine-2,5-dione (80 mg/kg), (±)-Trans-3-(5,6-dihydro-4H-pyrrolo[3,2,1-ij]quinolin-1-yl)-4(1H-indol-3-yl)pyrrolidine-2,5-dione (80 mg/kg) administered in DMA/PEG 400 (1:4 v/v) as the vehicle at 50 mg/ml, or vehicle control intraperitoneally. Drug or vehicle was administered once per day for five consecutive days followed by two consecutive days of no treatment (one cycle of dose administration). A total of four cycles of treatment were administered. Tumor size was evaluated periodically during the study. For each subject, tumor volume was calculated using the formula $(L \times W^2)/2$ where L and W were the length and width of the tumor, respectively. The arithmetic mean tumor volume was calculated for each treatment group+/−standard error of the mean (SEM). Each data point in FIG. 6 represents the arithmetic mean+/−standard error of the mean (SEM) of eight tumors.

Figure 7:
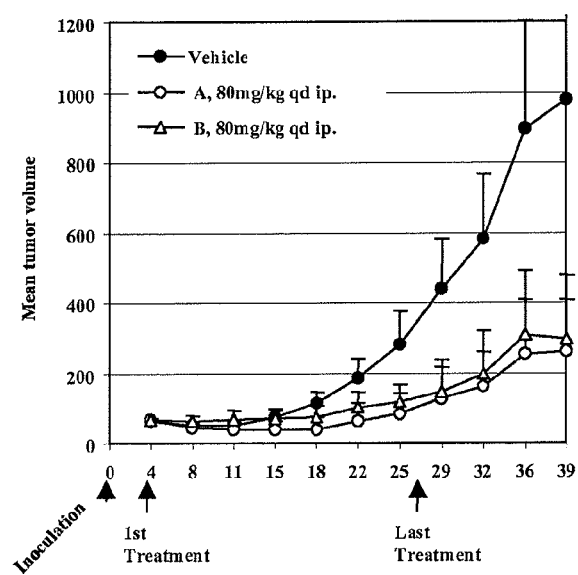
FIG. 7 sets forth an effect of (±)-cis-3-(5,6-dihydro-4H-pyrrolo[3,2,1-ij]quinolin-1yl)-4(1H-indol-3-yl)pyrrolidine-2,5-dione or (±)-trans-3-(5,6-dihydro-4H-pyrrolo[3,2,1-ij]

Treatment with (±)-cis-3-(5,6-dihydro-4H-pyrrolo[3,2,1-ij]quinolin-1yl)-4(1H-indol-3-yl) pyrrolidine-2,5-dione or (±)-trans-3-(5,6-dihydro-4H-pyrrolo[3,2,1-ij]quinolin-1-yl)-4(1H-indol-3-yl)pyrrolidine-2,5-dione at 80 mg/kg reduced the mean tumor volume of human breast cancer xenograft by 73.4% (p=0.04) and 69.4% (p=0.075), respectively, compared to vehicle treated control. See, e.g., FIG. 7.

Example 83

(−)-trans-3-(5,6-dihydro-4H-pyrrolo[3,2,1-ij]quinolin-1-yl)-4(H-indol-3-yl) pyrrolidine-2,5-dione Induces Cell Death of a Wide Range of Tumor Cells, Which Correlates with its Ability of Inhibiting c-Met Phosphorylation

| Cells | Tissue | Expression levels of c-Met | Constitutive activity of c-Met | (−)-trans $IC_{50}$ (µM) c-Met Inhibition | CFA |
|---|---|---|---|---|---|
| H661 | Lung (NSCLC) | Null | no | na | 5 |
| H446 | Lung (SCLC) | Null | no | na | 4 |
| MCF-7 | Breast | Low | yes | 0.1 | 0.4 |
| MDA-MB-231 | Breast | Medium | no | 0.1 | 0.3 |
| DLD-1 | Colon | Medium | yes | 3 | 0.7 |
| HT-29 | Colon | High | no | 0.3 | 0.2 |
| PACA2 | Pancreas | High | yes | 0.1 | 0.3 |
| PANC-1 | Pancreas | High | no | 0.5 | 0.5 |
| H441 | Lung (NSCLC) | Very high | no | 0.1 | 0.2 |

CFA = Colony Formation Assay
na = Not Applicable

To determine c-met inhibition, exponentially growing MCF-7 and MDA-MB-231 human breast cancer cells, DLD 1 and HT29 human colon cancer cells, PACA2 and PANC-1 human pancreatic cancer cells and NCI-H441 human non-small cell lung cancer cells (H441) were serum starved in 0.5% FBS and treated with increasing amounts of (−)-trans-3-(5,6-dihydro-4H-pyrrolo[3,2,1-ij]quinolin-1-yl)-4(1H-indol-3-yl)pyrrolidine-2,5-dione for 24 hours as indicated. Cells were then left unstimulated or stimulated with 100 ng/mL HGF for 10 minutes and whole cell extracts were prepared. Whole cell lysates (50 µg) were resolved by SDS-PAGE, transferred onto a PVDF membrane, and an enhanced chemiluminescence assay system (ECL) was used to determine the phosphorylation status of c-Met. A polyclonal antibody against phospho (Y1349) c-Met (phospho-c-Met) was obtained from Biosource International and a monoclonal antibody against β-actin was purchased from Invitrogen. Percent inhibition was determined by densitometry using the Scion Image For colony formation assays (CFA), exponentially growing cells were seeded at 2,000 cells per well in 6-well plates and allowed to attach for 24 hours. Increasing concentrations of (−)-trans-3-(5,6-dihydro-4H-pyrrolo[3,2,1-ij]quinolin-1-yl)-4(1 H-indol-3-yl)pyrrolidine-2,5-dione (from 0.01 to 30 μM) were then added to the media for another 24 hours. After 24 hours exposure, the drug was removed and fresh media was added for the next 14-21 days, allowing for colony formation. Cells were fixed and stained with GEMSA (Gibco BRL). Colonies of greater than 50 cells were scored as survivors and percentage of cell survival was plotted to determine the $IC_{50}$.

(−)-trans-3-(5,6-dihydro-4H-pyrrolo[3,2,1-ij]quinolin-1-yl)-4(1H-indol-3-yl)pyrrolidine-2,5-dione was found to potently inhibit growth and induce apoptosis across a wide range of human tumor cell lines. The $IC_{50}$ of (−)-trans-3-(5,6-dihydro-4H-pyrrolo[3,2,1-ij]quinolin-1-yl)-4(1H-indol-3-yl)pyrrolidine-2,5-dione for c-Met expressing solid tumor types is in the 0.1-0.7 μM range following exposure to (−)-trans-3-(5,6-dihydro-4H-pyrrolo[3,2,1-ij]quinolin-1-yl)-4(H-indol-3-yl)pyrrolidine-2,5-dione for 24 hours, as determined by colony formation assay (CFA). More notably cells lacking c-Met such as NCI-H661 (human non-small cells lung cancer cells) and NCI-H446 (human small lung cancer cells) yielded $IC_{50}$s approximately 10-fold higher for (−)-trans-3-(5,6-dihydro-4H-pyrrolo[3,2,1-ij]quinolin-1-yl)-4(1H-indol-3-yl)pyrrolidine-2,5-dione, strongly indicating a correlation between the presence of c-Met and the cytotoxic sensitivity of the cells towards (−)-trans-3-(5,6-dihydro-4H-pyrrolo[3,2,1-ij]quinolin-1-yl)-4(1H-indol-3-yl)pyrrolidine-2,5-dione. It should be noted that the $IC_{50}$ of (−)-trans-3-(5,6-dihydro-4H-pyrrolo[3,2,1-ij]quinolin-1-yl)-4(1H-indol-3-yl) pyrrolidine-2,5-dione on c-Met inhibition and cellular cytotoxicity after 24 hours treatment are highly comparable in c-Met expressing cancer cells.

Example 84

(−)-trans-3-(5,6-dihydro-4H-pyrrolo[3,2,1-ij]quinolin-1-yl)-4(1H-indol-3-yl) pyrrolidine-2,5-dione Induces Apoptosis in Cancer Cells A549 human lung cancer cells in a 96-well plate (Costar 3603, 5,000/well) were treated with either A) DMSO as a control; B) 1.2 μM (−)-trans-3-(5,6-dihydro-4H-pyrrolo[3,2,1-ij]quinolin-1-yl)-4(1H-indol-3-yl)pyrrolidine-2,5-dione for 38 hours before addition of 1:200 fluorescent Annexin V (green) and 1:500 Propidium iodide (magenta, final concentration of 1 μg/mL). The labeling procedure was allowed to process at 37° C. for 20 minutes followed by image acquisition and analysis using an IC100 Image Cytometer (Beckman Coulter, Inc) with 10× amplification.

To determine whether (−)-trans-3-(5,6-dihydro-4H-pyrrolo[3,2,1-ij]quinolin-1-yl)-4(1H-indol-3-yl)pyrrolidine-2,5-dione works primarily through a cytostatic or apoptotic mechanism, cancer cells exposed to (−)-trans-3-(5,6-dihydro-4H-pyrrolo[3,2,1-ij]quinolin-1-yl)-4(1H-indol-3-yl)pyrrolidine-2,5-dione were stained with fluorescently labeled Annexin V (green fluorescence) and propidium iodide (bright magenta fluorescence). Annexin V is a well-validated reagent that specifically binds with high affinity to externalized membrane phosphatidylserine, an early marker of the onset of apoptosis, while propidium iodide is a marker for dead cells. Incubation of human lung cancer cells (A549) with 1.2 μM (−)-trans-3-(5,6-dihydro-4H-pyrrolo[3,2,1-ij]quinolin-1-yl)-4(1H-indol-3-yl)pyrrolidine-2,5-dione for 38 hours induced cells to undergo apoptosis as evidenced by strong Annexin V staining. A small percentage of cells (~10-20%) co-stain with both Annexin V and propidium iodide, indicating that a sub-population of (−)-trans-3-(5,6-dihydro-4H-pyrrolo[3,2,1-ij]quinolin-1-yl)-4(1H-indol-3-yl)pyrrolidine-2,5-dione treated cells were already dead within 38 hours. These data are consistent with (−)-trans-3-(5,6-dihydro-4H-pyrrolo[3,2,1-ij]quinolin-1-yl)-4(1H-indol-3-yl)pyrrolidine-2,5-dione inducing cell death largely through activation of apoptotic mechanisms. (See FIG. 8)

Example 85

(−)-trans-3-(5,6-dihydro-4H-pyrrolo[3,2,1-ij]quinolin-1-yl)-4(1H-indol-3-yl) pyrrolidine-2,5-dione Inhibits Metastatic Cancer Cell Invasion MDA-MB-231 cells were pretreated with indicated concentrations of (−)-trans-3-(5,6-dihydro-4H-pyrrolo[3,2,1-ij]quinolin-1-yl)-4(1H-indol-3-yl)pyrrolidine-2,5-dione for 24 hours. 300 μl of each cell suspension (at a concentration $0.5 \times 10^6$ cells/mL in serum free medium) was placed in individual inserts and incubated for 24 hours at 37° C. The bottom wells housing the inserts contained 500 μl of 10% FBS medium. At 24 hours the media from the inserts was aspirated and cells that failed to invade were gently removed from the interior of the inserts with a cotton tipped swab. Each insert was then transferred to a clean well containing cell stain solution and incubated for 10 minutes at room temperature. The bottom of the insert was destained by incubating in extraction solution and OD was measured at 560 nM. (−)-trans-3-(5,6-dihydro-4H-pyrrolo[3,2,1-ij]quinolin-1-yl)-4(1H-indol-3-yl) pyrrolidine-2,5-dione inhibited the migration across interstices in confluent cultures of MDA-MB-231 cancer cells. The data represent the mean of two independent experiments. (See FIG. 9)

The morbidity and mortality resulting from most cancers is the result of local invasion and metastasis from the primary tumors to other tissues. This process mostly depends on the motility and growth of tumor cells. Activation of c-Met by HGF induces a variety of cellular responses including motility, invasion, wound healing and tissue regeneration. It has been established that aberrant activation of c-Met plays a critical role in the development and progression of primary tumors and secondary metastases. HGF has the ability to dissociate epithelial sheets, to stimulate cell motility and invasion through extracellular matrix substrates and HGF production correlates with tumor metastasis in vivo.

As shown above, (−)-trans-3-(5,6-dihydro-4H-pyrrolo[3,2,1-ij]quinolin-1-yl)-4(1H-indol-3-yl)pyrrolidine-2,5-dione inhibited the invasive phenotype of MDA-MB-231 breast cancer cells with an estimated $IC_{50}$ of approximately 500 nM. Similar results were seen with brain and lung cancer cells (data not shown).

Example 86

Breast Cancer Xenograft Model (−)-trans-3-(5,6-dihydro-4H-pyrrolo[3,2,1-ij]quinolin-1-yl)-4(1H-indol-3-yl)pyrrolidine-2,5-dione shows efficacy in a human breast cancer xenograft. MDA-MB-231 human breast cancer cells were inoculated subcutaneously into female athymic nude mice (8.0×10$^6$ cells/mouse) and allowed to form palpable tumors. Once the tumors reached approximately 60 mm$^3$, the animals were treated orally with (−)-trans-3-(5,6-dihydro-4H-pyrrolo[3,2,1-ij]quinolin-1-yl)-4(1H-indol-3-yl)pyrrolidine-2,5-dione at 200 mg/kg or vehicle control daily (5 consecutive days, followed by a 2 day dosing holiday). (−)-trans-3-(5,6-dihydro-4H-pyrrolo[3,2,1-ij]quinolin-1-yl)-4(1H-indol-3-yl)pyrrolidine-2,5-dione was formulated in PEG 400:20% Vitamin E TPGS (60:40). The animals received a total of 20 doses of (−)-trans-3-(5,6-dihydro-4H-pyrrolo[3,2,1-ij]quinolin-1-yl)-4(1H-indol-3-yl)pyrrolidine-2,5-dione or vehicle control. Tumors were measured throughout treatment and the post-treatment observation period. Each point represents the mean±SEM often tumors. (See FIG. 10)

Treatment with (−)-trans-3-(5,6-dihydro-4H-pyrrolo[3,2,1-ij]quinolin-1-yl)-4(1H-indol-3-yl) pyrrolidine-2,5-dione as monotherapy was effective at slowing tumor growth. Tumor growth inhibition of (−)-trans-3-(5,6-dihydro-4H-pyrrolo[3,2,1-ij]quinolin-1-yl)-4(1H-indol-3-yl) pyrrolidine-2,5-dione was calculated to be 79% and was statistically significant (p=0.009). There was no significant change in body weight due to oral administration of the vehicle or (−)-trans-3-(5,6-dihydro-4H-pyrrolo[3,2,1-ij]quinolin-1-yl)-4(1H-indol-3-yl)pyrrolidine-2,5-dione at 200 mg/kg.

Example 87

Colon Cancer Xenograft Model

In this human colon cancer xenograft model HT29 human colon cancer cells were inoculated subcutaneously into female athymic nude mice (5×10$^6$ cells/mouse) and allowed to form palpable tumors. Once the tumors reached approximately 60 mm$^3$, the animals were treated orally with either (−)-trans-3-(5,6-dihydro-4H-pyrrolo[3,2,1-ij]quinolin-1-yl)-4(1H-indol-3-yl)pyrrolidine-2,5-dione at 200 mg/kg or 300 mg/kg, or vehicle control daily (5 consecutive days, followed by a 2 day dosing holiday). (−)-trans-3-(5,6-dihydro-4H-pyrrolo[3,2,1-ij]quinolin-1-yl)-4(1H-indol-3-yl) pyrrolidine-2,5-dione was formulated in PEG 400:20% Vitamin E TPGS (60:40). The animals received a total of 20 treatments of either (−)-trans-3-(5,6-dihydro-4H-pyrrolo[3,2,1-ij]quinolin-1-yl)-4(1H-indol-3-yl) pyrrolidine-2,5-dione or vehicle control. Tumors were measured throughout treatment and the post-treatment observation period. Each point represents the mean±SEM of ten tumors. (See FIG. 11)

In this highly aggressive colon xenograft model, animals dosed with either 200 mg/kg or 300 mg/kg as a monotherapy showed significant tumor growth inhibition, with 300 mg/kg being more efficacious than 200 mg/kg. (−)-trans-3-(5,6-dihydro-4H-pyrrolo[3,2,1-ij]quinolin-1-yl)-4(1H-indol-3-yl)pyrrolidine-2,5-dione dosed at 200 mg/kg showed an optimal tumor growth inhibition of 39% (p=0.006) while 300 mg/kg showed an optimal tumor growth inhibition of 55% (p=0.00001). There was no significant change in body weight due to oral administration of either vehicle control or (−)-trans-3-(5,6-dihydro-4H-pyrrolo[3,2,1-ij]quinolin-1-yl)-4(1H-indol-3-yl)pyrrolidine-2,5-dione at 200 mg/kg or 300 mg/kg.

Example 88

Pancreatic Cancer Xenograft Model (−)-trans-3-(5,6-dihydro-4H-pyrrolo[3,2,1-ij]quinolin-1-yl)-4(1H-indol-3-yl)pyrrolidine-2,5-dione shows efficacy in a human pancreatic cancer xenograft model. PACA-2 human pancreatic cancer cells were inoculated subcutaneously into female athymic nude mice (5×10$^6$ cells/mouse) and allowed to form palpable tumors. Once the tumors reached approximately 60 mm$^3$, the animals were treated orally with (−)-trans-3-(5,6-dihydro-4H-pyrrolo[3,2,1-ij]quinolin-1-yl)-4(1H-indol-3-yl) pyrrolidine-2,5-dione at 200 mg/kg or 300 mg/kg or vehicle control daily (5 consecutive days, followed by a 2 day dosing holiday). (−)-trans-3-(5,6-dihydro-4H-pyrrolo[3,2,1-ij]quinolin-1-yl)-4(1H-indol-3-yl)pyrrolidine-2,5-dione was formulated in PEG 400:20% Vitamin E TPGS (60:40). The animals received a total of 20 doses of (−)-trans-3-(5,6-dihydro-4H-pyrrolo[3,2,1-ij]quinolin-1-yl)-4(1H-indol-3-yl)pyrrolidine-2,5-dione or vehicle control. Tumors were measured throughout treatment and the post-treatment observation period. Each point represents the mean±SEM of ten tumors. (See FIG. 12)

Treatment with (−)-trans-3-(5,6-dihydro-4H-pyrrolo[3,2,1-ij]quinolin-1-yl)-4(1H-indol-3-yl) pyrrolidine-2,5-dione as a monotherapy at either 200 mg/kg or 300 mg/kg showed significant tumor growth inhibition, with 200 mg/kg and 300 mg/kg being equally effective. (−)-trans-3-(5,6-dihydro-4H-pyrrolo[3,2,1-ij]quinolin-1-yl)-4(1H-indol-3-yl)pyrrolidine-2,5-dione dosed at 200 mg/kg showed an optimal tumor growth inhibition of 58% (p=0.036) while 300 mg/kg showed an optimal tumor growth inhibition of 60% (p=0.018). There was no significant change in body weight due to oral administration of either vehicle control or (−)-trans-3-(5,6-dihydro-4H-pyrrolo[3,2,1-ij]quinolin-1-yl)-4(1H-indol-3-yl)pyrrolidine-2,5-dione at 200 mg/kg and 300 mg/kg.

Other embodiments were within the following claims. While several embodiments have been shown and described, various modifications may be made without departing from the spirit and scope of the present invention.

The invention claimed is:
1. A pyrroloquinolinyl-pyrrolidine-2,5-dione compound of formula IVa, IVb, Va, or Vb, or a pharmaceutically acceptable salt thereof:

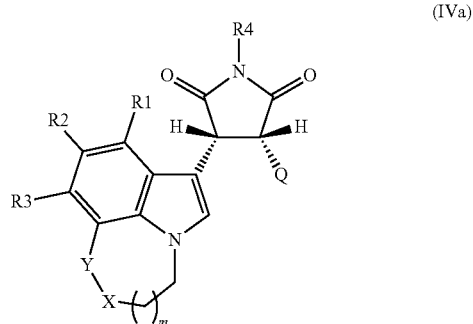

(IVa)

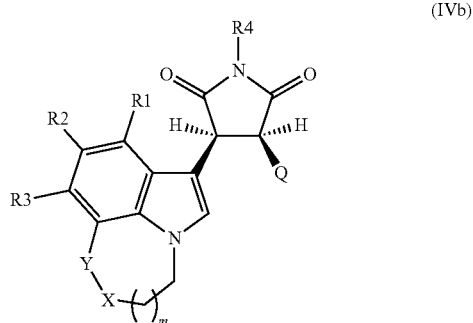

(IVb)

-continued (Va)

(Vb)

wherein:
R1, R2 and R3 are independently selected from the group consisting of hydrogen, F, Cl, Br, I, —NR5R6, —($C_1$-$C_6$) alkyl, —($C_1$-$C_6$) substituted alkyl, —($C_3$-$C_9$) cycloalkyl, —($C_3$-$C_9$) substituted cycloalkyl, —O—($C_1$-$C_6$) alkyl, —O—($C_1$-$C_6$) substituted alkyl, —O—($C_3$-$C_9$) cycloalkyl, —O—($C_3$-$C_9$) substituted cycloalkyl, aryl, heteroaryl, and heterocyclyl;
R4 is selected from the group consisting of hydrogen, —($C_1$-$C_6$) alkyl, and —CH$_2$R7;
R5 and R6 are independently selected from the group consisting of hydrogen and —($C_1$-$C_6$) alkyl;
R7 is selected from the group consisting of —O—P(=O)(OH)$_2$, —O—P(=O)(—OH)(—O—($C_1$-$C_6$) alkyl), —O—P(=O)(—O—($C_1$-$C_6$) alkyl)$_2$, —O—P(=O)(—OH)(—O—(CH$_2$)-phenyl), —O—P(=O)(—O—(CH$_2$)-phenyl)$_2$, a carboxylic acid group, an amino carboxylic acid group, and a peptide;
Q is selected from the group consisting of aryl, heteroaryl, —O-aryl, —S-aryl, —O— heteroaryl, and —S-heteroaryl;
X is (CH$_2$);
Y is a bond; and
m is 1,
wherein said aryl, heteroaryl, —O-aryl, —S-aryl, —O-heteroaryl, and —S-heteroaryl may be substituted with one or more substituents independently selected from the group consisting of F, Cl, Br, I, —NR5R6, —($C_1$-$C_6$) alkyl, —($C_1$-$C_6$) substituted alkyl, —($C_3$-$C_9$) cycloalkyl, —($C_3$-$C_9$) substituted cycloalkyl, —O—($C_1$-$C_6$) alkyl, —O—($C_1$-$C_6$) substituted alkyl, —O—($C_3$-$C_9$) cycloalkyl, —O—($C_3$-$C_9$) substituted cycloalkyl, -aryl, -aryl-($C_1$-$C_6$) alkyl, -aryl-O—($C_1$-$C_6$) alkyl, —O-aryl, —O—($C_1$-$C_4$) alkyl-aryl, heteroaryl, heterocyclyl, —O—($C_1$-$C_4$) alkyl-heterocycle, and —(S(=O)$_2$)—($C_1$-$C_6$) alkyl.

2. The compound of claim 1, wherein Q is an indolyl group or an indolyl group substituted with one or more substituents independently selected from the group consisting of F, Cl, Br, I, —($C_1$-$C_6$) alkyl, —($C_1$-$C_6$) fluoro-substituted alkyl, —($C_3$-$C_9$) cycloalkyl, —($C_3$-$C_9$) fluoro-substituted cycloalkyl, —O—($C_1$-$C_6$) alkyl, —O—($C_1$-$C_6$) fluoro-substituted alkyl, —O—($C_3$-$C_9$) cycloalkyl, —O—($C_3$-$C_9$) fluoro-substituted cycloalkyl, -aryl, —O-aryl, —O—($C_1$-$C_4$) alkyl-aryl, —O—($C_1$-$C_4$) alkyl-heterocycle, and —S(=O)$_2$—($C_1$-$C_6$) alkyl.

3. The compound of claim 1, wherein R4 is —CH$_2$R7, and R7 is —O—P(=O)(OH)$_2$, —O—P(=O)(—OH)(—O—($C_1$-$C_6$) alkyl), —O—P(=O)(—O—($C_1$-$C_6$) alkyl)$_2$, a carboxylic acid group, an amino carboxylic acid group, or a peptide.

4. The compound of claim 3, wherein R7 is —O—P(=O)(OH)$_2$, —O—P(=O)(—OH)(—O—($C_1$-$C_6$) alkyl), or —O—P(=O)(—O—$C_1$-$C_6$)alkyl)$_2$.

5. The compound of claim 3, wherein R7 is a carboxylic acid group, an amino carboxylic acid group, or a peptide.

6. The compound of claim 5, wherein R7 is alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, or valine.

7. The compound of claim 6, wherein R7 is L-alanine, L-arginine, L-asparagine, L-aspartic acid, L-cysteine, L-glutamine, L-glutamic acid, L-glycine, L-histidine, L-isoleucine, L-leucine, L-lysine, L-methionine, L-phenylalanine, L-proline, L-serine, L-threonine, L-tryptophan, L-tyrosine, or L-valine.

8. The compound of claim 5, wherein R7 is a peptide.

9. The compound of claim 8, wherein said peptide is comprised of two or more imino or amino acids selected from the group consisting of: L-alanine, L-arginine, L-asparagine, L-aspartic acid, L-cysteine, L-glutamine, L-glutamic acid, L-glycine, L-histidine, L-isoleucine, L-leucine, L-lysine, L-methionine, L-phenylalanine, L-proline, L-serine, L-threonine, L-tryptophan, L-tyrosine, and L-valine.

10. The compound of claim 1, wherein Q is an indolyl group or an indolyl group substituted with one or more substituents independently selected from the group consisting of F, Cl, Br, I, —($C_1$-$C_6$) alkyl, —($C_1$-$C_6$) fluoro-substituted alkyl, —($C_3$-$C_9$) cycloalkyl, —($C_3$-$C_9$) fluoro-substituted cycloalkyl, —O—($C_1$-$C_6$) alkyl, —O—($C_1$-$C_6$) fluoro-substituted alkyl, —O—($C_3$-$C_9$) cycloalkyl, —O—($C_3$-$C_9$) fluoro-substituted cycloalkyl, -aryl, —O-aryl, —O—($C_1$-$C_4$) alkyl-aryl, —O—($C_1$-$C_4$) alkyl-heterocycle, and —S(=O)$_2$—($C_1$-$C_6$) alkyl.

11. The compound of claim 10, wherein Q is an indolyl group.

12. The compound of claim 10, wherein R1, R2 and R3 are each hydrogen.

13. The compound of claim 10, wherein R4 is hydrogen.

14. A method of treating a cell proliferative disorder, comprising administering to a subject in need thereof a therapeutically effective amount of a compound of claim 1 or a pharmaceutically acceptable salt thereof, wherein the cell proliferative disorder is selected from lung cancer, colon cancer, breast cancer, pancreatic cancer, prostate cancer, chronic myelogenous leukemia, melanoma, and ovarian cancer.

15. A compound selected from the group consisting of
(±)-Trans-3-(5,6-dihydro-4H-pyrrolo [3,2,1-ij] quinolin-1-yl)-4-(5-bromo-1H-indol-3-yl)-pyrrolidine-2,5-dione,
(±)-Trans-3-(5,6-dihydro-4H-pyrrolo [3,2,1-ij] quinolin-1-yl)-4-(5-phenyl-1H-indol-3-yl)-pyrrolidine-2,5-dione, (±)-Trans-3-(5,6-dihydro-4H-pyrrolo [3,2,1-ij] quinolin-1-yl)-4-(5-(1-naphthyl)-1H-indol-3-yl)-pyrrolidine-2,5-dione, (±)-Trans-3-(5,6-dihydro-4H-pyrrolo [3,2,1-ij] quinolin-1-yl)-4-(5-(4-methoxyphenyl)-1H-indol-3-yl)-pyrrolidine-2,5-dione, (±)-Trans-3-(5,6-dihydro-4H-pyrrolo [3,2,1-ij] quinolin-1-yl)-4-(5-(3-methylphenyl)-1H-indol-3-yl)-pyrrolidine-2,5-dione, (±)-Trans-3-(5,6-dihydro-4H-pyrrolo [3,2,1-ij] quinolin-1-yl)-4-(2-chloro-4-fluorophenyl)-pyrrolidine-2,5-dione, (±)-Trans-3-(5,6-dihydro-4H-pyrrolo [3,2,1-ij] quinolin-1-yl)-4-(2,6-dichlorophenyl)-pyrrolidine-2,5-dione, (±)-Trans-3-(5,6-dihydro-4H-pyrrolo [3,2,1-ij] quinolin-1-yl)-4-(4-bromophenyl)-pyrrolidine-2,5-dione, (±)-Trans-3-(5,6-dihydro-4H-pyrrolo [3,2,1-ij] quinolin-1-yl)-4-(4-chlorophenyl)-pyrrolidine-2,5-dione, (±)-Trans-3-(5,6-dihydro-4H-pyrrolo [3,2,1-ij] quinolin-1-yl)-4-(4-trifluoromethoxyphenyl)-pyrrolidine-2,5-dione, (±)-Trans-3-(5,6-dihydro-4H-pyrrolo [3,2,1-ij] quinolin-1-yl)-4-(thiophen-3-yl)-pyrrolidine-2,5-dione, (±)-Trans-3-(5,6-dihydro-4H-pyrrolo [3,2,1-ij] quinolin-1-yl)-4-(2-fluorophenyl)-pyrrolidine-2,5-dione, (±)-Trans-3-(5,6-dihydro-4H-pyrrolo [3,2,1-ij] quinolin-1-yl)-4-(2-thiophen-2-yl)-pyrrolidine-2,5-dione, (±)-Trans-3-(5,6-dihydro-4H-pyrrolo [3,2,1-ij] quinolin-1-yl)-4-(2,4-dichlorophenyl)-pyrrolidine-2,5-dione, (±)-Trans-3-(5,6-dihydro-4H-pyrrolo [3,2,1-ij] quinolin-1-yl)-4-phenyl-pyrrolidine-2,5-dione, (±)-Trans-3-(5,6-dihydro-4H-pyrrolo [3,2,1-ij] quinolin-1-yl)-4-(2-chlorophenyl)-pyrrolidine-2,5-dione, (±)-Trans-3-(5,6-dihydro-4H-pyrrolo [3,2,1-ij] quinolin-1-yl)-4-(N-methylindol-3-yl)-pyrrolidine-2,5-dione, (±)-Cis-3-(5,6-dihydro-4H-pyrrolo [3,2,1-ij] quinolin-1-yl)-4-(4-methoxyphenyl)-pyrrolidine-2,5-dione, (±)-Cis-3-(5,6-dihydro-4H-pyrrolo [3,2,1-ij] quinolin-1-yl)-4-(2,5-dimethoxyphenyl)-pyrrolidine-2,5-dione, (±)-Cis-3-(5,6-dihydro-4H-pyrrolo [3,2,1-ij] quinolin-1-yl)-4-(2-chloro-4-fluoro-phenyl)-pyrrolidine-2,5-dione, (±)-Cis-3-(5,6-dihydro-4H-pyrrolo [3,2,1-ij] quinolin-1-yl)-4-(3-chlorophenyl)-pyrrolidine-2,5-dione, (±)-cis-3-(5,6-dihydro-4H-pyrrolo [3,2,1-ij] quinolin-1-yl)-4-(1-methylindol-3-yl)-1-methyl pyrrolidine-2,5-dione, (±)-trans-3-(5,6-dihydro-4H-pyrrolo [3,2,1-ij] quinolin-1-yl)-4-(3-methoxyphenyl)-pyrrolidine-2,5-dione, (±)-trans-3-(5,6-dihydro-4H-pyrrolo [3,2,1-ij] quinolin-1-yl)-4-(3-hydroxyphenyl)-pyrrolidine-2,5-dione, (±)-trans-3-(5,6-dihydro-4H-pyrrolo [3,2,1-ij] quinolin-1-yl)-4-(4-fluorophenyl)-pyrrolidine-2,5-dione, (±)-trans-3-[4-(benzyloxy)phenyl]-4-(5,6-dihydro-4H-pyrrolo [3,2,1-ij] quinolin-1-yl)-pyrrolidine-2,5-dione, and (±)-trans-3-(5,6-dihydro-4H-pyrrolo [3,2,1-ij] quinolin-1-yl)-4-(4-hydroxyphenyl)-pyrrolidine-2,5-dione.

16. A compound selected from the group consisting of (±)-Phosphoric acid mono-[trans-3-(5,6-dihydro-4H-pyrrolo [3,2,1-ij] quinolin-1-yl)-4-(1H-indol-3-yl)-2,5-dioxo-pyrrolidin-1-yl-methyl] ester, (±)-trans-2-amino-propionic acid-3-(5,6-dihydro-4H-pyrrolo [3,2,1-ij] quinolin-1-yl)-4-(1H-indol-3-yl)-2,5-dioxo-pyrrolidin-1-yl-methyl ester, (±)-trans-2-amino-acetic acid-3-(5,6-dihydro-4H-pyrrolo [3,2,1-ij] quinolin-1-yl)-4-(1H-indol-3-yl)-2,5-dioxo-pyrrolidin-1-yl-methyl ester, (±)-trans-2-dimethylamino-acetic acid-3-(5,6-dihydro-4H-pyrrolo [3,2,1-ij] quinolin-1-yl)-4-(1H-indol-3-yl)-2,5-dioxo-pyrrolidin-1-yl-methyl ester, and (±)-trans-isonicotinic acid-3-(5,6-dihydro-4H-pyrrolo [3,2,1-ij] quinolin-1-yl)-4-(1H-indol-3-yl)-2,5-dioxo-pyrrolidin-1-yl-methyl ester.

17. A compound selected from the group consisting of 3-(5,6-dihydro-4H-pyrrolo [3,2,1-ij] quinolin-1-yl)-4-(2-trifluoromethyl-phenyl)-pyrrole-2,5-dione, 3-(5,6-dihydro-4H-pyrrolo [3,2,1-ij] quinolin-1-yl)-4-thiophen-2-yl-pyrrole-2,5-dione, 3-(5,6-dihydro-4H-pyrrolo [3,2,1-ij] quinolin-1-yl)-4-(3-methoxy-phenyl)-pyrrole-2,5-dione, 3-(5,6-dihydro-4H-pyrrolo [3,2,1-ij] quinolin-1-yl)-4-pyridin-2-yl-pyrrole-2,5-dione, 3-(5,6-dihydro-4H-pyrrolo [3,2,1-ij] quinolin-1-yl)-4-(4-methoxy-phenyl)-pyrrole-2,5-dione, 3-benzo[1,3]dioxol-5-yl-4-(5,6-dihydro-4H-pyrrolo [3,2,1-ij] quinolin-1-yl)-pyrrole-2,5-dione, 3-(5,6-dihydro-4H-pyrrolo [3,2,1-ij] quinolin-1-yl)-4-phenyl-pyrrole-2,5-dione, 3-benzo[b]thiophen-2-yl-4-(5,6-dihydro-4H-pyrrolo [3,2,1-ij] quinolin-1-yl)-pyrrole-2,5-dione, 3-(5,6-dihydro-4H-pyrrolo [3,2,1-ij] quinolin-1-yl)-4-(3-phenoxy-phenyl)-pyrrole-2,5-dione, 3-(5,6-dihydro-4H-pyrrolo [3,2,1-ij] quinolin-1-yl)-4-(3-chloro-phenyl)-pyrrole-2,5-dione, 3-(5,6-dihydro-4H-pyrrolo [3,2,1-ij] quinolin-1-yl)-4-(2-chloro-phenyl)-pyrrole-2,5-dione, 3-(5,6-dihydro-4H-pyrrolo [3,2,1-ij] quinolin-1-yl)-4-(2,5-dimethoxy-phenyl)-pyrrole-2,5-dione, 3-(5,6-dihydro-4H-pyrrolo [3,2,1-ij] quinolin-1-yl)-4-(2-chloro-4-fluoro-phenyl)-pyrrole-2,5-dione, 3-(5,6-dihydro-4H-pyrrolo [3,2,1-ij] quinolin-1-yl)-4-naphthalene-1-yl-pyrrole-2,5-dione, 3-(5,6-dihydro-4H-pyrrolo [3,2,1-ij] quinolin-1-yl)-4-(2,6-di chloro-phenyl)-pyrrole-2,5-dione, 3-(5,6-dihydro-4H-pyrrolo [3,2,1-ij] quinolin-1-yl)-4-(2-bromo-phenyl)-pyrrole-2,5-dione, 3-(5,6-dihydro-4H-pyrrolo [3,2,1-ij] quinolin-1-yl)-4-indol-1-yl-pyrrole-2,5-dione, 3-(5,6-dihydro-4H-pyrrolo [3,2,1-ij] quinolin-1-yl)-4-pyridine-3-yl-pyrrole-2,5-dione, 3-(5,6-dihydro-4H-pyrrolo [3,2,1-ij] quinolin-1-yl)-4-pyridine-4-yl-pyrrole-2,5-dione, 3-biphenyl-4-yl-4-(5,6-dihydro-4H-pyrrolo [3,2,1-ij] quinolin-1-yl)-pyrrole-2,5-dione, 3-(5,6-dihydro-4H-pyrrolo [3,2,1-ij] quinolin-1-yl)-4-(4-methanesulfonyl-phenyl)-pyrrole-2,5-dione, 3-(5,6-dihydro-4H-pyrrolo [3,2,1-ij] quinolin-1-yl)-4-(2-trifluoromethyl-quinolin-4-yl-sulfanyl)-pyrrole-2,5-dione, 3-(4-benzoloxyphenyl)-4-(5,6-dihydro-4H-pyrrolo [3,2,1-ij] quinolin-1-yl)-pyrrole-2,5-dione, 3-(5,6-dihydro-4H-pyrrolo [3,2,1-ij] quinolin-1-yl)-4-[4-(2-morpholin-4-yl-ethoxy)-phenyl]-pyrrole-2,5-dione, 3-(5,6-dihydro-4H-pyrrolo [3,2,1-ij] quinolin-1-yl)-4-(5-1-naphthyl-1H-indol-3-yl)-pyrrole-2,5-dione, 3-(5,6-dihydro-4H-pyrrolo [3,2,1-ij] quinolin-1-yl)-4-(5-phenyl-1H-indol-3-yl)-pyrrole-2,5-dione, 3-(5,6-dihydro-4H-pyrrolo [3,2,1-ij] quinolin-1-yl)-4-(5-(4-methoxyphenyl)-1H-indol-3yl)-pyrrole-2,5-dione, 3-(5,6-dihydro-4H-pyrrolo [3,2,1-ij] quinolin-1-yl)-4-(5-(3-methylphenyl)-1H-indol-3-yl)-pyrrole-2,5-dione, 3-(5,6-dihydro-4H-pyrrolo [3,2,1-ij] quinolin-1-yl)-4-(1-methylindol-3-yl)-1-methyl-pyrrole-2,5-dione, 3-[4-(benzyloxy)-phenyl]-4-(5,6-dihydro-4H-pyrrolo [3,2,1-ij] quinolin-1-yl)-1H-pyrrole-2,5-dione, and 3-(5,6-dihydro-4H-pyrrolo [3,2,1-ij] quinolin-1-yl)-4-(4-fluorophenyl)-1H-pyrrole-2,5-dione.

\* \* \* \* \*